United States Patent
Freire et al.

(10) Patent No.: US 9,730,913 B2
(45) Date of Patent: *Aug. 15, 2017

(54) HIGH AFFINITY BETA LACTAMASE INHIBITORS

(71) Applicant: THE JOHNS HOPKINS UNIVERSITY, Baltimore, MD (US)

(72) Inventors: Ernesto Freire, Baltimore, MD (US); Rogelio Siles, Cockeysville, MD (US); Patrick C. Ross, College Park, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 107 days.

This patent is subject to a terminal disclaimer.

(21) Appl. No.: 14/351,280

(22) PCT Filed: Oct. 12, 2012

(86) PCT No.: PCT/US2012/059999
§ 371 (c)(1),
(2) Date: Apr. 11, 2014

(87) PCT Pub. No.: WO2013/056079
PCT Pub. Date: Apr. 18, 2013

(65) Prior Publication Data
US 2014/0256778 A1 Sep. 11, 2014

Related U.S. Application Data

(60) Provisional application No. 61/546,661, filed on Oct. 13, 2011.

(51) Int. Cl.
| | | |
|---|---|---|
| *C07C 311/13* | (2006.01) | |
| *A61K 31/41* | (2006.01) | |
| *A61K 31/18* | (2006.01) | |
| *C07C 311/27* | (2006.01) | |
| *C07D 257/04* | (2006.01) | |
| *A61K 45/06* | (2006.01) | |

(52) U.S. Cl.
CPC .............. *A61K 31/41* (2013.01); *A61K 31/18* (2013.01); *A61K 45/06* (2013.01); *C07C 311/13* (2013.01); *C07C 311/27* (2013.01); *C07D 257/04* (2013.01)

(58) Field of Classification Search
CPC .............................. A61K 31/41; C07C 311/13
See application file for complete search history.

(56) References Cited

U.S. PATENT DOCUMENTS

| 4,035,421 A | * | 7/1977 | Snyder, Jr. ...................... 564/92 |
| 7,842,791 B2 | * | 11/2010 | Britten et al. ............... 536/13.1 |
| 2004/0058896 A1 | * | 3/2004 | Dietrich et al. .............. 514/171 |
| 2005/0186664 A1 | * | 8/2005 | Rosen et al. ................. 435/69.7 |
| 2009/0124828 A1 | * | 5/2009 | Reddy et al. ................. 562/429 |
| 2009/0240052 A1 | * | 9/2009 | Yokotani et al. ............. 544/124 |

FOREIGN PATENT DOCUMENTS

| WO | 02067865 A2 | 9/2002 |
| WO | 2005089269 A2 | 9/2005 |
| WO | 2009120783 A1 | 10/2009 |

OTHER PUBLICATIONS

Lee, Bioorganic & Medicinal Chemistry Letters, 2008, vol. 18, p. 5676-5679.*
Siles, Bioorganic & Medicinal Chemistry Letters, 2011, vol. 21, p. 5305-5309.*
STN RN No. 1164461-42-0, entered into STN Jul. 19, 2009.*
Koehler, K. A. and Lienhard, G. E. (1971) Biochemistry 10, 2477-2483.
Ness, S., Kindler, A. M., Mark Paetzel., Gold, M., Jensen, S. E., Jones, J. B., Strynadka, N. C. (2000) Biochemistry 39, 5312-5321.
Morandi, F., Caselli, E., Morandi, S., Focia, P. J., Blazquez, J., Shoichet, B. K., and Prati, F. (2003) J. Am. Chem. Soc. 125, 685-695.
Powers, R. A., and Schoichet, B. K. (2002) J. Med. Chem. 45 3222-3234.
Rudgers, G. W., Huang, W., Palzkill, T. (2001) Antimicrobial Agents and 5 Chem. 45 3279-3286.
Bonomo, R. A, Rudin, S. A, Shlaes, D. M. (1997) FEMS Microbiology Letters 148 59-62.
Velazquez-Campoy, A., Kiso, Y. and Freire, E. (2001) Arch. Biochim. Biophys. 390 169-175.
Ohtaka, H., Velazquez-Campoy, A. and Freire, E. (2002) Protein Science 11 1908-1916.
Queenan and Bush, Clin. Microbiol. Rev., 20, 440-458 (2007).
Siles et al., "Synthesis and biochemical evaluation of triazole/tetrazole-containing sulfonamides against thrombin and related serine proteases," Bioorganic & Medicinal Chemistry Letters, Jul. 14, 2011, vol. 21, pp. 5305-5309.
International Search Report dated Apr. 24, 2014 for PCT/US2012/059999.
International Preliminary Report on Patentability dated Mar. 21, 2013 for PCT/US2012/059999.

* cited by examiner

*Primary Examiner* — Rebecca Anderson
*Assistant Examiner* — Karen Cheng
(74) *Attorney, Agent, or Firm* — Michael Best & Friedrich, LLP; Jeffrey W. Childers

(57) ABSTRACT

Inhibitors of beta lactamases and their use in treating bacterial infections are disclosed.

45 Claims, 3 Drawing Sheets ef-rs-08-052 ef-rs-05-076 ef-rs-04-090 ef-rs-05-049 ef-rs-03-075

HIGH AFFINITY BETA LACTAMASE INHIBITORS

CROSS REFERENCE TO RELATED APPLICATIONS

This application is a 35 U.S.C. §371 U.S. national phase entry of International Application No. PCT/US2012/059999 having an international filing date of Oct. 12, 2012, which claims the benefit of U.S. Provisional Application No. 61/546,661, filed Oct. 13, 2011.

FEDERALLY SPONSORED RESEARCH OR DEVELOPMENT

This invention was made in part with United States Government support under GM57144 awarded by the National Institutes of Health (NIH). The U.S. Government has certain rights in the invention.

BACKGROUND

Drug resistance to antibiotics, especially beta lactam antibiotics, such as penicillin, cephalosporin and related compounds, is one of the most serious problems in the treatment of infectious diseases. Drug resistance to antibiotics represents not only a significant medical problem, but a major public health and economic burden. Between 1980 and 1992, the death rate, due to infectious diseases as the underlying cause of death, increased 58%, from 41 deaths to 65 deaths per 100,000 people in the United States. Age adjusted mortality from infectious diseases increased 39% during the same period. Infectious disease mortality increased 25% among those aged 65 years and older (from 271 to 338 per 100,000) and 6.3 times among 25-44 year olds (from 6 to 38 per 100,000). Mortality due to respiratory tract infections increased 20% (from 25-30 deaths per 100,000).

Recent CDC reports indicate that two million Americans acquire infections in hospitals each year, the cost of which runs to an estimated $4.5 billion. In 2003, epidemiologists reported in The New England Journal of Medicine that 5 to 10 percent of patients admitted to hospitals acquire an infection during their stay and that the risk for a hospital-acquired infection has increased steadily in recent decades. Of these infections, 70% are due to microbes that are resistant to one or more antibiotics and in 30-40% of the infections the causative microbe is resistant to first line treatment. The rate at which patients acquire infections in hospitals rose by 36% in 1995 compared with 1975. In 1995, 35.9 million patients entered hospitals in the United States compared with 37.7 million in 1975. For the same period, lengths of stay dropped to an average of 5.3 days from 7.9 days due to managed health care guidelines. The number of infections per 1,000 patient days, however, rose to 9.77 from 7.18.

Penicillin exerts its effects by disrupting the synthesis of the bacterial cell wall. The endogenous bacterial enzymes that destroy penicillin and other beta lactam antibiotics and eliminate their efficacy are the beta lactamases. The name derives from their ability to cleave the beta lactam ring of the antibiotic. At the clinical level, the most important beta lactamases belong to the so-called class A enzymes (TEM) and to the class C enzymes (AmpC). These enzymes are serine hydrolases; they have a critical serine in their catalytic site. The metallo-enzyme Class B beta-lactamases (IMP) also are important clinically. To overcome the negative effects of these enzymes, small molecules that neutralize the action of beta lactamase (beta lactamase inhibitors) are commonly used in combination with antibiotics. The three beta lactamase inhibitors currently in clinical use, clavulanic acid, sulbactam and tazobactam, are all transition state analogs that utilize the same beta lactam core that is present in the antibiotics themselves.

A disturbing trend has been the growing number of bacteria that have evolved resistance mechanisms against beta lactamase inhibitors. A major form of resistance is the appearance of mutations in the beta lactamase enzymes that abolish the effectiveness of the inhibitors while preserving the ability of the enzymes to hydrolyze the antibiotic molecules. These observations underscore the need for new non-beta lactam based beta lactamase inhibitors that are active against a wide variety of beta lactamases, including those that are resistant to clavulanic acid, sulbactam and tazobactam.

SUMMARY

The presently disclosed subject matter provides beta-lactamase inhibitors and methods of their use for inhibiting a beta-lactamase, treating a bacterial infection, and overcoming antibacterial resistance.

In some aspects, the presently disclosed subject matter provides a compound of Formula (I):

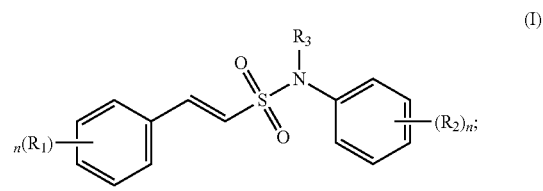

wherein:
  each n is independently an integer selected from the group consisting of 0, 1, 2, 3, 4, and 5;
  each $R_2$ and $R_3$ is independently selected from the group consisting of: hydrogen, hydroxyl, alkoxyl,

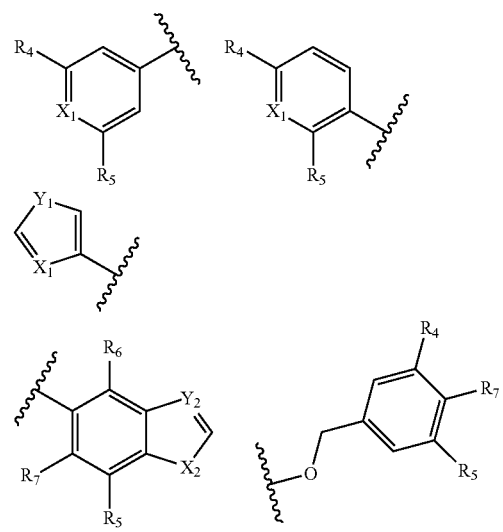

3

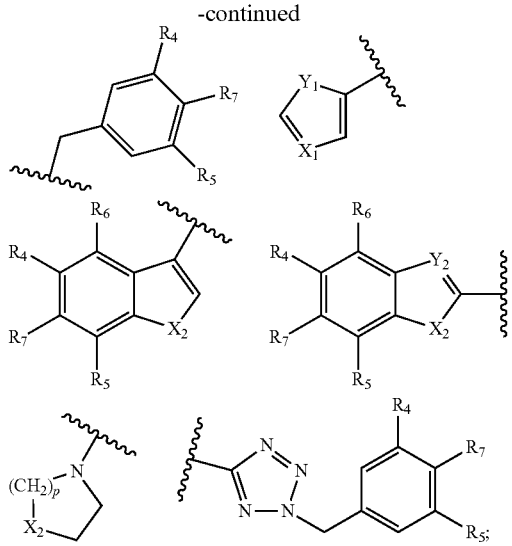

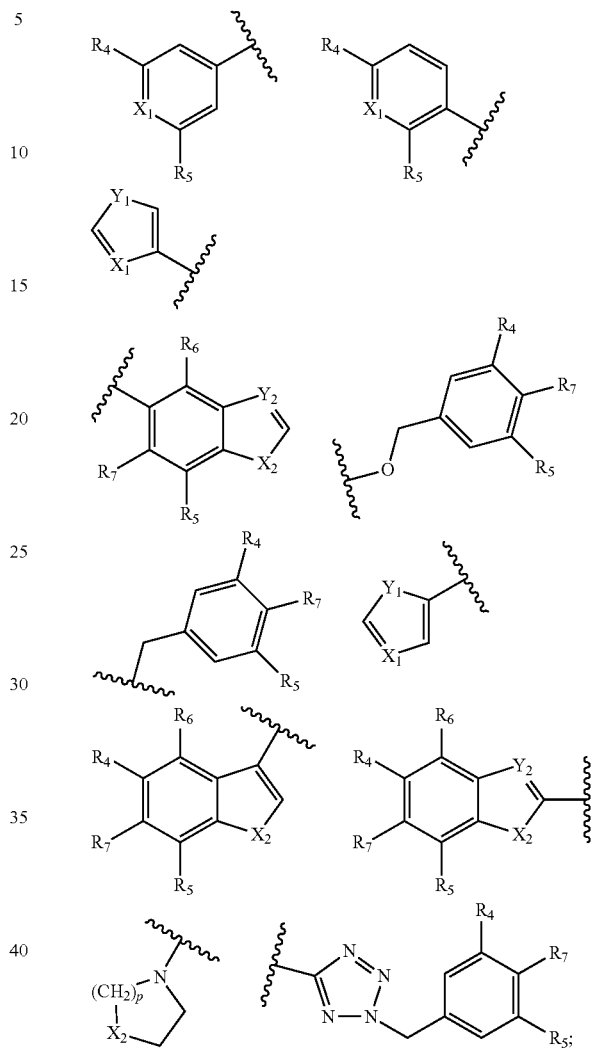

p is an integer selected from the group consisting of 1 and 2;

$X_1$ is selected from the group consisting of N and $CR_8$;

$X_2$ is selected from the group consisting of S, O, $NR_8$, and $CR_8R_9$;

$Y_1$ is selected from the group consisting of S, O, and $NR_8$;

$Y_2$ is selected from the group consisting of N and $CR_8$; under the proviso that if $R_3$ is an unsubstituted benzyl or halo-substituted benzyl, then $R_1$ and $R_2$ are not both halogen;

$R_1$, $R_4$, $R_5$, $R_6$, $R_7$, $R_8$, and $R_9$ are each independently selected from the group consisting of hydrogen, substituted or unsubstituted alkyl, alkoxyl, hydroxyl, hydroxyalkyl, carboxyl, acyl, including —$COOR_{10}$, wherein $R_{10}$ is lower alkyl, carbonyl, carbamoyl, alkylcarbamoyl, halogen, amino, nitro, nitrile, amide, haloalkyl, aryl, cycloalkyl, aralkyloxyl, and —$SO_3H$;

and a pharmaceutically acceptable salt, prodrug, or solvate thereof.

In particular aspects, the presently disclosed subject matter provides a pharmaceutical composition comprising a compound of Formula (I), one or more antibacterial agents, and a pharmaceutically acceptable carrier, wherein the one or more antibacterial agents can include a beta-lactam antibiotic, a fluoroquinolone, a quinolone, a macrolide, a tetracycline, and combinations thereof.

In other aspects, the presently disclosed subject matter provides a method for inhibiting a beta lactamase, the method comprising contacting the beta lactamase with a compound of Formula (I) in an amount to inhibit the beta lactamase:

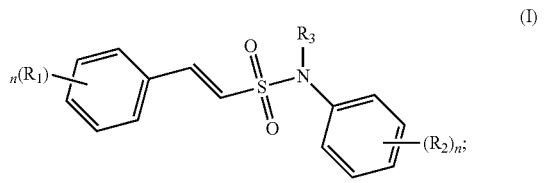

wherein:

each n is independently an integer selected from the group consisting of 0, 1, 2, 3, 4, and 5;

4 each $R_2$ and $R_3$ is independently selected from the group consisting of: hydrogen, hydroxyl, alkoxyl, p is an integer selected from the group consisting of 1 and 2;

$X_1$ is selected from the group consisting of N and $CR_8$;

$X_2$ is selected from the group consisting of S, O, $NR_8$, and $CR_8R_9$;

$Y_1$ is selected from the group consisting of S, O, and $NR_8$;

$Y_2$ is selected from the group consisting of N and $CR_8$;

$R_1$, $R_4$, $R_5$, $R_6$, $R_7$, $R_8$, and $R_9$ are each independently selected from the group consisting of hydrogen, substituted or unsubstituted alkyl, alkoxyl, hydroxyl, hydroxyalkyl, carboxyl, acyl, including —$COOR_{10}$, wherein $R_{10}$ is lower alkyl, carbonyl, carbamoyl, alkylcarbamoyl, halogen, amino, nitro, nitrile, amide, haloalkyl, aryl, cycloalkyl, aralkyloxyl, and —$SO_3H$;

and a pharmaceutically acceptable salt, prodrug, or solvate thereof.

In yet other aspects, the presently disclosed subject matter provides a method for treating a bacterial infection in a subject in need of treatment thereof, the method comprising administering to the subject a therapeutically-effective amount of a beta-lactam antibiotic, optionally in combination with one or more other antibacterial agents, in combination with a therapeutically-effective amount of a compound of Formula (I) as defined immediately hereinabove.

In further aspects, the presently disclosed subject matter provides a method for overcoming a bacterial resistance in a subject in need of treatment thereof, the method comprising administering to the subject a therapeutically effective amount of a compound of Formula (I) as defined immediately hereinabove.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

Figure 1:
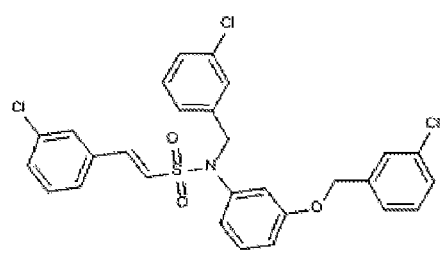
Figure 1:
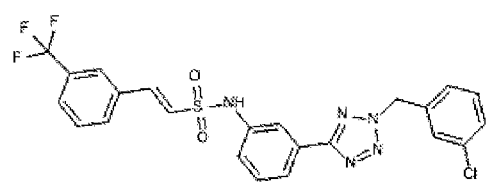
Figure 1:
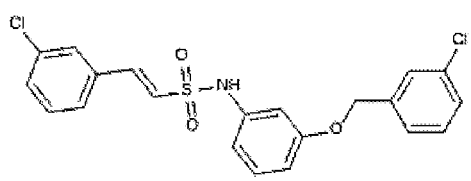
Figure 1:
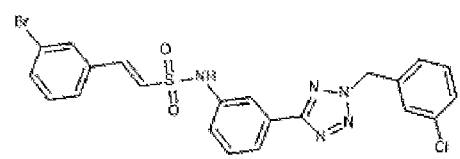
Figure 1:
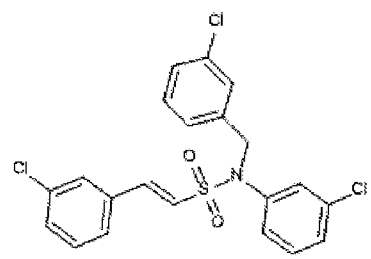
Figure 2:
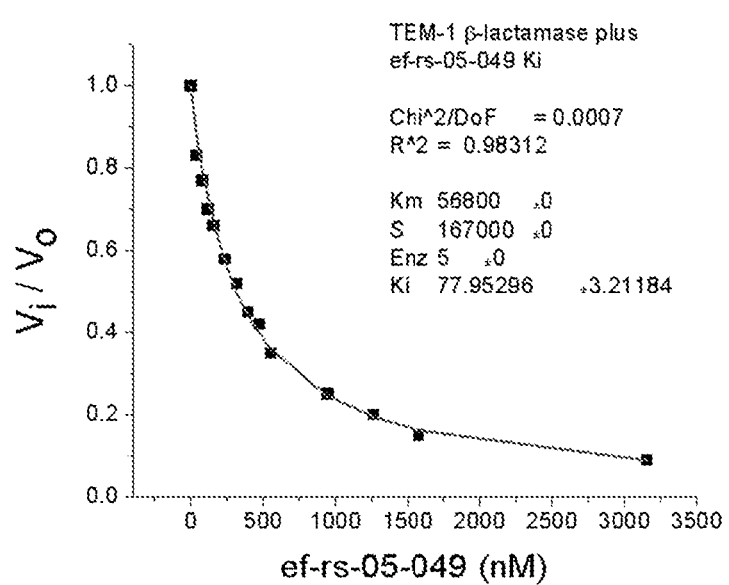
Figure 3:
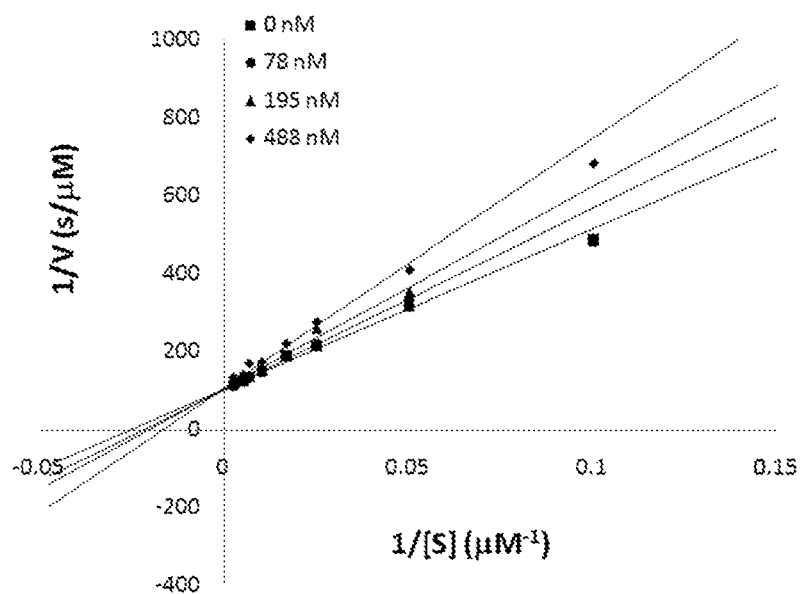

Having thus described the presently disclosed subject matter in general terms, reference will now be made to the accompanying Figures, which are not necessarily drawn to scale, and wherein:

FIG. 1 provides representative presently disclosed beta lactamase inhibitors;

FIG. 2 shows measurement of the inhibition constant of ef-rs-05-049 against wild type TEM-1 β-lactamase. TEM-1 activity in the absence or presence of varying concentrations of ef-rs-05-049 were fit to equations for inhibition, with a resultant Ki of 78.0±3.2 nM; and FIG. 3 shows a double reciprocal plot of substrate concentration vs. reaction velocity in the presence of various concentrations of ef-rs-05-049. Intersection on the y-axis of the fits of the data to the Michaelis-Menten equation indicate competitive inhibition of TEM-1 beta-lactamase by this compound.

DETAILED DESCRIPTION

The presently disclosed subject matter now will be described more fully hereinafter with reference to the accompanying Figures, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

I. Beta-Lactamase Inhibitors And Methods Of Their Use For Inhibiting A Beta-Lactamase, Treating A Bacterial Infection, And Overcoming Antibacterial Resistance.

Beta lactamases define the most common drug resistance mechanism to beta lactam antibiotics, such as penicillin, cephalosporins and other related molecules. Beta lactamases are bacterial enzymes that break down the antibiotics and render them ineffective. Drug resistant to antibiotics has been acknowledged to be one of the most important public health problems. In the past, antibiotic resistance has been alleviated by administering a combination of the antibiotic with a beta lactamase inhibitor. Resistance to antibiotics is compounded by the growing number of microorganisms that are resistant to existing beta lactamase inhibitors, such as clavulanic acid, sulbactam, and tazobactam.

Without being limited to any particular theory or mechanism of action, it is believed that evolutionary selection and genetic transformation have made the problem of antibiotic resistance pressing. Most antibiotic drugs are derivatives of naturally occurring bactericides (Davies, Science, 264, 375-382 (1994)), and many resistance mechanisms evolved long ago. Human use of antibiotics has refined these mechanisms and promoted their spread through gene transfer (Davies, Science, 264, 375-382 (1994)). A resistance mechanism originating in one species of bacteria can be expected to spread throughout the biosphere.

Beta-lactam antibiotics inhibit bacterial cell wall biosynthesis (Tomasz, Rev. Infect. Dis., 8, S270-S278 (1986)). They form covalent complexes with and consequently inactivate a group of transpeptidases/carboxypeptidases called the Penicillin Binding Proteins (PBPs). PBP inactivation disrupts cell wall biosynthesis, leading to self-lysis and death of the bacteria. Beta-lactam antibiotics have been widely prescribed. In the absence of resistance, beta-lactams are the first choice for treatment in 45 of 78 common bacterial infections (Goodman & Gilman's The Pharmacological Basis of Therapeutics (Hardman et al., eds., McGraw-Hill, New York, 1996)).

Bacterial adaptations to beta-lactam drugs (e.g., amoxicillin, cephalothin, clavulanate, and aztreonam) are among the best studied and most pernicious forms of antibiotic resistance. Without being limited to any particular theory or mechanism of action, it is believed that bacteria use several different mechanisms to escape from beta-lactam antibiotics (Sanders, Clinical Infectious Disease, 14, 1089-1099 (1992); Li et al., Antimicrob. Agents Chemother., 39, 1948-1953 (1995)). Probably the most widespread is the hydrolysis of beta-lactams by beta-lactamase enzymes.

Beta-lactamases are endogenous bacterial enzymes that destroy beta-lactam antibiotics and eliminate their efficacy. The name derives from their ability to cleave the beta-lactam ring. The structures of many beta-lactamases are known at the atomic level and available in the protein database. At least four classes of beta-lactamases are known: Classes A, B, C and D. At the clinical level, the most important beta-lactamases belong to Class A (TEM), Class B (IMP) and Class C (AmpC). TEM and Amp-C are serine hydrolases and have a critical serine in their catalytic site. TEM and AmpC) among different bacterial species share high sequence identity and structural similarity (Galleni, et al., Biochem. J, 250, 753-760 (1988); Galleni, et al., Biochem. J, 250, 753-760 (1988); Usher et al., Biochemistry, 30, 16082-16092 (1998)). IMP is a metallo-hydrolase with catalytically active zinc ions.

One way to overcome the negative effects of beta-lactamases is to use molecules that neutralize the action of beta-lactamase (known as beta-lactamase inhibitors or inhibitors of beta-lactamase) in combination with antibiotics. The three beta-lactamase inhibitors currently in clinical use (clavulanic acid, sulbactam and tazobactam) are all transition state analogs that utilize the same beta-lactam core that is present in the antibiotics themselves.

The similarity between the beta-lactam antibiotics and beta-lactam-based beta-lactam-inhibitors has proven to be a serious problem. Resistance to such beta-lactam-based beta-lactamase inhibitors arises through modifications of previously susceptible mechanisms. Certain mutations in beta-lactamase, for example, reduce the effectiveness of beta-lactam-based beta-lactamase inhibitors while preserving the ability of the beta-lactamase to hydrolyze the antibiotic molecules. Certain point substitutions in beta-lactamases allow the enzymes to hydrolyze compounds designed to evade them (Philippon et al., Antimicrob. Agents Chemother., 33, 1131-1136 (1989)). Other substitutions reduce the affinity of beta-lactam inhibitors for the enzymes (Saves, et al., J. Biol. Chem., 270, 18240-18245 (1995)) or allow the enzymes to simply hydrolyze them. Furthermore, several gram-positive bacteria (e.g., Staph. Aureus) have acquired sensor proteins that detect beta-lactams in the environment of the cell (Bennet and Chopra, Antimicrob. Agents Chemotherapy, 37, 153-158 (1993)). Beta-lactam binding to these sensors leads to transcriptional up-regulation of the beta-lactamase. Beta-lactam-based beta-lactamase inhibitors, thus, can induce the production of the enzyme that they are meant to inhibit, preventing or reducing their efficacy.

Two different types of beta-lactamase mutations have been described. Mutations that reduce the ability of inhibitors to block enzymatic activity and mutations that extend the spectrum of the antibiotics that are digested. To be effective, beta-lactamase inhibitors need to be active against both. Extended spectrum beta-lactamase mutants are able to digest beta-lactams antibiotics that are spatially restricted from entering the active site of the wild type enzyme (e.g., cephalosporins). TEM-12, an arginine to serine mutation at residue 164, is an example of this class. R164 forms a hydrogen bond to D179, stabilizing a loop structure that blocks cephalosporin entrance to the active site (Maveyraud, et. al., J Biol Chem, 271, 10482-10489 (1996)). The mutation of residue 164 to serine destabilizes the loop structure and allows cephalosporins to enter the active site. As shown in Table 1, the presently disclosed compounds are active against these mutations.

The second type of mutations (resistant mutations) affects inhibitors currently in clinical use. These mutations lead to loss of inhibitory activity. When these inhibitor resistant mutations arise, for example TEM-30 and TEM-40, inhibitory activity may decrease by upwards of 100 fold (Table 1 below). With TEM-30, the mutation of an arginine to a serine removes a water from the beta-lactamase active site (Meroueh, et al., J Am Chem Soc, 124, 9422-9430 (2002)). This water is important in the suicide inhibition scheme of the three clinical inhibitors, and lack of this water leads to loss of inhibitory activity. With TEM-40, the switch of a methionine to an isoleucine alters the hydrogen bonding scheme of amino acids within the active site (Wang, et. al., J Biol Chem, 277, 32149-32156 (2002)). This change distorts the positioning of the serine 70 residue to the extent that inhibition is greatly decreased.

AmpC like beta-lactamases (Class C), are not inhibited by current clinical beta-lactamase inhibitors. There are currently no clinical beta-lactamase inhibitors targeted toward this class of beta-lactamases. The presently disclosed compounds are effective not only against TEM resistant mutations, but also against AmpC beta-lactamase.

TABLE 1

Inhibitory Potency ($IC_{50}$) of Beta-Lactamase Inhibitors in Clinical Use Against Different Beta-Lactamases

| | TEM-1[a] | TEM-30[a] | TEM-40[b] | AmpC[a] |
|---|---|---|---|---|
| Clavulanic Acid | 0.09 μM | 4 μM | 12 μM | 59 to >1000 μM |
| Sulbactam | 6.1 μM | 81 μM | 150 μM | 3.8 to >100 μM |
| Tazobactam | 0.04 μM | 2.3 μM | 5 μM | 19 μM |

[a]Bush et. al., Antimicrobial Agents and Chemotherapy, 39, 1211-1233 (1995).
[b]Yang et. al., Pharmacology & Therapeutics, 83, 141-151 (1999).

Class B beta-lactamases (IMP) are generally known as carbapenamases and digest most beta-lactams, monobactams excepted. These enzymes are not serine proteases, but instead contain two catalytically active zinc ions. Current beta-lactamase inhibitors are not effective against this enzyme class (Queenan and Bush, Clin. Microbiol. Rev., 20, 440-458 (2007)). The presently disclosed compounds show inhibition against IMP-1, exhibiting inhibition constants from 203±51 nM (ef-rs-08-052), 487±90 nM (ef-rs-04-090), and 496±57 nM (ef-rs-03-075).

Without being limited to any particular theory or mechanism of action, it is believed that one reason that bacteria have been able to respond rapidly with "new" resistance mechanisms to beta-lactam-based inhibitors is that the mechanisms of action of the inhibitors are not, in fact, new, because beta-lactamases have evolved mechanisms for, e.g., sensing and/or hydrolyzing such molecules. Accordingly, as long as medicinal chemistry focuses on beta-lactam-based molecules to overcome beta-lactamases, resistance can be expected to follow shortly.

One way to avoid recapitulating this "arms race" between bacteria and lactams is to develop non-beta-lactam inhibitors that have novel chemistries and are dissimilar to beta-lactams. Such non-beta-lactam inhibitors would not themselves be degraded by beta-lactamases, and mutations in the enzymes would not be expected render such inhibitors labile to hydrolysis. Such novel inhibitors also would escape detection by beta-lactam sensor proteins that up-regulate beta-lactamase transcription, and may be unaffected by porin mutations that limit the access of beta-lactams to PBPs. Such inhibitors would allow the current beta-lactam antibiotics to effectively work against bacteria where beta-lactamases provide the dominant resistance mechanism. For example, boronic acid-based beta-lactamase inhibitors are disclosed in U.S. Pat. No. 7,183,267 and U.S. Patent Publication No. US20050124580, each of which is incorporated herein by reference in its entirety.

A. Non-peptidic, Small Molecular Weight High Affinity Beta Lactamase Inhibitors

The inhibition of beta lactamase by the presently disclosed beta lactamase inhibitors provides a way to overcome bacterial resistance and prolong the effective life of beta lactam antibiotics. The presently disclosed subject matter provides low molecular weight non-peptidic compounds that exhibit high affinity inhibitory activity against wild type and drug resistant beta lactamase mutants, including versions of the enzyme that have been shown to be resistant to clavulanic acid, sulbactam and tazobactam. More particularly, the presently disclosed inhibitors maintain activity against drug resistant and extended spectrum mutants of TEM-1 beta lactamase (TEM-12 (R164S), TEM-17 (E104K), TEM-30 (R244S), TEM-40 (M691)) and also AmpC beta lactamase and IMP-1 beta-lactamase.

The presently disclosed subject matter provides a non-peptidic, non-beta-lactam scaffold for small molecular weight compounds capable of inhibiting wild type TEM-1 beta lactamase, mutants associated with drug resistance, Class B IMP-1 and Class C AmpC beta lactamase with high affinity. The presently disclosed inhibitors are competitive and have been ranked according to their combined potency against all beta lactamase variants. High activity against all variants is an extremely desired property as the main issue in anti-infectives is drug resistance.

Accordingly, in some embodiments, the presently disclosed subject matter provides non-peptidic, small molecular weight, high affinity beta lactamase inhibitors having drug-like properties. More particularly, in some embodiments, the presently disclosed subject matter provides a compound of Formula (I):

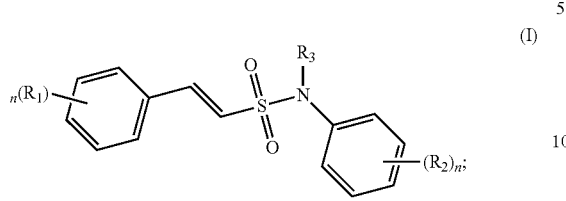

wherein:

each n is independently an integer selected from the group consisting of 0, 1, 2, 3, 4, and 5;

each $R_2$ and $R_3$ is independently selected from the group consisting of: hydrogen, hydroxyl, alkoxyl,

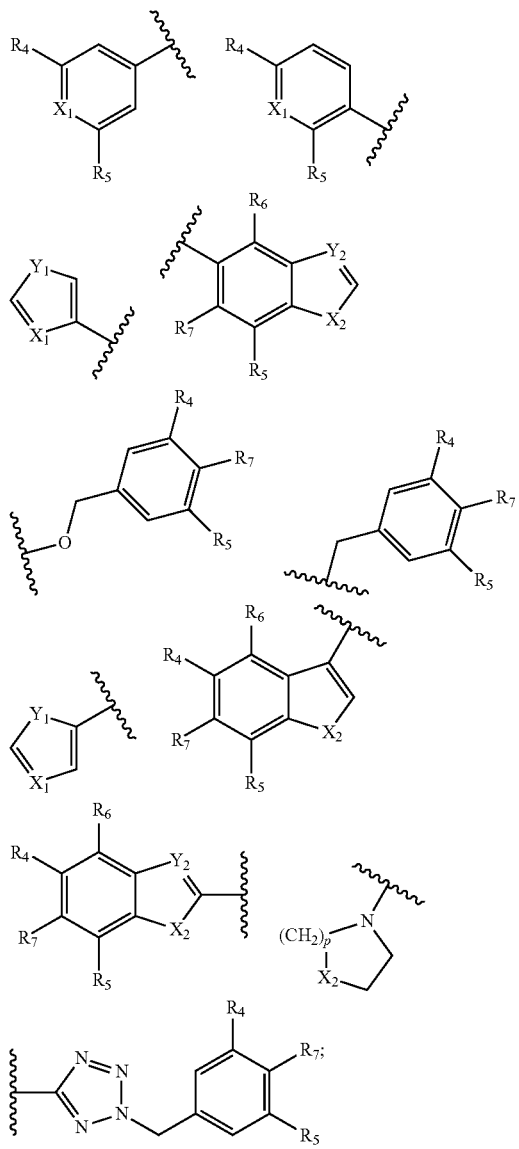

p is an integer selected from the group consisting of 1 and 2;

$X_1$ is selected from the group consisting of N and $CR_8$;

$X_2$ is selected from the group consisting of S, O, $NR_8$, and $CR_8R_9$;

$Y_1$ is selected from the group consisting of S, O, and $NR_8$;

$Y_2$ is selected from the group consisting of N and $CR_8$;

under the proviso that if $R_3$ is an unsubstituted benzyl or halo-substituted benzyl, then $R_1$ and $R_2$ are not both halogen;

$R_1$, $R_4$, $R_5$, $R_6$, $R_7$, $R_8$, and $R_9$ are each independently selected from the group consisting of hydrogen, substituted or unsubstituted alkyl, alkoxyl, hydroxyl, hydroxyalkyl, carboxyl, acyl, including —$COOR_{10}$, wherein $R_{10}$ is lower alkyl, carbonyl, carbamoyl, alkylcarbamoyl, halogen, amino, nitro, nitrile, amide, haloalkyl, aryl, cycloalkyl, aralkyloxyl, and —$SO_3H$;

and a pharmaceutically acceptable salt, prodrug, or solvate thereof.

More particularly, those compounds disclosed in International PCT Patent Application Publication No. WO 2009/120783 A1, paragraph [0070], including compounds RS-3-15, RS-3-75, and RS-3-19P4 listed in Table 2, are specifically excluded from the presently disclosed compositions of matter, but are not excluded from the presently disclosed methods of use.

In some embodiments of the compounds of Formula (I), $R_1$, $R_4$, $R_5$, $R_6$, and $R_7$ are each independently selected from the group consisting of t-butyl, Cl, Br, methyl, —$OCH_3$, —$NO_2$, —$NH_2$, —OH, —$CH_2OH$, —CHO, —COOH, —$COOCH_3$, —$COOCH_2CH_3$, —$CF_3$, —$CONHCH_3$, —C≡N, —$CONH_2$, H, F, isopropyl, phenyl, cyclohexyl, benzyloxyl, and —$SO_3H$.

In particular embodiments, the compound of Formula (I) is selected from the group consisting of:

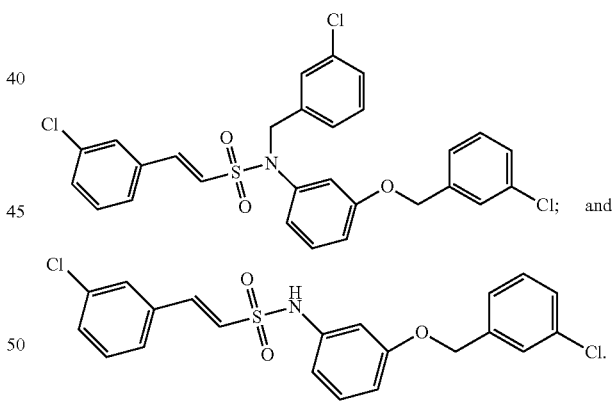

In more particular embodiments, the compound of Formula (I) is selected from the group consisting of:

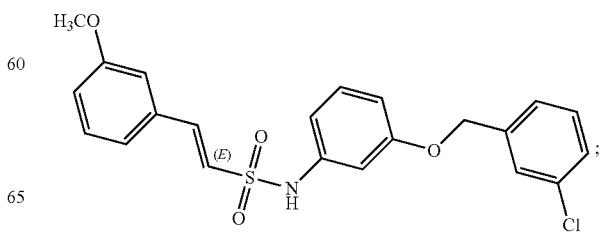

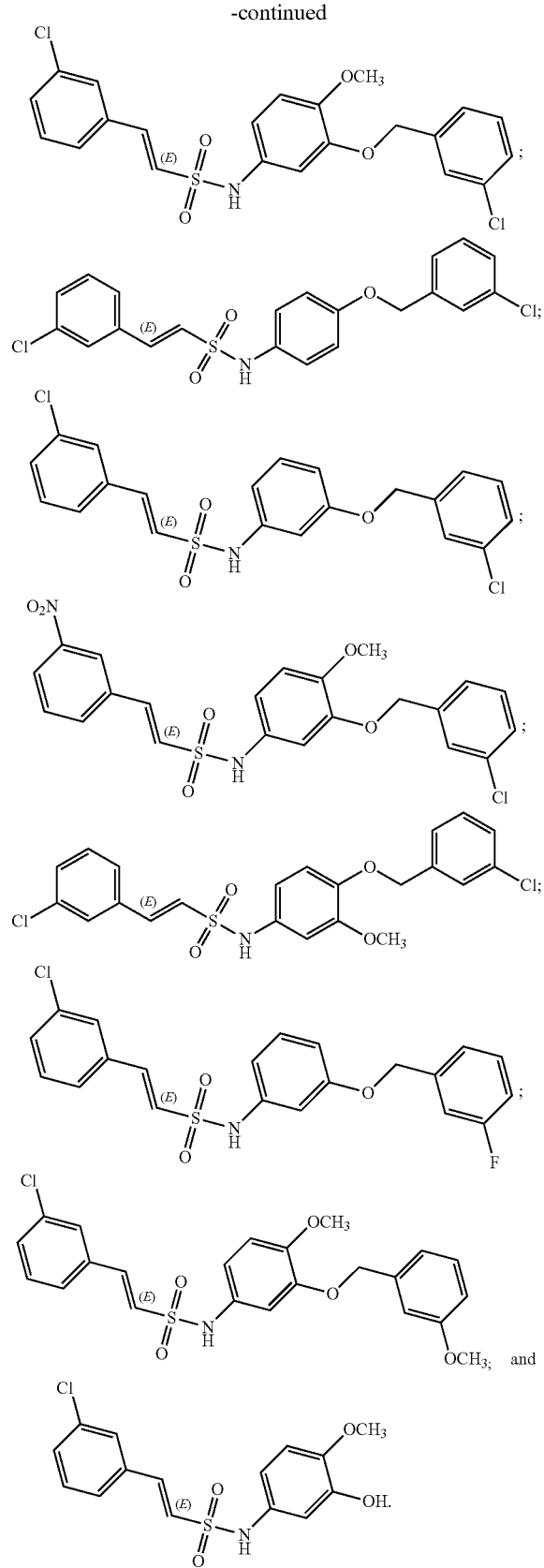

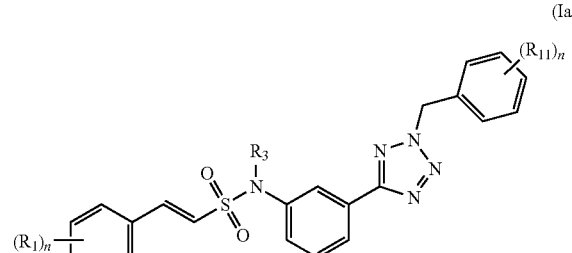

wherein:

each n is independently an integer selected from the group consisting of 0, 1, 2, 3, 4, and 5;

each $R_1$ and $R_{11}$ is independently selected from the group consisting of hydrogen, substituted or unsubstituted alkyl, alkoxyl, hydroxyl, hydroxyalkyl, carboxyl, acyl, including —$COOR_{10}$, wherein $R_{10}$ is lower alkyl, carbonyl, carbamoyl, alkylcarbamoyl, halogen, amino, nitro, nitrile, amide, haloalkyl, aryl, cycloalkyl, aralkyloxyl, and —$SO_3H$; and $R_3$ is selected from the group consisting of: hydrogen, hydroxyl, alkoxyl,

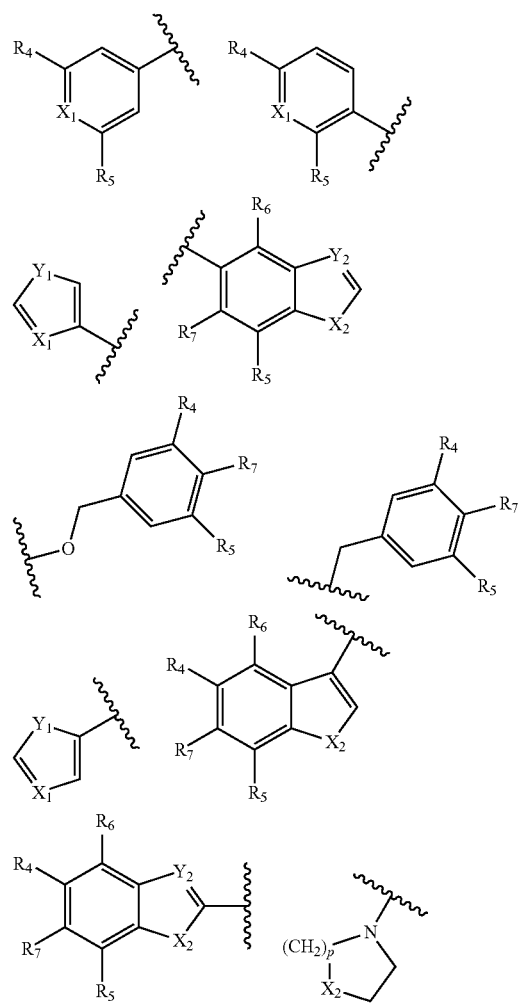

In certain embodiments, the compound of Formula (I) has the following structure:

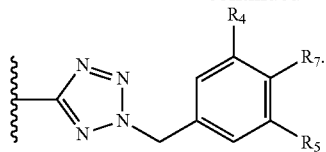

In particular embodiments, the compound of Formula (Ia) is selected from the group consisting of:

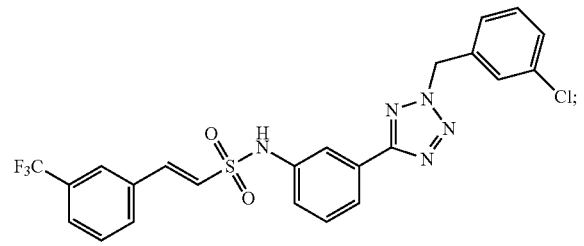

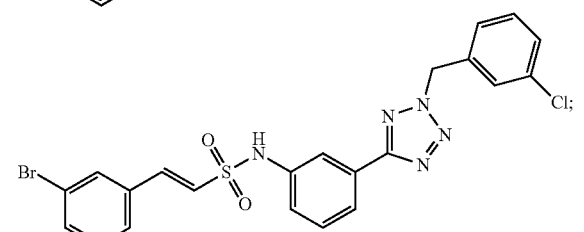

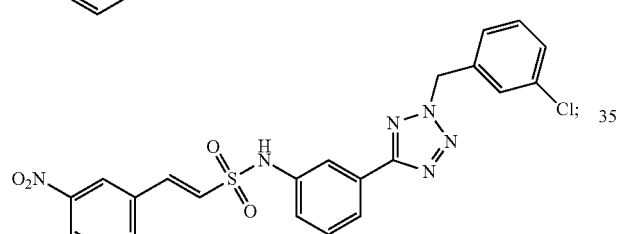

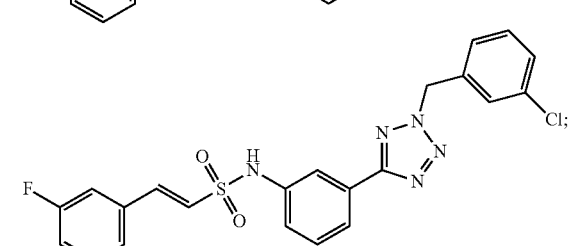

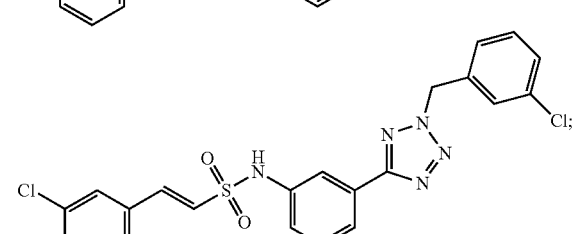

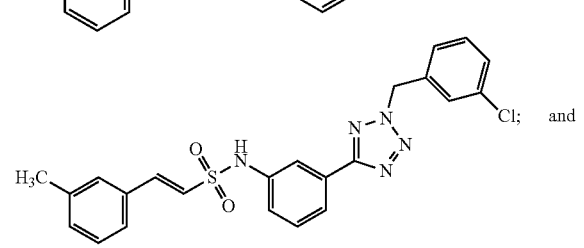

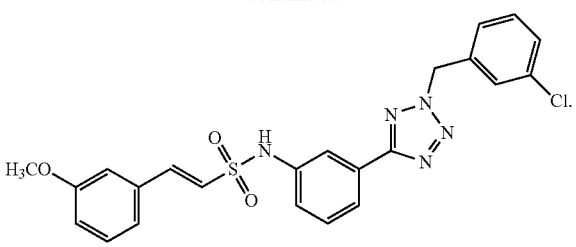

B. Method for Inhibiting a Beta-Lactamase

As used herein, the term "inhibit," and grammatical derivations thereof, refers to the ability of a presently disclosed compound, e.g., a presently disclosed compound of Formula (I) to block, partially block, interfere, decrease, reduce or deactivate a beta lactamase. Thus, one of ordinary skill in the art would appreciate that the term "inhibit" encompasses a complete and/or partial loss of activity of a beta lactamase, e.g., a loss in activity by at least 10%, in some embodiments, a loss in activity by at least 20%, 30%, 50%, 75%, 95%, 98%, and up to and including 100%.

In some embodiments, the presently disclosed subject matter provides a method for inhibiting a beta lactamase, the method comprising contacting the beta lactamase with a compound of Formula (I) in an amount to inhibit the beta lactamase:

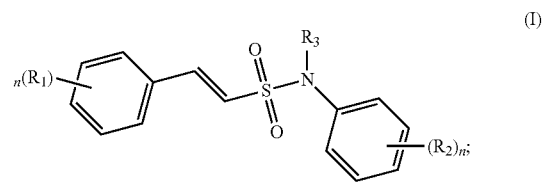

(I)

wherein:

each n is independently an integer selected from the group consisting of 0, 1, 2, 3, 4, and 5;

each $R_2$ and $R_3$ is independently selected from the group consisting of: hydrogen, hydroxyl, alkoxyl,

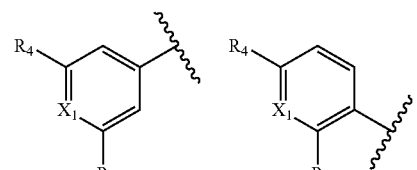

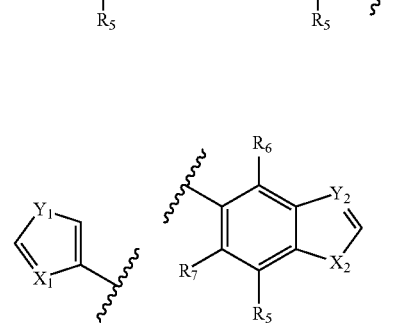

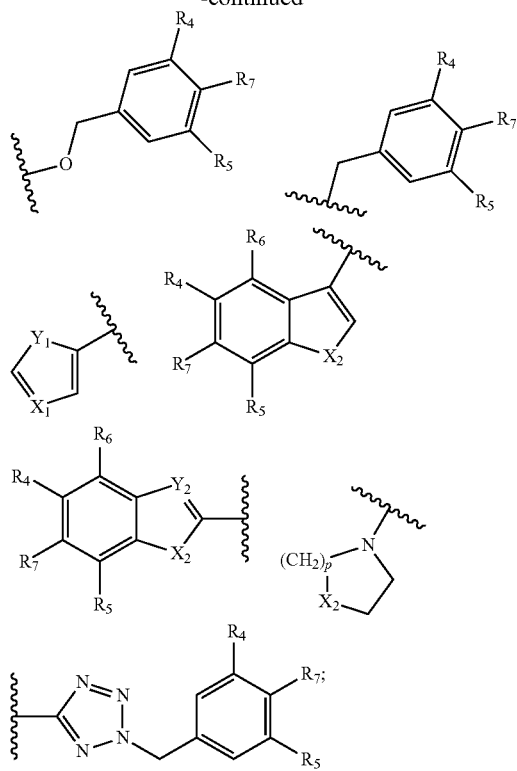

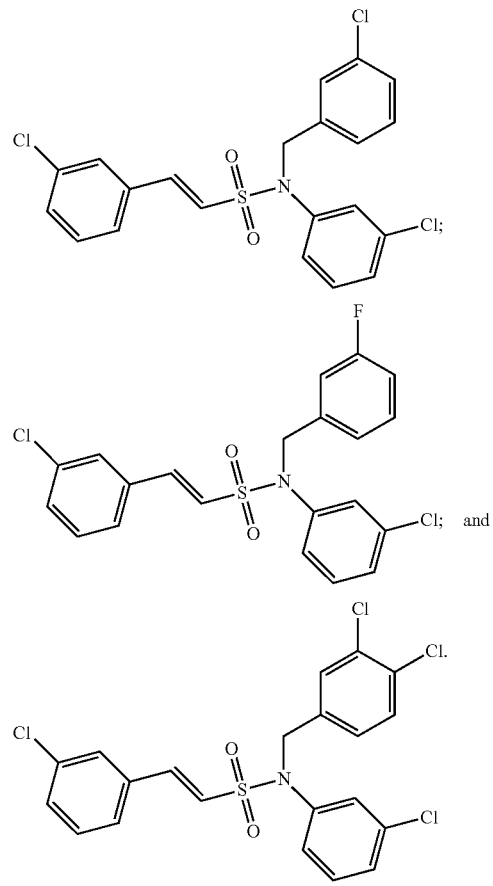

p is an integer selected from the group consisting of 1 and 2;

X₁ is selected from the group consisting of N and CR₈;

X₂ is selected from the group consisting of S, O, NR₈, and CR₈R₉;

Y₁ is selected from the group consisting of S, O, and NR₈;

Y₂ is selected from the group consisting of N and CR₈;

$R_1$, $R_4$, $R_5$, $R_6$, $R_7$, $R_8$, and $R_9$ are each independently selected from the group consisting of hydrogen, substituted or unsubstituted alkyl, alkoxyl, hydroxyl, hydroxyalkyl, carboxyl, acyl, including —COOR₁₀, wherein R₁₀ is lower alkyl, carbonyl, carbamoyl, alkylcarbamoyl, halogen, amino, nitro, nitrile, amide, haloalkyl, aryl, cycloalkyl, aralkyloxyl, and —SO₃H;

and a pharmaceutically acceptable salt, prodrug, or solvate thereof.

In some embodiments of this method, the compound of Formula (I) is selected from the group consisting of:

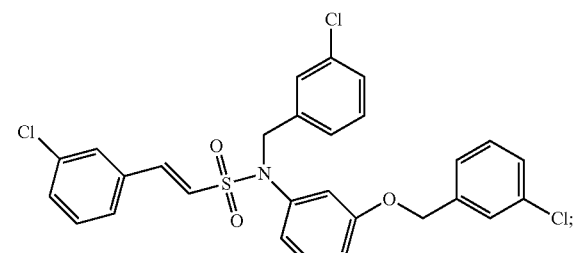

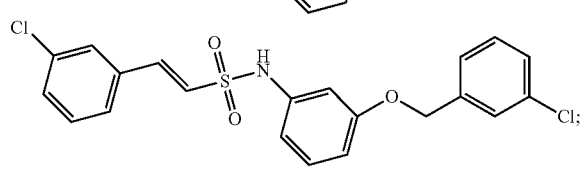

In more particular embodiments, the compound of Formula (I) is selected from the group consisting of:

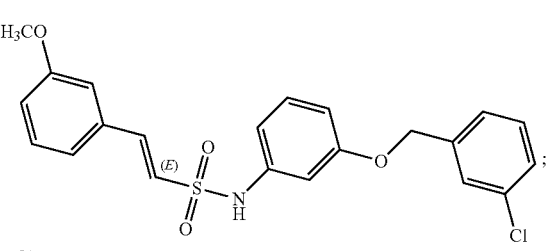

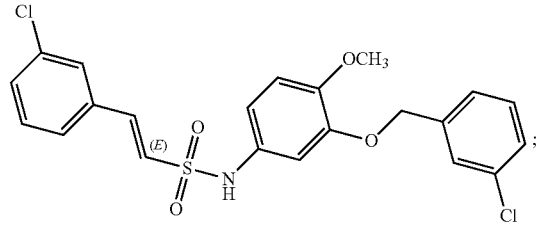

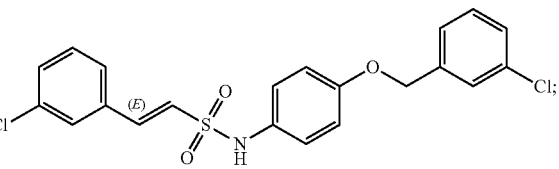

-continued

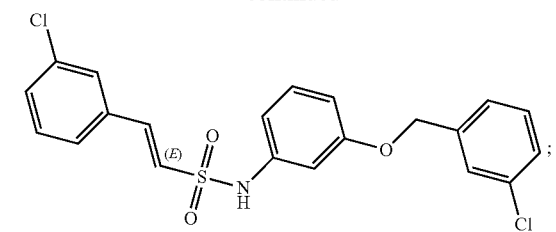

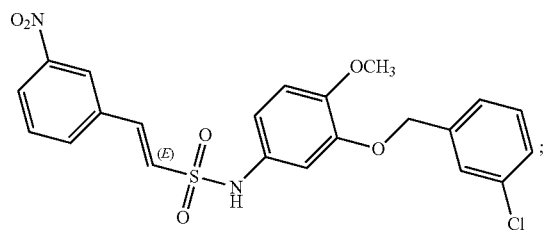

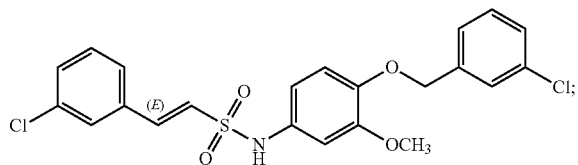

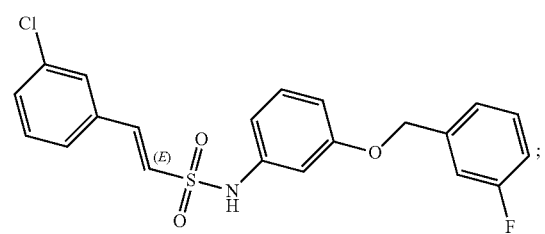

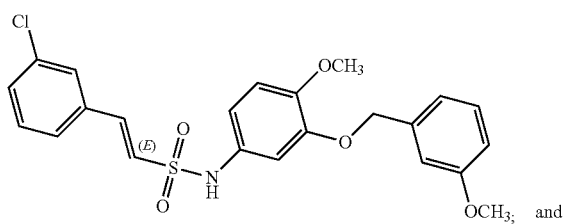

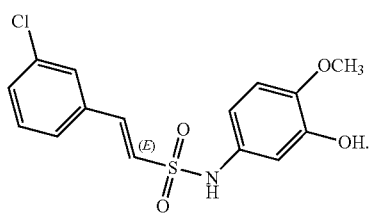 [SMILES: COc1ccc(NS(=O)(=O)/C=C/c2cccc(Cl)c2)cc1O]

In yet other embodiments of the presently disclosed method, the compound of Formula (I) has the following structure:

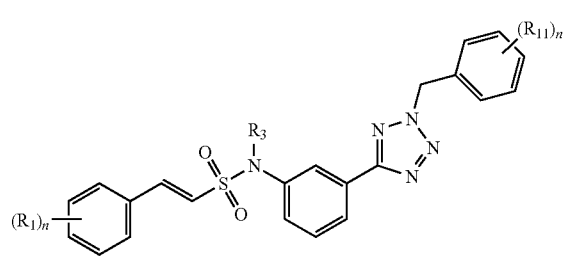

wherein:

each n is independently an integer selected from the group consisting of 0, 1, 2, 3, 4, and 5;

each $R_1$ and $R_{11}$ is independently selected from the group consisting of hydrogen, substituted or unsubstituted alkyl, alkoxyl, hydroxyl, hydroxyalkyl, carboxyl, acyl, including —$COOR_{10}$, wherein $R_{10}$ is lower alkyl, carbonyl, carbamoyl, alkylcarbamoyl, halogen, amino, nitro, nitrile, amide, haloalkyl, aryl, cycloalkyl, aralkyloxyl, and —$SO_3H$; and $R_3$ is selected from the group consisting of: hydrogen, hydroxyl, alkoxyl,

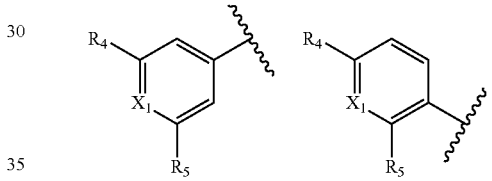

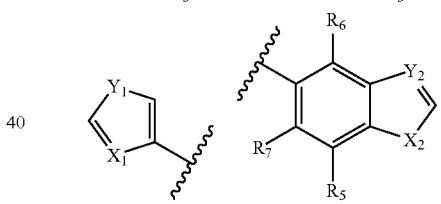

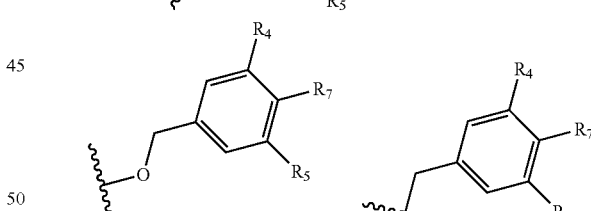

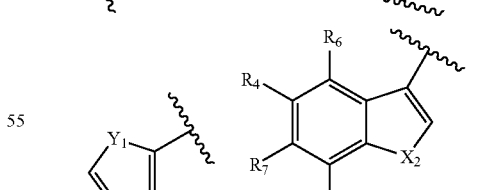

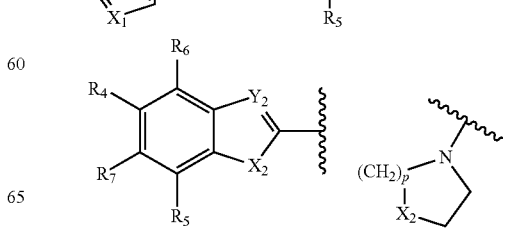

-continued

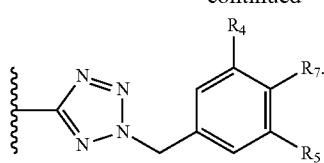

In particular embodiments of the presently disclosed methods, the compound of Formula (Ia) is selected from the group consisting of:

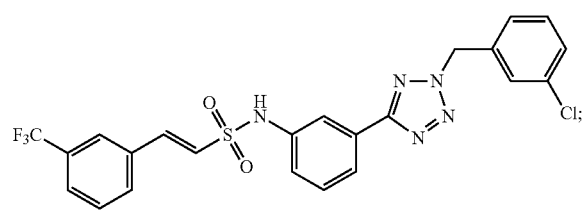

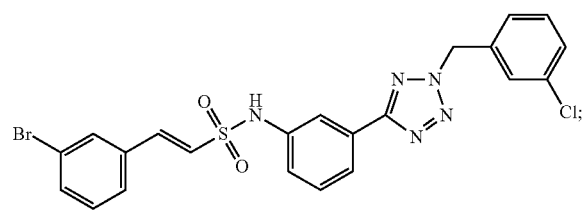

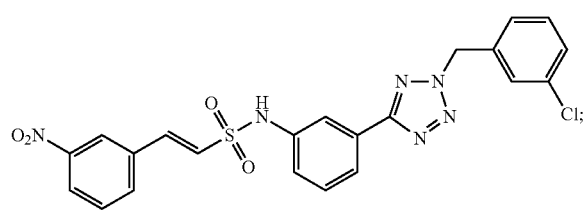

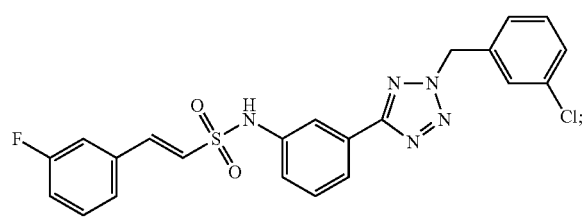

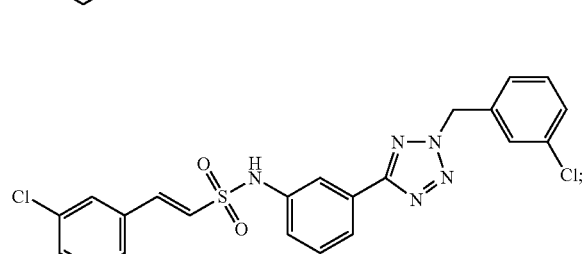

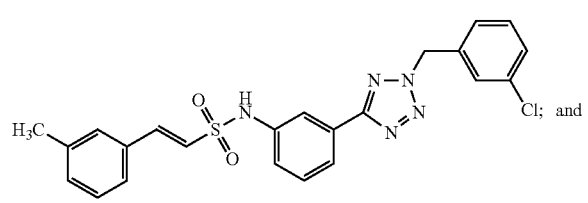

-continued

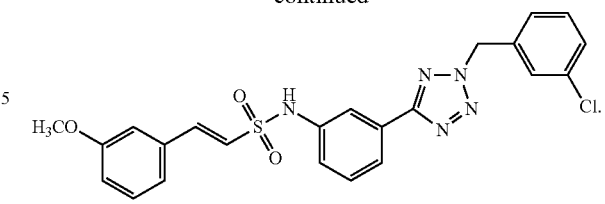

In certain embodiments, the beta-lactamase is selected from the group consisting of a Class A beta-lactamase, a Class B beta-lactamase, a Class C beta-lactamase, and a Class D beta-lactamase. In particular embodiments, the beta-lactamase is a Class A (TEM) beta-lactamase. In other embodiments, the beta-lactamase is a Class C (AmpC) beta-lactamase or a Class B (IMP-1) beta-lactamase.

C. Methods for Treating a Bacterial Infection and Overcoming Antibacterial Resistance As used herein, the term "treating" can include reversing, alleviating, inhibiting the progression of, preventing or reducing the likelihood of the disease, disorder, or condition to which such term applies, or one or more symptoms or manifestations of such disease, disorder or condition. Preventing refers to causing a disease, disorder, condition, or symptom or manifestation of such, or worsening of the severity of such, not to occur. Accordingly, the presently disclosed beta lactamase inhibitors can be administered prophylactically to prevent or reduce the incidence or recurrence of the disease, disorder, or condition.

Accordingly, in some embodiments, the presently disclosed subject matter provides a method for treating a bacterial infection in a subject in need of treatment thereof, the method comprising administering to the subject a therapeutically-effective amount of a beta-lactam antibiotic, optionally in combination with one or more other antibacterial agents, in combination with a therapeutically-effective amount of a compound of Formula (I):

(I)

wherein:

each n is independently an integer selected from the group consisting of 0, 1, 2, 3, 4, and 5;

each $R_2$ and $R_3$ is independently selected from the group consisting of: hydrogen, hydroxyl, alkoxyl,

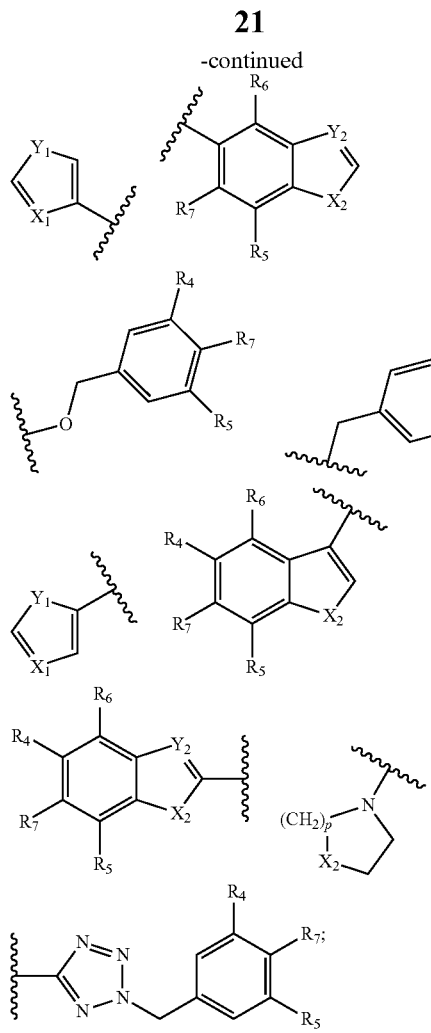

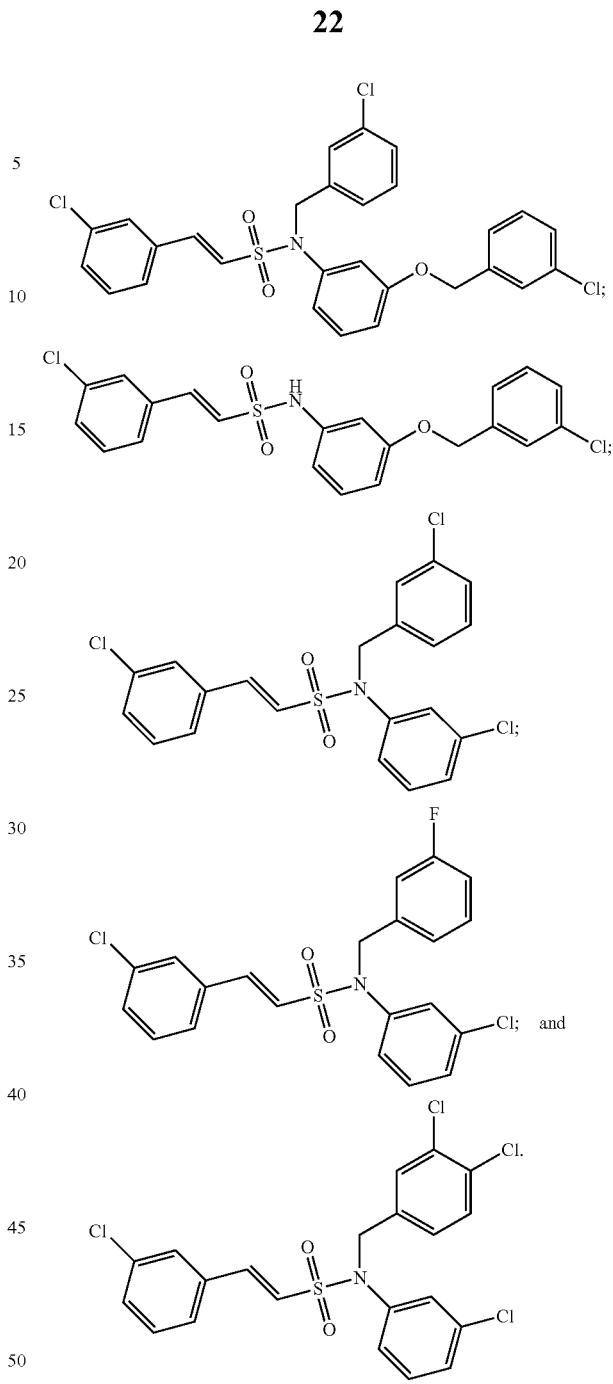

p is an integer selected from the group consisting of 1 and 2;

X₁ is selected from the group consisting of N and CR₈;

X₂ is selected from the group consisting of S, O, NR₈, and CR₈R₉;

Y₁ is selected from the group consisting of S, O, and NR₈;

Y₂ is selected from the group consisting of N and CR₈;

R₁, R₄, R₅, R₆, R₇, R₈, and R₉ are each independently selected from the group consisting of hydrogen, substituted or unsubstituted alkyl, alkoxyl, hydroxyl, hydroxyalkyl, carboxyl, acyl, including —COOR₁₀, wherein R₁₀ is lower alkyl, carbonyl, carbamoyl, alkylcarbamoyl, halogen, amino, nitro, nitrile, amide, haloalkyl, aryl, cycloalkyl, aralkyloxyl, and —SO₃H;

and a pharmaceutically acceptable salt, prodrug, or solvate thereof.

In some embodiments of the presently disclosed methods, R₁, R₄, R₅, R₆, and R₇ are each independently selected from the group consisting of t-butyl, Cl, Br, methyl, —OCH₃, —NO₂, —NH₂, —OH, —CH₂OH, —CHO, —COOH, —COOCH₃, —COOCH₂C H₃, —CF₃, —CONHCH₃, —C≡N, —CONH₂, H, F, isopropyl, phenyl, cyclohexyl, benzyloxyl, and —SO₃H.

In particular embodiments of the presently disclosed methods, the compound of Formula (I) is selected from the group consisting of:

In more particular embodiments, the compound of Formula (I) is selected from the group consisting of:

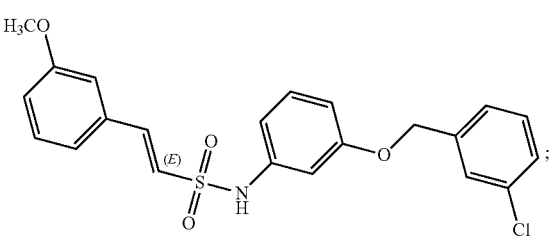

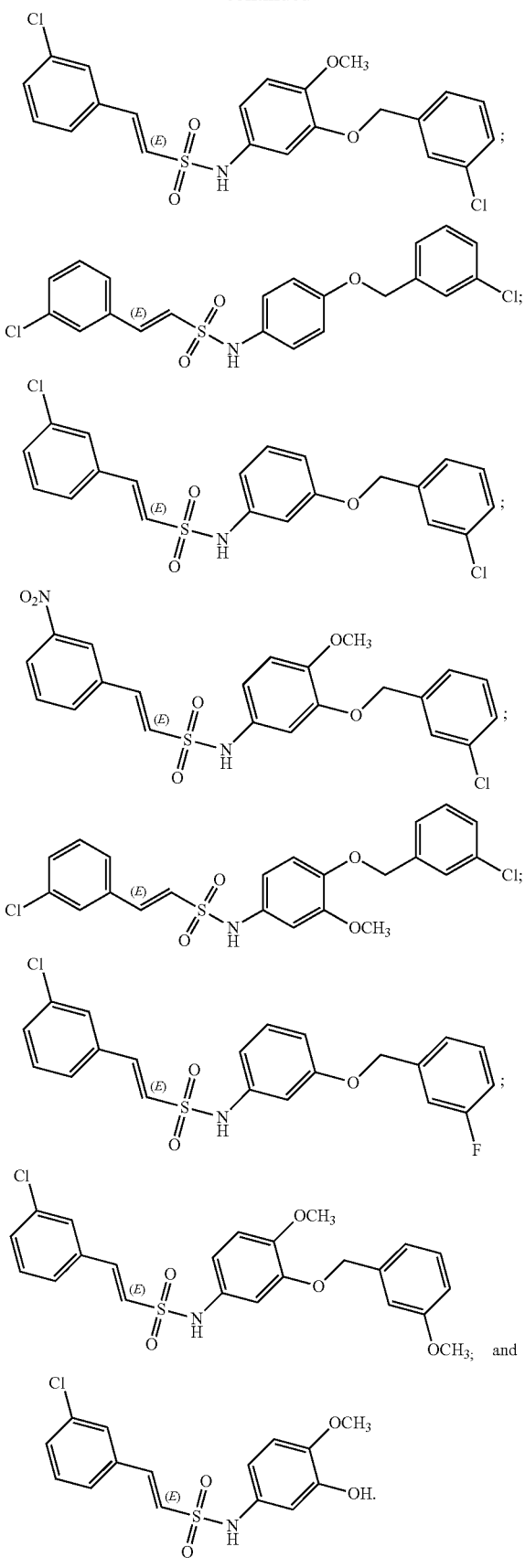

In particular embodiments of the presently disclosed methods, the compound of Formula (I) has the following structure:

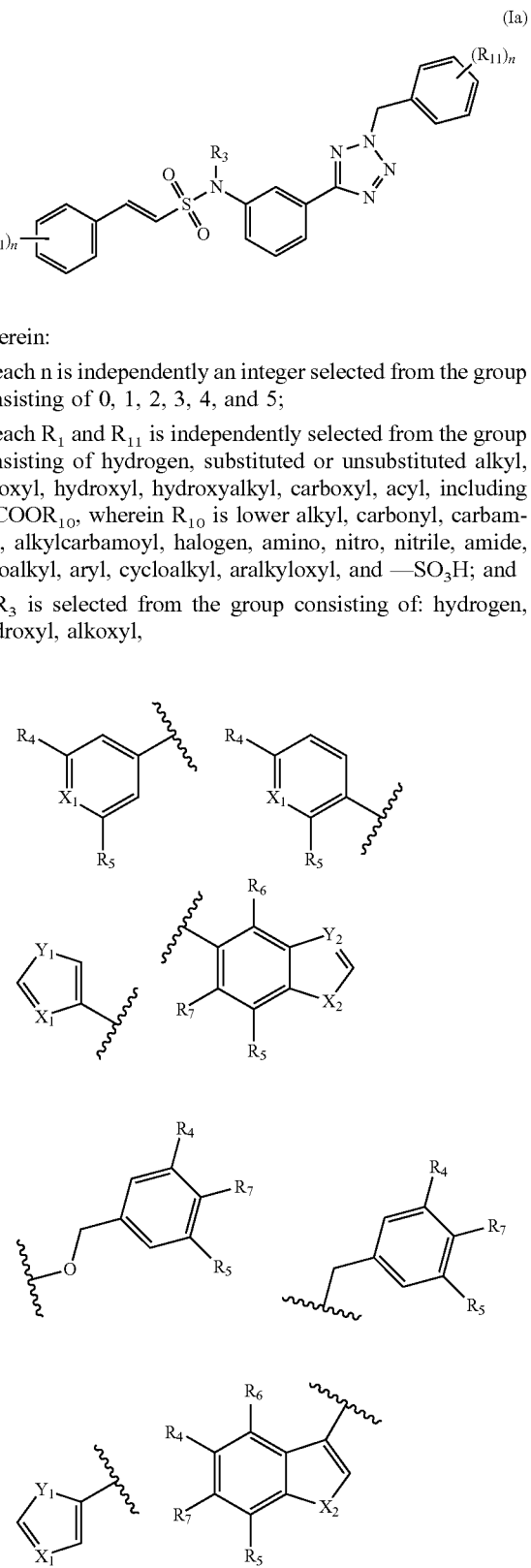

wherein:

each n is independently an integer selected from the group consisting of 0, 1, 2, 3, 4, and 5;

each $R_1$ and $R_{11}$ is independently selected from the group consisting of hydrogen, substituted or unsubstituted alkyl, alkoxyl, hydroxyl, hydroxyalkyl, carboxyl, acyl, including —$COOR_{10}$, wherein $R_{10}$ is lower alkyl, carbonyl, carbamoyl, alkylcarbamoyl, halogen, amino, nitro, nitrile, amide, haloalkyl, aryl, cycloalkyl, aralkyloxyl, and —$SO_3H$; and $R_3$ is selected from the group consisting of: hydrogen, hydroxyl, alkoxyl, -continued

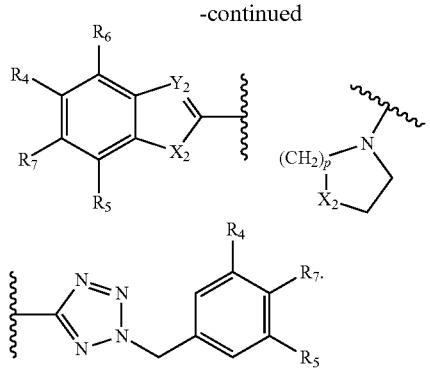

In yet more particular embodiments of the presently disclosed methods, the compound of Formula (Ia) is selected from the group consisting of:

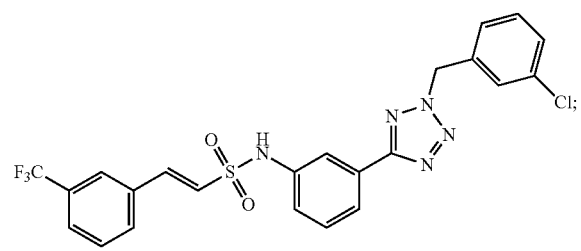

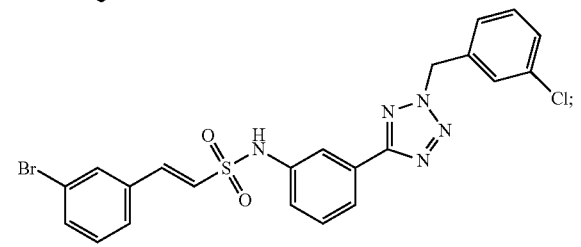

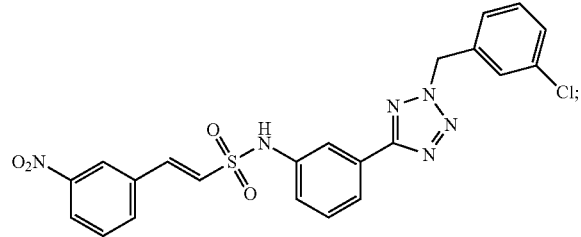

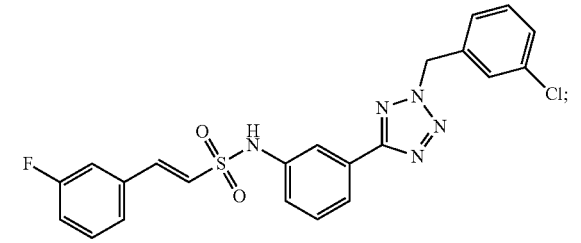

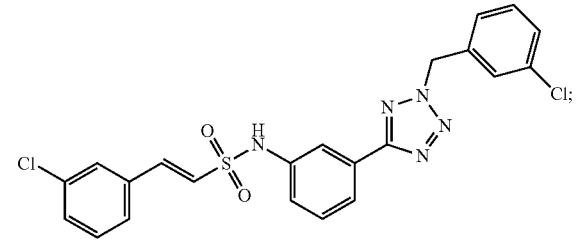

-continued

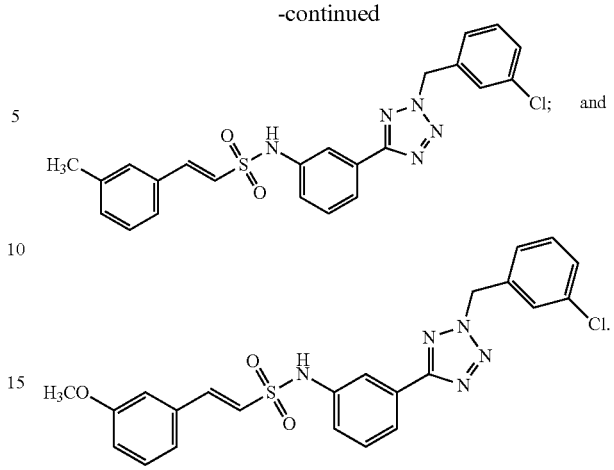

In some embodiments, the one or more other antibacterial agent is selected from the group consisting of a fluoroquinolone, a quinolone, a macrolide, a tetracycline, and combinations thereof. One of ordinary skill in the art would recognize upon review of the presently disclosed subject matter, that any antibacterial agent known in the art could be suitable for use with the presently disclosed methods.

More particularly, beta-lactam antibiotics are compounds having antimicrobial activities and contain the beta-lactam structure. Any beta-lactam antibiotic is suitable for use with the presently disclosed methods. Many suitable beta-lactam antibiotics are known (See e.g., R. B. Morin and M. Gorin, M. Eds.; Academic Press, New York, 1982; vol. 1-3). These beta-lactam antibiotics include, but are not limited to, cephalosporins (e.g., cephalothin), penicillins (e.g., amoxicillin), monobactams (e.g., aztreonam), carbapenems (e.g., imipenem), carbacephems (loracarbef), and others. Beta-lactam antibiotics are effective (in the absence of resistance) against a wide range of bacterial infections.

In particular embodiments, the antibacterial agent is a beta-lactam antibiotic selected from the group consisting of a cephalosporin, a penicillin, a monobactam, a carbapenem, and a carbacephem. Such antibiotics include the following: Carbacephems including, but not limited to, loracarbef. Carbapenems including, but not limited to, ertapenem, doripenem, imipenem/cilastatin, and meropenem. Cephalosporins (first generation) including, but not limited to, cefadroxil, cefazolin, cefalotin or cefalothin, and cefalexin. Cephalosporins (second generation) including, but not limited to, cefaclor, cefamandole, cefoxitin, cefprozil, and cefuroxime. Cephalosporins (third generation) including, but not limited to, cefixime, cefdinir, cefditoren, cefoperazone, cefotaxime, cefpodoxime, ceftazidime, ceftibuten, ceftizoxime, and ceftriaxone. Cephalosporins (fourth generation) including, but not limited to, cefepime. Cephalosporins (fifth generation) including, but not limited to, ceftobiprole. Monobactams including, but not limited to, aztreonam. Penicillins including, but not limited to, amoxicillin, ampicillin, azlocillin, carbenicillin, dicloxacillin, flucloxacillin, mezlocillin, methicillin, nafcillin, oxacillin, penicillin g, penicillin v, piperacillin, temocillin, and ticarcillin. Penicillin combinations including, but not limited to, amoxicillin/clavulanate, ampicillin/sulbactam, piperacillin/tazobactam, ticarcillin/clavulanate.

In certain embodiments, the beta-lactam antibiotic in an antibiotic that is preferentially deactivated by Class A, Class B, and Class C beta-lactamase enzymes, for example, amoxicillin, piperacillin, ampicillin, ceftizoxime, cefotaxime, cefuroxime, cephalexin, cefaclor, cephaloridine, and ceftazidime. Effective doses and modes of administration of beta-lactam antibiotics, alone or in combination with beta-lactamase inhibitor(s), are known in the art or may be determined empirically by one skilled on the art.

In some embodiments the one or more other antibacterial agent is selected from the group consisting of a fluoroquinolone, a quinolone, a macrolide, and a tetracycline. Particular examples of fluoroquinolones include, without limitation, ciprofloxacin, clinafloxacin, enoxacin, fleroxacin, gatifloxacin, moxifloxacin, gemifloxacin, grepafloxacin, levofloxacin, norfloxacin, sparfloxacin, and trovafloxacin. Particular examples of quinolones include, without limitation, cinoxacin, garenoxacin, and nalidixic acid. Particular examples of macrolides include, without limitation, azithromycin, clarithromycin, dirithromycin, erythromycin, and lincomycin. Particular examples of tetracyclines include, without limitation, doxycycline, minocycline, and tetracycline.

Other antibacterial agents suitable for use with the presently disclosed methods include, but are not limited to the following: Aminoglycosides including, but not limited to, amikacin, gentamicin, kanamycin, neomycin, netilmicin, tobramycin, and paromomycin. Ansamycins including, but not limited to, geldanamycin, and herbimycin. Glycopeptides including, but not limited to, teicoplanin, vancomycin, and telavancin. Lincosamides including, but not limited to, clindamycin, and lincomycin. Lipopeptides including, but not limited to, daptomycin. Macrolides including, but not limited to, azithromycin, clarithromycin, dirithromycin, erythromycin, roxithromycin, troleandomycin, telithromycin, and spectinomycin.

Nitrofurans including, but not limited to, furazolidone and nitrofurantoin. Quinolones, including fluoroquinolones, include, but are not limited to, ciprofloxacin, enoxacin, gatifloxacin, levofloxacin, lomefloxacin, moxifloxacin, nalidixic acid, norfloxacin, ofloxacin, trovafloxacin, grepafloxacin, sparfloxacin, and temafloxacin. Sulfonamides including, but not limited to, mafenide, sulfonamidochrysoidine (archaic), sulfacetamide, sulfadiazine, silver sulfadiazine, sulfamethizole, sulfamethoxazole, sulfanilimide (archaic), sulfasalazine, sulfisoxazole, trimethoprim, and trimethoprim-sulfamethoxazole (co-trimoxazole) (tmp-smx). Tetracyclines including, but not limited to, demeclocycline, doxycycline, minocycline, oxytetracycline, and tetracycline.

Drugs against mycobacteria including, but not limited to, clofazimine, dapsone, capreomycin, cycloserine, ethambutol, ethionamide, isoniazid, pyrazinamide, rifampicin (rifampin in us), rifabutin, rifapentine, streptomycin. Polypeptides including, but not limited to, bacitracin, colistin, and polymyxin b. Other antibiotics including, but not limited to, arsphenamine, chloramphenicol, fosfomycin, fusidic acid, linezolid, metronidazole, mupirocin, platensimycin, quinupristin/dalfopristin, rifaximin, thiamphenicol, tigecycline, and timidazole.

Bacterial infections treatable by the presently disclosed methods include, but are not limited to, those caused by gram-positive and/or gram-negative bacteria, for example, bacteria of the genus *Staphylococcus* (such as *Staphylococcus aureus* and *Staphylococcus epidermis*), *Streptococcus* (such as *Streptococcus agalactine, Streptococcus penumoniae* and *Streptococcus faecalis*), *Micrococcus* (such as *Micrococcus luteus*), *Bacillus* (such as *Bacillus subtilis*), *Listerella* (such as *Listerella monocytogenes*), *Escherichia* (such as *Escherichia coli*), *Klebsiella* (such as *Klebsiella pneumoniae*), *Proteus* (such as *Proteus mirabilis* and *Proteus vulgaris*), *Salmonella* (such as *Salmonella typhosa*), *Shigella* (such as *Shigella sonnei*), *Enterobacter* (such as *Enterobacter aerogenes* and *Enterobacterfacium*), *Serratia* (such as *Serratia marcescens*), *Pseudomonas* (such as *Pseudomonas aeruginosa*), *Acinetobacter* such as *Acinetobacter anitratus*), *Nocardia* (such as *Nocardia autotrophica*), or *Mycobacterium* (such as *Mycobacterium fortuitum*).

In further embodiments, the presently disclosed subject matter provides method for overcoming a bacterial resistance in a subject in need of treatment thereof, the method comprising administering to the subject a therapeutically effective amount of a compound of Formula (I) as defined immediately hereinabove.

The "subject" treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein. The term "subject" also refers to an organism, tissue, cell, or collection of cells from a subject.

In general, the "effective amount" of an active agent or drug delivery device refers to the amount necessary to elicit the desired biological response. As will be appreciated by those of ordinary skill in this art, the effective amount of an agent or device may vary depending on such factors as the desired biological endpoint, the agent to be delivered, the makeup of the pharmaceutical composition, the target tissue, and the like.

The term "combination" is used in its broadest sense and means that a subject is administered at least two agents, more particularly a compound of Formula (I) and at least one beta-lactam antibiotic and, optionally, one or more antibacterial agents. More particularly, the term "in combination" refers to the concomitant administration of two (or more) active agents for the treatment of a, e.g., single disease state. As used herein, the active agents may be combined and administered in a single dosage form, may be administered as separate dosage forms at the same time, or may be administered as separate dosage forms that are administered alternately or sequentially on the same or separate days. In one embodiment of the presently disclosed subject matter, the active agents are combined and administered in a single dosage form. In another embodiment, the active agents are administered in separate dosage forms (e.g., wherein it is desirable to vary the amount of one but not the other). The single dosage form may include additional active agents for the treatment of the disease state.

Further, the compounds of Formula (I) described herein can be administered alone or in combination with adjuvants that enhance stability of the inhibitors, facilitate administration of pharmaceutical compositions containing them in certain embodiments, provide increased dissolution or dispersion, increase inhibitory activity, provide adjunct therapy, and the like, including other active ingredients. Advantageously, such combination therapies utilize lower dosages of the conventional therapeutics, thus avoiding possible toxicity and adverse side effects incurred when those agents are used as monotherapies.

The timing of administration of a compound of Formula (I) and at least one additional therapeutic agent can be varied so long as the beneficial effects of the combination of these agents are achieved. Accordingly, the phrase "in combination with" refers to the administration of a compound of Formula (I) and at least one additional therapeutic agent either simultaneously, sequentially, or a combination thereof. Therefore, a subject administered a combination of a compound of Formula (I) and at least one additional therapeutic agent can receive compound of Formula (I) and at least one additional therapeutic agent at the same time (i.e., simultaneously) or at different times (i.e., sequentially, in either order, on the same day or on different days), so long as the effect of the combination of both agents is achieved in the subject.

When administered sequentially, the agents can be administered within 1, 5, 10, 30, 60, 120, 180, 240 minutes or longer of one another. In other embodiments, agents administered sequentially, can be administered within 1, 5, 10, 15, 20 or more days of one another. Where the compound of Formula (I) and at least one additional therapeutic agent are administered simultaneously, they can be administered to the subject as separate pharmaceutical compositions, each comprising either a compound of Formula (I) or at least one additional therapeutic agent, or they can be administered to a subject as a single pharmaceutical composition comprising both agents.

When administered in combination, the effective concentration of each of the agents to elicit a particular biological response may be less than the effective concentration of each agent when administered alone, thereby allowing a reduction in the dose of one or more of the agents relative to the dose that would be needed if the agent was administered as a single agent. The effects of multiple agents may, but need not be, additive or synergistic. The agents may be administered multiple times.

In some embodiments, when administered in combination, the two or more agents can have a synergistic effect. As used herein, the terms "synergy," "synergistic," "synergistically" and derivations thereof, such as in a "synergistic effect" or a "synergistic combination" or a "synergistic composition" refer to circumstances under which the biological activity of a combination of a compound of Formula (I) and at least one additional therapeutic agent is greater than the sum of the biological activities of the respective agents when administered individually.

Synergy can be expressed in terms of a "Synergy Index (SI)," which generally can be determined by the method described by F. C. Kull et al. Applied Microbiology 9, 538 (1961), from the ratio determined by:

$$Q_a/Q_A + Q_b/Q_B = \text{Synergy Index (SI)}$$

wherein:

$Q_A$ is the concentration of a component A, acting alone, which produced an end point in relation to component A;

$Q_a$ is the concentration of component A, in a mixture, which produced an end point;

$Q_B$ is the concentration of a component B, acting alone, which produced an end point in relation to component B; and $Q_b$ is the concentration of component B, in a mixture, which produced an end point.

Generally, when the sum of $Q_a/Q_A$ and $Q_b/Q_B$ is greater than one, antagonism is indicated. When the sum is equal to one, additivity is indicated. When the sum is less than one, synergism is demonstrated. The lower the SI, the greater the synergy shown by that particular mixture. Thus, a "synergistic combination" has an activity higher that what can be expected based on the observed activities of the individual components when used alone. Further, a "synergistically effective amount" of a component refers to the amount of the component necessary to elicit a synergistic effect in, for example, another therapeutic agent present in the composition.

D. Pharmaceutical Compositions and Administration

In another aspect, the presently disclosed subject matter provides a pharmaceutical composition including one or more compounds of Formula (I) alone or in combination with one or more additional therapeutic agents in admixture with a pharmaceutically acceptable excipient.

More particularly, the presently disclosed subject matter provides a pharmaceutical composition comprising a compound of Formula (I) and a pharmaceutically acceptable carrier. In particular embodiments, the pharmaceutical composition comprises a compound of Formula (I), one or more antibacterial agents, and a pharmaceutically acceptable carrier. In yet more particular embodiments, the antibacterial agent is selected from the group consisting of a beta-lactam antibiotic, a fluoroquinolone, a quinolone, a macrolide, a tetracycline, and combinations thereof.

In certain embodiments, the beta-lactam antibiotic is selected from the group consisting of a cephalosporin, a penicillin, a monobactam, a carbapenem, and a carbacephem. In more certain embodiments, the beta-lactam antibiotic is selected from the group consisting of loracarbef, ertapenem, doripenem, imipenem/cilastatin, meropenem, cefadroxil, cefazolin, cefalotin or cefalothin, cefalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftobiprole, aztreonam, amoxicillin, ampicillin, azlocillin, carbenicillin, dicloxacillin, flucloxacillin, mezlocillin, methicillin, nafcillin, oxacillin, penicillin g, penicillin v, piperacillin, temocillin, ticarcillin, amoxicillin/clavulanate, ampicillin/sulbactam, piperacillin/tazobactam, and ticarcillin/clavulanate.

In some embodiments, the fluoroquinolone is selected from the group consisting of ciprofloxacin, clinafloxacin, enoxacin, fleroxacin, gatifloxacin, moxifloxacin, gemifloxacin, grepafloxacin, levofloxacin, norfloxacin, sparfloxacin, and trovafloxacin. In some embodiments, the quinolone is selected from the group consisting of cinoxacin, garenoxacin, and nalidixic acid. In further embodiments, the macrolide is selected from the group consisting of azithromycin, clarithromycin, dirithromycin, erythromycin, lincomycin, roxithromycin, troleandomycin, telithromycin, and spectinomycin. In yet further embodiments, the tetracycline is selected from the group consisting of demeclocycline, doxycycline, minocycline, oxytetracycline, and tetracycline.

One of skill in the art will recognize that the pharmaceutical compositions include the pharmaceutically acceptable salts of the compounds described above. Pharmaceutically acceptable salts are generally well known to those of ordinary skill in the art, and include salts of active compounds which are prepared with relatively nontoxic acids or bases, depending on the particular substituent moieties found on the compounds described herein. When compounds of the present disclosure contain relatively acidic functionalities, base addition salts can be obtained by contacting the neutral form of such compounds with a sufficient amount of the desired base, either neat or in a suitable inert solvent.

Examples of pharmaceutically acceptable base addition salts include sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like {see, for example, Berge et al, "Pharmaceutical Salts", Journal of Pharmaceutical Science, 1977, 66, 1-19). Certain specific compounds of the present disclosure contain both basic and acidic functionalities that allow the compounds to be converted into either base or acid addition salts.

Accordingly, pharmaceutically acceptable salts suitable for use with the presently disclosed subject matter include, by way of example but not limitation, acetate, benzenesulfonate, besylate, benzoate, bicarbonate, bitartrate, bromide, calcium edetate, carnsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrate, or teoclate. Other pharmaceutically acceptable salts may be found in, for example, Remington: The Science and Practice of Pharmacy ($20^{th}$ ed.) Lippincott, Williams & Wilkins (2000).

In therapeutic and/or diagnostic applications, the compounds of the disclosure can be formulated for a variety of modes of administration, including systemic and topical or localized administration. Techniques and formulations generally may be found in Remington: The Science and Practice of Pharmacy ($20^{th}$ ed.) Lippincott, Williams & Wilkins (2000).

Depending on the specific conditions being treated, such agents may be formulated into liquid or solid dosage forms and administered systemically or locally. The agents may be delivered, for example, in a timed- or sustained-slow release form as is known to those skilled in the art. Techniques for formulation and administration may be found in Remington: The Science and Practice of Pharmacy ($20^{th}$ ed.) Lippincott, Williams & Wilkins (2000). Suitable routes may include oral, buccal, by inhalation spray, sublingual, rectal, transdermal, vaginal, transmucosal, nasal or intestinal administration; parenteral delivery, including intramuscular, subcutaneous, intramedullary injections, as well as intrathecal, direct intraventricular, intravenous, intra-articullar, intrasternal, intra-synovial, intra-hepatic, intralesional, intracranial, intraperitoneal, intranasal, or intraocular injections or other modes of delivery.

For injection, the agents of the disclosure may be formulated and diluted in aqueous solutions, such as in physiologically compatible buffers such as Hank's solution, Ringer's solution, or physiological saline buffer. For such transmucosal administration, penetrants appropriate to the barrier to be permeated are used in the formulation. Such penetrants are generally known in the art.

Use of pharmaceutically acceptable inert carriers to formulate the compounds herein disclosed for the practice of the disclosure into dosages suitable for systemic administration is within the scope of the disclosure. With proper choice of carrier and suitable manufacturing practice, the compositions of the present disclosure, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the disclosure to be formulated as tablets, pills, capsules, liquids, gels, syrups, slurries, suspensions and the like, for oral ingestion by a subject (e.g., patient) to be treated.

For nasal or inhalation delivery, the agents of the disclosure also may be formulated by methods known to those of skill in the art, and may include, for example, but not limited to, examples of solubilizing, diluting, or dispersing substances, such as saline; preservatives, such as benzyl alcohol; absorption promoters; and fluorocarbons.

Pharmaceutical compositions suitable for use in the present disclosure include compositions wherein the active ingredients are contained in an effective amount to achieve its intended purpose. Determination of the effective amounts is well within the capability of those skilled in the art, especially in light of the detailed disclosure provided herein. Generally, the compounds according to the disclosure are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. A non-limiting dosage is 10 to 30 mg per day. The exact dosage will depend upon the route of administration, the form in which the compound is administered, the subject to be treated, the body weight of the subject to be treated, and the preference and experience of the attending physician.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

Pharmaceutical preparations for oral use can be obtained by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethyl-cellulose (CMC), and/or polyvinylpyrrolidone (PVP: povidone). If desired, disintegrating agents may be added, such as the cross-linked polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols (PEGs). In addition, stabilizers may be added.

II. Definitions

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

While the following terms in relation to compounds of Formula (I) are believed to be well understood by one of ordinary skill in the art, the following definitions are set forth to facilitate explanation of the presently disclosed subject matter. These definitions are intended to supplement and illustrate, not preclude, the definitions that would be apparent to one of ordinary skill in the art upon review of the present disclosure.

The terms substituted, whether preceded by the term "optionally" or not, and substituent, as used herein, refer to the ability, as appreciated by one skilled in this art, to change one functional group for another functional group on a molecule, provided that the valency of all atoms is maintained. When more than one position in any given structure may be substituted with more than one substituent selected from a specified group, the substituent may be either the same or different at every position. The substituents also may be further substituted (e.g., an aryl group substituent may have another substituent off it, such as another aryl group, which is further substituted at one or more positions).

Where substituent groups or linking groups are specified by their conventional chemical formulae, written from left to right, they equally encompass the chemically identical substituents that would result from writing the structure from right to left, e.g., —CH$_2$O— is equivalent to —OCH$_2$—; —C(=O)O— is equivalent to —OC(=O)—; —OC(=O)NR— is equivalent to —NRC(=O)O—, and the like.

When the term "independently selected" is used, the substituents being referred to (e.g., R groups, such as groups R$_1$, R$_2$, and the like, or variables, such as "m" and "n"), can be identical or different. For example, both R$_1$ and R$_2$ can be substituted alkyls, or R$_1$ can be hydrogen and R$_2$ can be a substituted alkyl, and the like.

The terms "a," "an," or "a(n)," when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

A named "R" or group will generally have the structure that is recognized in the art as corresponding to a group having that name, unless specified otherwise herein. For the purposes of illustration, certain representative "R" groups as set forth above are defined below.

Description of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

Unless otherwise explicitly defined, a "substituent group," as used herein, includes a functional group selected from one or more of the following moieties, which are defined herein:

The term hydrocarbon, as used herein, refers to any chemical group comprising hydrogen and carbon. The hydrocarbon may be substituted or unsubstituted. As would be known to one skilled in this art, all valencies must be satisfied in making any substitutions. The hydrocarbon may be unsaturated, saturated, branched, unbranched, cyclic, polycyclic, or heterocyclic. Illustrative hydrocarbons are further defined herein below and include, for example, methyl, ethyl, n-propyl, iso-propyl, cyclopropyl, allyl, vinyl, n-butyl, tert-butyl, ethynyl, cyclohexyl, methoxyl, diethylamino, and the like.

The term "alkyl," by itself or as part of another substituent, means, unless otherwise stated, a straight (i.e., unbranched) or branched chain, acyclic or cyclic hydrocarbon group, or combination thereof, which may be fully saturated, mono- or polyunsaturated and can include di- and multivalent groups, having the number of carbon atoms designated (i.e., $C_1$-$C_{10}$ means one to ten carbons, including 1, 2, 3, 4, 5, 6, 7, 8, 9, and 10 carbons). In particular embodiments, the term "alkyl" refers to $C_{1-20}$ inclusive, including 1, 2, 3, 4, 5, 6, 7, 8, 9, 10, 11, 12, 13, 14, 15, 16, 17, 18, 19, and 20 carbons, linear (i.e., "straight-chain"), branched, or cyclic, saturated or at least partially and in some cases fully unsaturated (i.e., alkenyl and alkynyl) hydrocarbon radicals derived from a hydrocarbon moiety containing between one and twenty carbon atoms by removal of a single hydrogen atom.

Representative saturated hydrocarbon groups include, but are not limited to, methyl, ethyl, n-propyl, isopropyl, n-butyl, isobutyl, sec-butyl, tert-butyl, n-pentyl, sec-pentyl, isopentyl, neopentyl, n-hexyl, sec-hexyl, n-heptyl, n-octyl, n-decyl, n-undecyl, dodecyl, cyclohexyl, (cyclohexyl)methyl, cyclopropylmethyl, and homologs and isomers thereof.

"Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "heteroalkyl," by itself or in combination with another term, means, unless otherwise stated, a stable straight or branched chain, or cyclic hydrocarbon group, or combinations thereof, consisting of at least one carbon atoms and at least one heteroatom selected from the group consisting of O, N, P, Si and S, and wherein the nitrogen, phosphorus, and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. Examples include, but are not limited to, $—CH_2—CH_2—O—CH_3$, $—CH_2—CH_2—NH—CH_3$, $—CH_2—CH_2—N(CH_3)—CH_3$, $—CH_2—S—CH_2—CH_3$, $—CH_2—CH_{25}—S(O)—CH_3$, $—CH_2—CH_2—S(O)_2—CH_3$, $—CH=CH—O—CH_3$, $—Si(CH_3)_3$, $—CH_2—CH=N—OCH_3$, $—CH=CH—N(CH_3)—CH_3$, $O—CH_3$, $—O—CH_2—CH_3$, and $—CN$. Up to two or three heteroatoms may be consecutive, such as, for example, $—CH_2—NH—OCH_3$ and $—CH_2—O—Si(CH_3)_3$.

As described above, heteroalkyl groups, as used herein, include those groups that are attached to the remainder of the molecule through a heteroatom, such as $—C(O)R'$, $—C(O)NR'$, $—NR'R''$, $—OR'$, $—SR$, $—S(O)R$, and/or $—S(O_2)R'$. Where "heteroalkyl" is recited, followed by recitations of specific heteroalkyl groups, such as $—NR'R$ or the like, it will be understood that the terms heteroalkyl and $—NR'R''$ are not redundant or mutually exclusive. Rather, the specific heteroalkyl groups are recited to add clarity. Thus, the term "heteroalkyl" should not be interpreted herein as excluding specific heteroalkyl groups, such as $—NR'R''$ or the like.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl, and fused ring systems, such as dihydro- and tetrahydronaphthalene, and the like.

The term "cycloalkylalkyl," as used herein, refers to a cycloalkyl group as defined hereinabove, which is attached to the parent molecular moiety through an alkyl group, also as defined above. Examples of cycloalkylalkyl groups include cyclopropylmethyl and cyclopentylethyl.

The terms "cycloheteroalkyl" or "heterocycloalkyl" refer to a non-aromatic ring system, unsaturated or partially unsaturated ring system, such as a 3- to 10-member substituted or unsubstituted cycloalkyl ring system, including one or more heteroatoms, which can be the same or different, and are selected from the group consisting of nitrogen (N), oxygen (O), sulfur (S), phosphorus (P), and silicon (Si), and optionally can include one or more double bonds.

The cycloheteroalkyl ring can be optionally fused to or otherwise attached to other cycloheteroalkyl rings and/or non-aromatic hydrocarbon rings. Heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocylic refers to a non-aromatic 5-, 6-, or 7-membered ring or a polycyclic group wherein at least one ring atom is a heteroatom selected from O, S, and N (wherein the nitrogen and sulfur heteroatoms may be optionally oxidized), including, but not limited to, a bi- or tri-cyclic group, comprising fused six-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Representative cycloheteroalkyl ring systems include, but are not limited to pyrrolidinyl, pyrrolinyl, imidazolidinyl, imidazolinyl, pyrazolidinyl, pyrazolinyl, piperidyl, piperazinyl, indolinyl, quinuclidinyl, morpholinyl, thiomorpholinyl, thiadiazinanyl, tetrahydrofuranyl, and the like.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The terms "cycloalkylene" and "heterocycloalkylene" refer to the divalent derivatives of cycloalkyl and heterocycloalkyl, respectively.

An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Alkyl groups which are limited to hydrocarbon groups are termed "homoalkyl."

More particularly, the term "alkenyl" as used herein refers to a monovalent group derived from a $C_{1-20}$ inclusive straight or branched hydrocarbon moiety having at least one carbon-carbon double bond by the removal of a single hydrogen atom. Alkenyl groups include, for example, ethenyl (i.e., vinyl), propenyl, butenyl, 1-methyl-2-buten-1-yl, pentenyl, hexenyl, octenyl, and butadienyl.

The term "cycloalkenyl" as used herein refers to a cyclic hydrocarbon containing at least one carbon-carbon double bond. Examples of cycloalkenyl groups include cyclopropenyl, cyclobutenyl, cyclopentenyl, cyclopentadiene, cyclohexenyl, 1,3-cyclohexadiene, cycloheptenyl, cycloheptatrienyl, and cyclooctenyl.

The term "alkynyl" as used herein refers to a monovalent group derived from a straight or branched $C_{1-20}$ hydrocarbon of a designed number of carbon atoms containing at least one carbon-carbon triple bond. Examples of "alkynyl" include ethynyl, 2-propynyl (propargyl), 1-propynyl, pentynyl, hexynyl, heptynyl, and allenyl groups, and the like.

The term "alkylene" by itself or a part of another substituent refers to a straight or branched bivalent aliphatic hydrocarbon group derived from an alkyl group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—CH$_2$—); ethylene (—CH$_2$—CH$_2$—); propylene (—(CH$_2$)$_3$—); cyclohexylene (—C$_6$H$_{10}$—); —CH═CH—CH═CH—; —CH═CH—CH$_2$—; —CH$_2$CH$_2$CH$_2$CH$_2$—, —CH$_2$CH═CHCH$_2$—, —CH$_2$CsCCH$_2$—, —CH$_2$CH$_2$CH (CH$_2$CH$_2$CH$_3$)CH$_2$—,         —(CH$_2$)$_q$—N(R)—(CH$_2$)$_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—CH$_2$—O—); and ethylenedioxyl (—O—(CH$_2$)$_2$—O—). An alkylene group can have about 2 to about 3 carbon atoms and can further have 6-20 carbons. Typically, an alkyl (or alkylene) group will have from 1 to 24 carbon atoms, with those groups having 10 or fewer carbon atoms being some embodiments of the present disclosure. A "lower alkyl" or "lower alkylene" is a shorter chain alkyl or alkylene group, generally having eight or fewer carbon atoms.

The term "heteroalkylene" by itself or as part of another substituent means a divalent group derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula —C(O)OR'— represents both —C(O)OR'— and —R'OC(O)—.

The term "aryl" means, unless otherwise stated, an aromatic hydrocarbon substituent that can be a single ring or multiple rings (such as from 1 to 3 rings), which are fused together or linked covalently. The term "heteroaryl" refers to aryl groups (or rings) that contain from one to four heteroatoms (in each separate ring in the case of multiple rings) selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of above noted aryl and heteroaryl ring systems are selected from the group of acceptable substituents described below. The terms "arylene" and "heteroarylene" refer to the divalent forms of aryl and heteroaryl, respectively.

For brevity, the term "aryl" when used in combination with other terms (e.g., aryloxo, arylthioxo, arylalkyl) includes both aryl and heteroaryl rings as defined above. Thus, the terms "arylalkyl" and "heteroarylalkyl" are meant to include those groups in which an aryl or heteroaryl group is attached to an alkyl group (e.g., benzyl, phenethyl, pyridylmethyl, furylmethyl, and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). However, the term "haloaryl," as used herein is meant to cover only aryls substituted with one or more halogens.

Where a heteroalkyl, heterocycloalkyl, or heteroaryl includes a specific number of members (e.g. "3 to 7 membered"), the term "member" refers to a carbon or heteroatom.

Further, a structure represented generally by the formula:

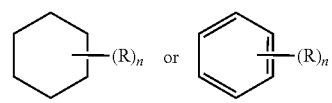

as used herein refers to a ring structure, for example, but not limited to a 3-carbon, a 4-carbon, a 5-carbon, a 6-carbon, a 7-carbon, and the like, aliphatic and/or aromatic cyclic compound, including a saturated ring structure, a partially saturated ring structure, and an unsaturated ring structure, comprising a substituent R group, wherein the R group can be present or absent, and when present, one or more R groups can each be substituted on one or more available carbon atoms of the ring structure. The presence or absence of the R group and number of R groups is determined by the value of the variable "n," which is an integer generally having a value ranging from 0 to the number of carbon atoms on the ring available for substitution. Each R group, if more than one, is substituted on an available carbon of the ring structure rather than on another R group. For example, the structure above where n is 0 to 2 would comprise compound groups including, but not limited to:

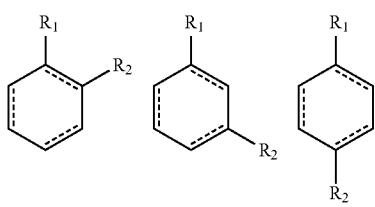

and the like.

A dashed line representing a bond in a cyclic ring structure indicates that the bond can be either present or absent in the ring. That is, a dashed line representing a bond in a cyclic ring structure indicates that the ring structure is selected from the group consisting of a saturated ring structure, a partially saturated ring structure, and an unsaturated ring structure.

The symbol ( ⁓⁓⁓ ) denotes the point of attachment of a moiety to the remainder of the molecule.

When a named atom of an aromatic ring or a heterocyclic aromatic ring is defined as being "absent," the named atom is replaced by a direct bond.

Each of above terms (e.g., "alkyl," "heteroalkyl," "cycloalkyl, and "heterocycloalkyl", "aryl," "heteroaryl," "phosphonate," and "sulfonate" as well as their divalent derivatives) are meant to include both substituted and unsubstituted forms of the indicated group. Optional substituents for each type of group are provided below.

Substituents for alkyl, heteroalkyl, cycloalkyl, heterocycloalkyl monovalent and divalent derivative groups (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R'", —OC(O)R', —C(O)R', —CO$_2$R', —C(O)NR'R", —OC(O)NR'R", —NR"C(O)R', —NR'—C(O)NR"R'", —NR"C(O)OR', —NR—C(NR'R"R'")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such groups. R', R'", R'" and R"" each may independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. As used herein, an "alkoxy" group is an alkyl attached to the remainder of the molecule through a divalent oxygen. When a compound of the disclosure includes more than one R group, for example, each of the R groups is independently selected as are each R', R", R'" and R"" groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for alkyl groups above, exemplary substituents for aryl and heteroaryl groups (as well as their divalent derivatives) are varied and are selected from, for example: halogen, —OR', —NR'R", —SR', —SiR'R"R'", —OC(O)R', —C(O)R', —CO$_2$R', —C(O)NR'R", —OC(O)NR'R", —NR"C(O)R', —NR'—C(O)NR"R'", —NR"C(O)OR', —NR—C(NR'R"R'")=NR'", —NR—C(NR'R")=NR'"—S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxo, and fluoro(C$_1$-C$_4$)alkyl, in a number ranging from zero to the total number of open valences on aromatic ring system; and where R', R", R'" and R"" may be independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the disclosure includes more than one R group, for example, each of the R groups is independently selected as are each R', R", R'" and R"" groups when more than one of these groups is present.

Two of the substituents on adjacent atoms of aryl or heteroaryl ring may optionally form a ring of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4.

One of the single bonds of the new ring so formed may optionally be replaced with a double bond. Alternatively, two of the substituents on adjacent atoms of aryl or heteroaryl ring may optionally be replaced with a substituent of the formula —(CRR')$_s$—X'—(C"R'")$_d$—, where s and d are independently integers of from 0 to 3, and X' is —O—, —NR'—, —S—, —S(O)—, —S(O)$_2$—, or —S(O)$_2$NR'—. The substituents R, R', R" and R'" may be independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "acyl" refers to an organic acid group wherein the —OH of the carboxyl group has been replaced with another substituent and has the general formula RC(=O)—, wherein R is an alkyl, alkenyl, alkynyl, aryl, carbocylic, heterocyclic, or aromatic heterocyclic group as defined herein). As such, the term "acyl" specifically includes arylacyl groups, such as an acetylfuran and a phenacyl group. Specific examples of acyl groups include acetyl and benzoyl. Acyl groups also are intended to include amides, —RC(=O)NR', esters, —RC(=O)OR', ketones, —RC(=O)R', and aldehydes, —RC(=O)H.

The terms "alkoxyl" or "alkoxy" are used interchangeably herein and refer to a saturated (i.e., alkyl-O—) or unsaturated (i.e., alkenyl-O— and alkynyl-O—) group attached to the parent molecular moiety through an oxygen atom, wherein the terms "alkyl," "alkenyl," and "alkynyl" are as previously described and can include C$_{1-20}$ inclusive, linear, branched, or cyclic, saturated or unsaturated oxo-hydrocarbon chains, including, for example, methoxyl, ethoxyl, propoxyl, isopropoxyl, n-butoxyl, sec-butoxyl, t-butoxyl, and n-pentoxyl, neopentoxyl, n-hexoxyl, and the like.

The term "alkoxyalkyl" as used herein refers to an alkyl-O-alkyl ether, for example, a methoxyethyl or an ethoxymethyl group.

"Aryloxyl" refers to an aryl-O— group wherein the aryl group is as previously described, including a substituted aryl. The term "aryloxyl" as used herein can refer to phenyloxyl or hexyloxyl, and alkyl, substituted alkyl, halo, or alkoxyl substituted phenyloxyl or hexyloxyl.

"Aralkyl" refers to an aryl-alkyl-group wherein aryl and alkyl are as previously described, and included substituted aryl and substituted alkyl. Exemplary aralkyl groups include benzyl, phenylethyl, and naphthylmethyl.

"Aralkyloxyl" refers to an aralkyl-O— group wherein the aralkyl group is as previously described. An exemplary aralkyloxyl group is benzyloxyl, i.e., $C_6H_5$—$CH_2$—O—. An aralkyloxyl group can optionally be substituted.

"Alkoxycarbonyl" refers to an alkyl-O—C(=O)— group. Exemplary alkoxycarbonyl groups include methoxycarbonyl, ethoxycarbonyl, butyloxycarbonyl, and t-butyloxycarbonyl.

"Aryloxycarbonyl" refers to an aryl-O—C(=O)— group. Exemplary aryloxycarbonyl groups include phenoxy- and naphthoxy-carbonyl.

"Aralkoxycarbonyl" refers to an aralkyl-O—C(=O)— group. An exemplary aralkoxycarbonyl group is benzyloxycarbonyl.

"Carbamoyl" refers to an amide group of the formula —C(=O)$NH_2$. "Alkylcarbamoyl" refers to a R'RN—C(=O)— group wherein one of R and R' is hydrogen and the other of R and R' is alkyl and/or substituted alkyl as previously described. "Dialkylcarbamoyl" refers to a R'RN—C(=O)— group wherein each of R and R' is independently alkyl and/or substituted alkyl as previously described.

The term carbonyldioxyl, as used herein, refers to a carbonate group of the formula —O—C(=O)—OR.

"Acyloxyl" refers to an acyl-O— group wherein acyl is as previously described.

The term "amino" refers to the —$NH_2$ group and also refers to a nitrogen containing group as is known in the art derived from ammonia by the replacement of one or more hydrogen radicals by organic radicals. For example, the terms "acylamino" and "alkylamino" refer to specific N-substituted organic radicals with acyl and alkyl substituent groups respectively.

An "aminoalkyl" as used herein refers to an amino group covalently bound to an alkylene linker. More particularly, the terms alkylamino, dialkylamino, and trialkylamino as used herein refer to one, two, or three, respectively, alkyl groups, as previously defined, attached to the parent molecular moiety through a nitrogen atom. The term alkylamino refers to a group having the structure —NHR' wherein R' is an alkyl group, as previously defined; whereas the term dialkylamino refers to a group having the structure —NR'R", wherein R' and R" are each independently selected from the group consisting of alkyl groups. The term trialkylamino refers to a group having the structure —NR'R"R'", wherein R', R", and R'" are each independently selected from the group consisting of alkyl groups. Additionally, R', R", and/or R'" taken together may optionally be —$(CH_2)_k$— where k is an integer from 2 to 6. Examples include, but are not limited to, methylamino, dimethylamino, ethylamino, diethylamino, diethylaminocarbonyl, methylethylamino, iso-propylamino, piperidino, trimethylamino, and propylamino The amino group is —NR'R", wherein R' and R" are typically selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

The terms alkylthioether and thioalkoxyl refer to a saturated (i.e., alkyl-S—) or unsaturated (i.e., alkenyl-S— and alkynyl-S—) group attached to the parent molecular moiety through a sulfur atom. Examples of thioalkoxyl moieties include, but are not limited to, methylthio, ethylthio, propylthio, isopropylthio, n-butylthio, and the like.

"Acylamino" refers to an acyl-NH— group wherein acyl is as previously described. "Aroylamino" refers to an aroyl-NH— group wherein aroyl is as previously described.

The term "carbonyl" refers to the —C(=O)— group, and can include an aldehyde group represented by the general formula R—C(=O)H.

The term "carboxyl" refers to the —COOH group. Such groups also are referred to herein as a "carboxylic acid" moiety.

The terms "halo," "halide," or "halogen" as used herein refer to fluoro, chloro, bromo, and iodo groups. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "hydroxyl" refers to the —OH group.

The term "hydroxyalkyl" refers to an alkyl group substituted with an —OH group.

The term "mercapto" refers to the —SH group.

The term "oxo" as used herein means an oxygen atom that is double bonded to a carbon atom or to another element.

The term "nitro" refers to the —$NO_2$ group.

The term "thio" refers to a compound described previously herein wherein a carbon or oxygen atom is replaced by a sulfur atom.

The term "sulfate" refers to the —$SO_4$ group.

The term thiohydroxyl or thiol, as used herein, refers to a group of the formula —SH.

More particularly, the term "sulfide" refers to compound having a group of the formula —SR.

The term "sulfone" refers to compound having a sulfonyl group —S($O_2$)R.

The term "sulfoxide" refers to a compound having a sulfinyl group —S(O)R The term ureido refers to a urea group of the formula —NH—CO—$NH_2$.

Throughout the specification and claims, a given chemical formula or name shall encompass all tautomers, congeners, and optical- and stereoisomers, as well as racemic mixtures where such isomers and mixtures exist.

Certain compounds of the present disclosure may possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The compounds of the present disclosure do not include those which are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefenic bonds or other centers of geometric asymmetry, and unless specified otherwise, it is intended that the compounds include both E and Z geometric isomers.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

It will be apparent to one skilled in the art that certain compounds of this disclosure may exist in tautomeric forms, all such tautomeric forms of the compounds being within the scope of the disclosure. The term "tautomer," as used herein, refers to one of two or more structural isomers which exist in equilibrium and which are readily converted from one isomeric form to another.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this disclosure.

The compounds of the present disclosure may also contain unnatural proportions of atomic isotopes at one or more of atoms that constitute such compounds. For example, the compounds may be radiolabeled with radioactive isotopes, such as for example tritium ($^{3}H$), iodine-125 ($^{125}I$) or carbon-14 ($^{14}C$). All isotopic variations of the compounds of the present disclosure, whether radioactive or not, are encompassed within the scope of the present disclosure.

The compounds of the present disclosure may exist as salts. The present disclosure includes such salts. Examples of applicable salt forms include hydrochlorides, hydrobromides, sulfates, methanesulfonates, nitrates, maleates, acetates, citrates, fumarates, tartrates (e.g. (+)-tartrates, (−)-tartrates or mixtures thereof including racemic mixtures, succinates, benzoates and salts with amino acids such as glutamic acid. These salts may be prepared by methods known to those skilled in art. Also included are base addition salts such as sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the present disclosure contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

In addition to salt forms, the present disclosure provides compounds, which are in a prodrug form. Prodrugs of the compounds described herein are those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

Inhibition Assay

The inhibition of beta lactamase was determined spectrophotometrically. Beta lactamase activity was followed by measuring the change in absorbance upon hydrolysis of nitrocefin, [3-(2,4-dinitrostyryl)-(6R,7R)-7-(2-thienylacetamido)-ceph-3-em-4-carboxylic acid, E-isomer], (Calbiochem, San Diego, Calif., USA) at 486 nm. Inhibition constants (Ki) for the inhibitors are obtained at the desired temperature and solvent conditions by measuring the rate of substrate hydrolysis at increasing amounts of inhibitors. All inhibition assays were performed at 25° C. in 50 mM sodium phosphate, 5% DMSO, pH 7.0, keeping the enzyme concentration at 5 nM and the substrate concentration at 167 µM. Reaction was started by addition of substrate to the corresponding mixture of enzyme and inhibitor preincubated for 10 minutes.

Example 2

TABLE 2

Inhibition of TEM-1 β-lactamase, Drug Resistant Mutants and AmpC β-lactamase

| Compound | R₁ | R₂ | R₃ | TEM-1 (WT) | TEM-12 (R164S) | TEM-17 (E104K) | TEM-30 (R244S) | TEM-40 (M69I) | AmpC | Average Ki [nM] |
|---|---|---|---|---|---|---|---|---|---|---|
| ef-rs-08-052 | Cl | 3-chlorobenzyloxy | 3-chlorobenzyl | 250 ± 32 | 78 | 111 | 293 | 72 | 67 | 145 |
| ef-rs-05-076 | CF₃ | (1-(3-chlorobenzyl)tetrazol-5-yl) | H | 49 ± 8 | 31 | 8.4 | 884 | 5.3 | 80 | 176 |
| ef-rs-04-090 | Cl | 3-chlorobenzyloxy | H | 102 ± 11 | 676 | 101 | 463 | 94 | 528 | 327 |
| ef-rs-05-049 | Br | (1-(3-chlorobenzyl)tetrazol-5-yl) | H | 78 ± 3.2 | 53 | 70 | 1740 | 49 | 182 | 362 |
| ef-rs-03-075 | Cl | Cl | 3-chlorobenzyl | 82 ± 12 | nd | nd | nd | nd | nd |  |

(All Ki values in nM; structure: R1-substituted styryl-sulfonamide with N-R3 and aryl-R2 substituent, general formula shown above table.)

TABLE 2-continued

Inhibition of TEM-1 β-lactamase, Drug Resistant Mutants and AmpC β-lactamase

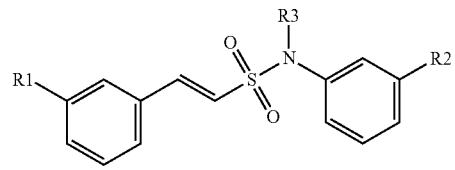

| Compound | R₁ | R₂ | R₃ | TEM-1 (WT) | TEM-12 (R164S) | TEM-17 (E104K) | TEM-30 (R244S) | TEM-40 (M69I) | Amp C | Average Ki [nM] |
|---|---|---|---|---|---|---|---|---|---|---|
| ef-rs-05-075 | NO₂ | 5-(3-chlorobenzyl)tetrazol-2-yl | H | 106 ± 22 | nd | nd | nd | nd | nd | |
| ef-rs-05-077 | F | 5-(3-chlorobenzyl)tetrazol-2-yl | H | 116 ± 27 | nd | nd | nd | nd | nd | |
| ef-rs-05-047 | Cl | 5-(3-chlorobenzyl)tetrazol-2-yl | H | 130 ± 18 | nd | nd | nd | nd | nd | |
| ef-rs-08-057 | Cl | Cl | 3-fluoro-5-isobutylphenyl | 177 ± 32 | nd | nd | nd | nd | nd | |
| ef-rs-08-051 | Cl | Cl | 3,4-dichloro-5-isobutylphenyl | 268 ± 34 | nd | nd | nd | nd | nd | | nd: not determined

Example 3

Biochemical Data of Representative β-Lactamase Inhibitors

TABLE 3

Biochemical Data of Representative β-lactamase Inhibitors

| Compound | Structure | CLogP | Solubility (μM) | $T_{1/2}$ (min) | HSA Kd (nM) | TEM-1 (nM) | TEM-1 ΔH (kcal/mol) |
|---|---|---|---|---|---|---|---|
| ef-rs-05-054 | 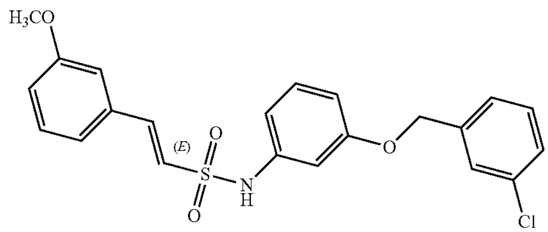 [SMILES: COc1cccc(/C=C/S(=O)(=O)Nc2cccc(OCc3cccc(Cl)c3)c2)c1] | 5.50 | 6.0 | 59 ± 6 | 97.5 ± 8.6<br>202 ± 37 | 53 ± 9 | +2.32 |
| ef-rs-04-091 | 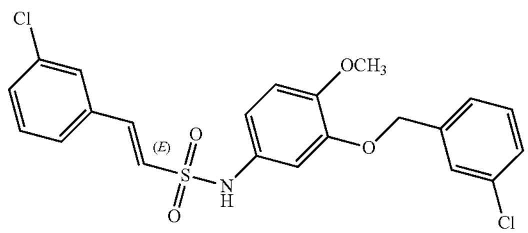 [SMILES: COc1ccc(NS(=O)(=O)/C=C/c2cccc(Cl)c2)cc1OCc1cccc(Cl)c1] | 5.96 | 19 | 70 ± 8 | 4080 ± 360<br>4260 ± 430 | 85 ± 11 | +1.75 |
| ef-rs-09-030 | 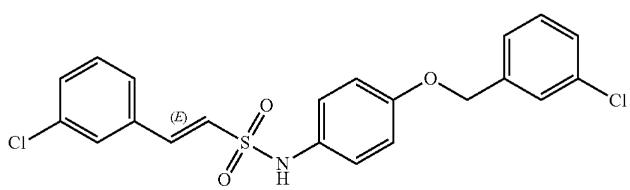 [SMILES: O=S(=O)(/C=C/c1cccc(Cl)c1)Nc1ccc(OCc2cccc(Cl)c2)cc1] | 5.71 | 6.0 | | 301 ± 65 | 85 ± 21 | |
| ef-rs-08-048 | 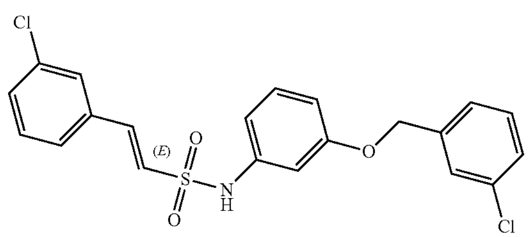 | 6.30 | 19 | 120 ± 10 | 113 ± 8<br>252 ± 66 | 102 ± 11 | +1.62 |
| ef-rs-05-080 | 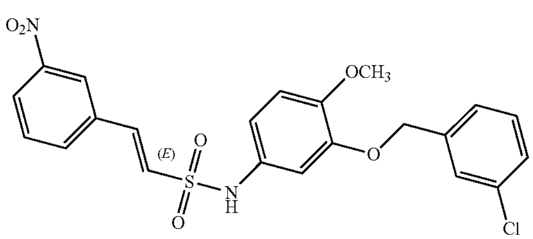 [SMILES: COc1ccc(NS(=O)(=O)/C=C/c2cccc([N+](=O)[O-])c2)cc1OCc1cccc(Cl)c1] | 4.99 | 3.0 | 37 ± 4 | 4580 ± 210<br>5350 ± 870 | 194 ± 8 | +2.64 |
| ef-rs-09-029 | 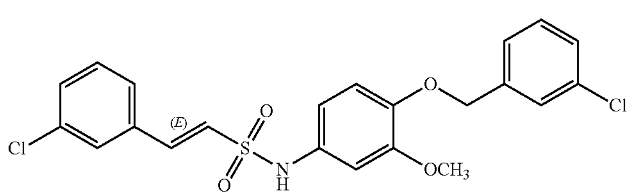 [SMILES: COc1cc(NS(=O)(=O)/C=C/c2cccc(Cl)c2)ccc1OCc1cccc(Cl)c1] | 5.58 | 8.0 | | 484 ± 76 | 406 ± 77 | |

TABLE 3-continued

Biochemical Data of Representative β-lactamase Inhibitors

| Compound | Structure | CLogP | Solubility (µM) | $T_{1/2}$ (min) | HSA Kd (nM) | TEM-1 (nM) | TEM-1 ΔH (kcal/mol) |
|---|---|---|---|---|---|---|---|
| ef-rs-09-012 | 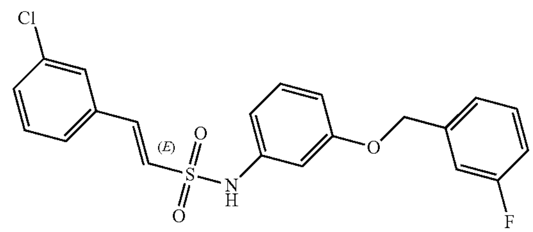 | 5.31 | 7.0 | 81 ± 14 | 49 ± 5 / 52 ± 4 | 523 ± 84 | +2.67 |
| ef-rs-09-018 | 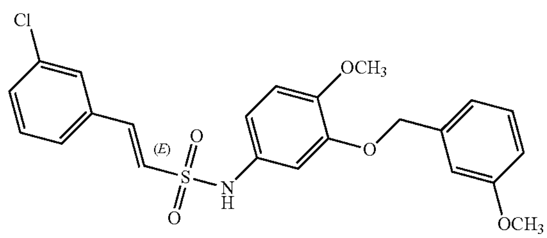 [SMILES: COc1cccc(COc2cc(NS(=O)(=O)/C=C/c3cccc(Cl)c3)ccc2OC)c1] | 4.9 | 50 | 22 ± 6 | 348 ± 53 | 702 ± 91 | +0.62 |
| ef-rs-09-014 | 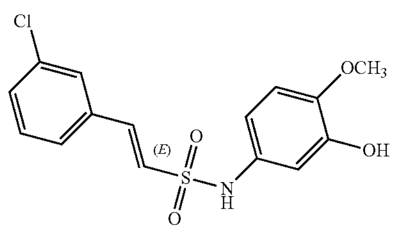 [SMILES: COc1ccc(NS(=O)(=O)/C=C/c2cccc(Cl)c2)cc1O] | 3.03 | 450 | <5 | 2510 ± 1780 | 2470 ± 50 | +0.92 |

TABLE 4

Biochemical Data of Representative β-lactamase Inhibitors

| Compound | Structure | TEM-12 (R164S) (nM) | TEM-17 (E104K) (nM) | TEM-30 (R244S) (nM) | TEM-40 (M691) (nM) |
|---|---|---|---|---|---|
| ef-rs-05-054 | 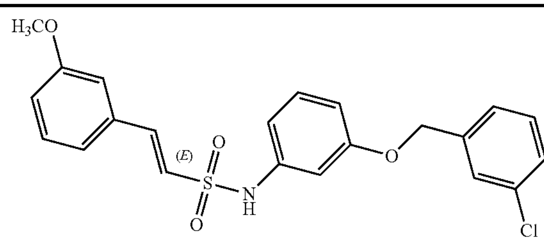 | 480 ± 20 | 114 ± 14 | 1040 ± 230 | 224 ± 29 |
| ef-rs-04-091 | 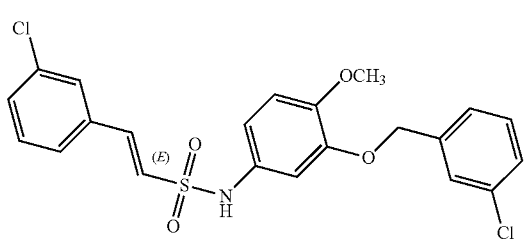 [SMILES: COc1ccc(NS(=O)(=O)/C=C/c2cccc(Cl)c2)cc1OCc1cccc(Cl)c1] | 360 ± 40 | 188 ± 21 | 2000 ± 190 | 215 ± 60 |

TABLE 4-continued

Biochemical Data of Representative β-lactamase Inhibitors

| Compound | Structure | TEM-12 (R164S) (nM) | TEM-17 (E104K) (nM) | TEM-30 (R244S) (nM) | TEM-40 (M691) (nM) |
|---|---|---|---|---|---|
| ef-rs-09-030 | 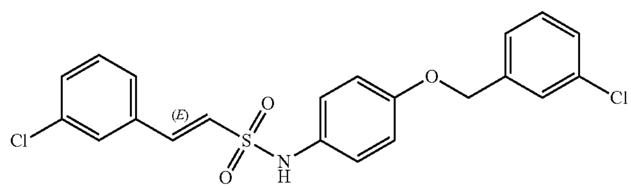 [SMILES: O=S(=O)(/C=C/c1cccc(Cl)c1)Nc1ccc(OCc2cccc(Cl)c2)cc1] | | | | |
| ef-rs-08-048 | 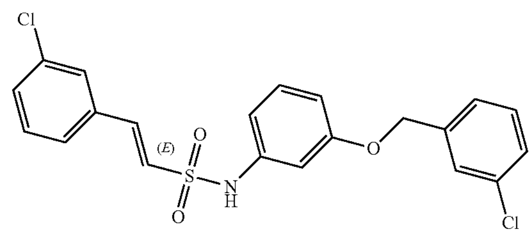 | 679 ± 59 | 99 ± 15 | 463 ± 70 | 85 ± 16 |
| ef-rs-05-080 | 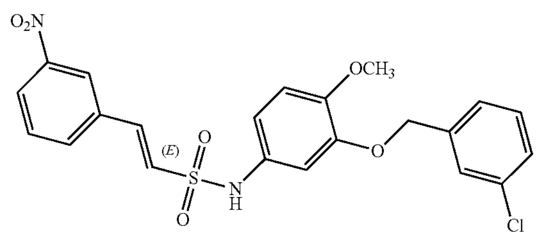 [SMILES: COc1ccc(NS(=O)(=O)/C=C/c2cccc([N+](=O)[O-])c2)cc1OCc1cccc(Cl)c1] | 319 ± 45 | 101 ± 25 | 2490 ± 340 | 219 ± 32 |
| ef-rs-09-029 | 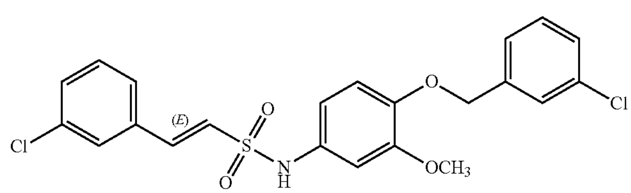 [SMILES: COc1cc(NS(=O)(=O)/C=C/c2cccc(Cl)c2)ccc1OCc1cccc(Cl)c1] | | | | |
| ef-rs-09-012 | 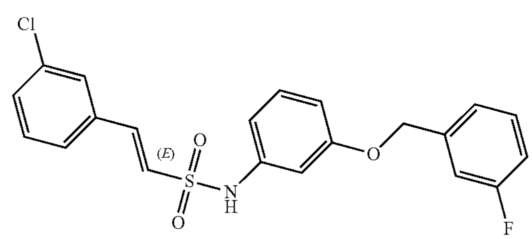 | | | | |
| ef-rs-09-018 | 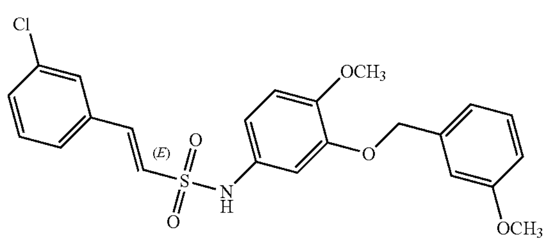 [SMILES: COc1cccc(COc2cc(NS(=O)(=O)/C=C/c3cccc(Cl)c3)ccc2OC)c1] | | | | |

TABLE 4-continued

Biochemical Data of Representative β-lactamase Inhibitors

| Compound | Structure | TEM-12 (R164S) (nM) | TEM-17 (E104K) (nM) | TEM-30 (R244S) (nM) | TEM-40 (M691) (nM) |
|---|---|---|---|---|---|
| ef-rs-09-014 | (structure) | | | | |

TABLE 5

Biochemical Data of Representative β-lactamase Inhibitors

| Compound | Structure | AmpC (nM) | IMP-1 (nM) | MIC (MRSA) [4 µg/mL] | MIC (VRSA) [4 µg/ml] |
|---|---|---|---|---|---|
| ef-rs-05-054 | (structure) | 555 ± 36 | 734 ± 106 | | |
| ef-rs-04-091 | (structure) | 671 ± 238 | 347 ± 43 | | |
| ef-rs-09-030 | (structure) | 553 ± 58 | 63 ± 8 | | |
| ef-rs-08-048 | (structure) | 477 ± 59 | 487 ± 90 | 2 | 0.25 |

TABLE 5-continued

Biochemical Data of Representative β-lactamase Inhibitors

| Compound | Structure | AmpC (nM) | IMP-1 (nM) | MIC (MRSA) [4 µg/mL] | MIC (VRSA) [4 µg/ml] |
| --- | --- | --- | --- | --- | --- |
| ef-rs-05-080 | 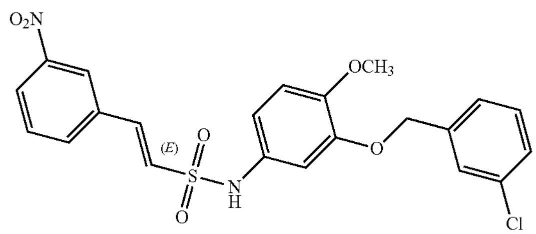 [SMILES: COc1ccc(NS(=O)(=O)/C=C/c2cccc([N+](=O)[O-])c2)cc1OCc1cccc(Cl)c1] | 563 ± 63 | 1100 ± 40 | | |
| ef-rs-09-029 | 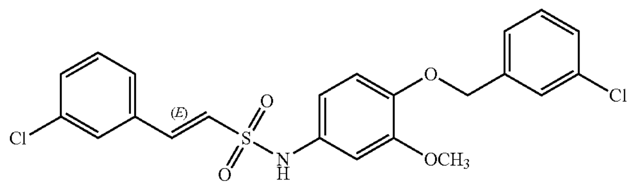 [SMILES: COc1cc(NS(=O)(=O)/C=C/c2cccc(Cl)c2)ccc1OCc1cccc(Cl)c1] | 706 ± 66 | 171 ± 20 | | |
| ef-rs-09-012 | 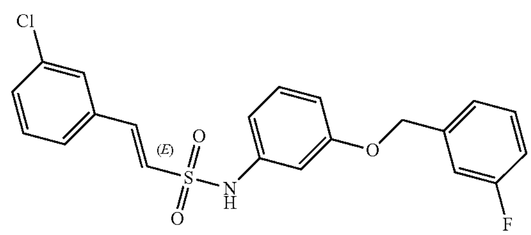 [SMILES: O=S(=O)(/C=C/c1cccc(Cl)c1)Nc1cccc(OCc2cccc(F)c2)c1] | 846 ± 100 | 157 ± 12 | | |
| ef-rs-09-018 | 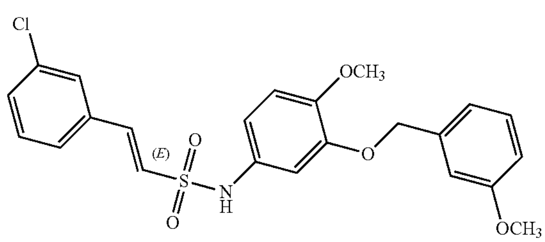 [SMILES: COc1cccc(COc2cc(NS(=O)(=O)/C=C/c3cccc(Cl)c3)ccc2OC)c1] | 1070 ± 360 | 256 ± 33 | | |
| ef-rs-09-014 | 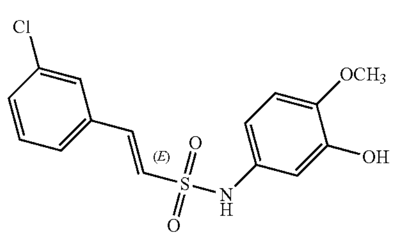 [SMILES: COc1ccc(NS(=O)(=O)/C=C/c2cccc(Cl)c2)cc1O] | 3750 ± 500 | 4690 ± 270 | | |

$T_{1/2}$ is microsomal stability; inhibition values are $IC_{50}$ unless noted.

Further, compound ef-rs-08-048 was tested against Methicillin-resistant (MRSA) and Vancomycin-resistant (VRSA) strains of the Gram-positive coccal bacterium *Staphylococcus aureus*. Compound ef-rs-08-048, at 4 µg/mL, reduced the Oxacillin MIC 8-fold in each of these strains.

Example 4

Chemical Synthesis of Representative β-Lactamase Inhibitors

Chemical Synthesis of ef-rs-08-052

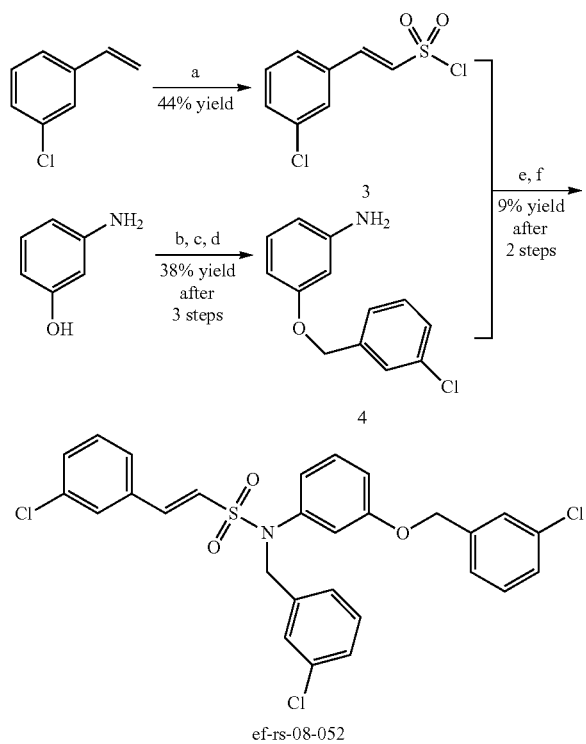

ef-rs-08-052

Reagents and conditions: (a) SO$_2$Cl$_2$, DMF, 55° C., 5 h; (b) (Boc)$_2$O, THF, 61° C., 24 h, 83% yield; (c) K$_2$CO$_3$, NaI, DMF, 3-chlorobenzylbromide, 79° C., 28 h, 55% yield; (d) TFA, DCM, rt 0.5 h, 83% yield; e) 1M Na$_2$CO$_3$, THF—H2O, rt, 3.5 h, 84% yield (f) NaH, 3-chlorobenzylbromide, THF, rt, 25 h, 11% yield.

The synthesis of compound ef-rs-08-052 used as a β-lactamase inhibitor claimed in this patent too, involved a six-step convergent procedure. The initial step comprised the formation of ethenesulfonyl chloride 3 which was formed after heating a DMF solution of 3-chlorostyrene with sulfuryl chloride. Alkylation of 3-aminophenol was performed by first protecting the amino group with (Boc)$_2$O and then alkylating the resulting Boc-phenol with 3-chlorobenzylbromide in the presence of potassium carbonate. Finally, deprotection of tert-butyl 3-(3-chlorobenzyloxy)phenylcarbamate 4b with TFA afforded aniline 4 in an 83% yield. Reaction of aniline 4 with sulfonyl chloride 3 using water as the solvent and Na$_2$CO$_3$ as the base produced sulfonamide 5 which was subsequently alkylated with 3-chlorobenzylbromide using NaH as the base to afford the final product ef-rs-08-052 in an 11% yield.

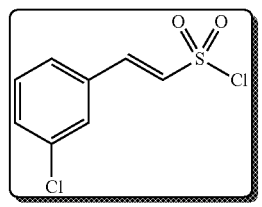

(E)-2-(3-chlorophenyl)ethenesulfonyl chloride (3): Sulfuryl chloride (3.2 mL, 38.5 mmol, 2 eq.) was added dropwise into a 2-neck mL round-bottomed flask containing 2.7 mL of DMF at 0° C. After stirring the mixture at room temperature for 30 min, 1-chloro-3-vinylbenzene (2.5 mL, 19.3 mmol, 1 eq.) was added and the reaction mixture was heated at 55° C. for 5 h. After the reaction mixture was cooled at room temperature, ice water was poured (20 mL) and the product was extracted three times from the aqueous phase with DCM. The resulting organic phase was washed once with water, brine and dried under Na$_2$SO$_4$. After the product was purified from the crude by flash column chromatography (5% EtOAc/hexanes), compound 20 (1.9785 g, 19.3 mmol) was obtained in a 44% yield. $^1$H NMR (400 MHz, CDCl$_3$) δ 7.67 (d, J=15.2 Hz, C=C$\underline{H}$, 1H), 7.55 (s, Ar$\underline{H}$, 1H), 7.50 (dt, J=6.4, 2.2 Hz, Ar$\underline{H}$, 1H), 7.46-7.40 (m, Ar$\underline{H}$, 2H), 7.25 (d, J=15.1 Hz, C=C$\underline{H}$, 1H). APT (100 MHz, CDCl$_3$, δ): 143.47 (C=$\underline{C}_8$H), 135.59 (C$_5$), 132.48 (C=$\underline{C}_9$H), 132.34 (C$_3$), 131.19 ($\underline{C}_1$H), 130.71 ($\underline{C}_2$H), 128.77 ($\underline{C}_4$H), 127.40 ($\underline{C}_6$H). GC-MS m/z (% relative intensity, ion): 239.95 (2, M+4), 237.95 (13, M+2), 235.95 (19, M$^+$), 201 (35, M$^+$-Cl), 137 (100, M$^+$-SO$_2$Cl), 102(85), 75 (45), 51 (28). HPLC: 99.7% pure, retention time 4.98 min.

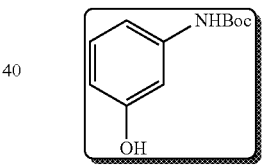

tert-butyl 3-hydroxyphenylcarbamate (4a): To a round-bottomed flask containing a solution of 3-aminophenol (1.0 g, 8.98 mmol, 1 eq.) in THF (15 mL) was poured (Boc)$_2$O (2.22 g, 9.88 mmol, 1.1 eq) and the reaction mixture was refluxed for 25 h. After the mixture was cooled at room temperature, EtOAc was added and the resulting organic phase was sequentially washed with a 2% solution of HCl, water, NaHCO$_3$ (sat), brine and dried under Na$_2$SO$_4$. After the product was purified from the crude by flash column chromatography (13% EtOAc/hexanes), the desired compound (1.5625 g, 7.47 mmol) was obtained in an 83% yield. $^1$H NMR (400 MHz, CDCl$_3$) δ 7.11 (t, J=8.1 Hz, Ar$\underline{H}$, 2H), 6.73 (d, J=8.0 Hz, Ar$\underline{H}$, 1H), 6.55 (s, N$\underline{H}$, 1H), 6.54 (d, J=8.3 Hz, Ar$\underline{H}$, 1H), 6.02 (s, O$\underline{H}$, 1H), 1.51 (s, C$\underline{H}_3$, 9H). $^{13}$C NMR (100 MHz, CDCl$_3$, δ): 156.50 (C$_3$), 153.02 (C=O), 139.28 (C$_5$), 129.87 ($\underline{C}_1$H), 110.80 ($\underline{C}_6$H), 110.41 ($\underline{C}_2$H), 106.13 ($\underline{C}_4$H), 80.98 (C$_4$), 28.35 ($\underline{C}$H$_3$). GC-MS m/z (% relative intensity, ion): 209.10 (11, M$^+$), 153 (78, M$^+$-C(CH$_3$)$_3$), 135 (18, M$^+$-C(CH$_3$)$_3$OH), 109 (100, M$^+$-C(CH$_3$)$_3$OCO), 57 (100, $^+$C(CH$_3$)$_3$), 41 (28). HPLC: 97.5% pure, retention time 7.02 min.

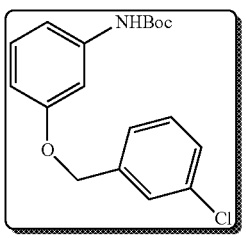

tert-butyl-3-(prop-2-ynyloxy)phenylcarbamate (4b): To a round-bottomed flask containing tert-butyl 3-hydroxyphenylcarbamate 4a (131.2 mg, 0.61 mmol, 1 eq.), $K_2CO_3$ (110.2 mg, 0.79 mmol, 1.3 eq) and NaI (9.2 mg, 0.06 mmol, 0.1 eq) was added 1.8 mL of a DMF solution of 3-chlorobenzylbromide (170.9 mg, 0.81 mmol, 1.32 eq) at room temperature. After the reaction mixture was heated at 79° C. for 28 h, water was added and the product was extracted three times with EtOAc from the aqueous phase. The resulting organic phase was washed twice with water, once with brine and dried under $Na_2SO_4$. After the product was purified from the crude by flash column chromatography (15% EtOAc/hexanes), compound 4b (121.4 mg) was obtained in a 55% yield. $^1$H NMR (400 MHz, $CDCl_3$) δ 7.44 (s, ArH, 1H), 7.30-7.23 (m, ArH4H), 7.18 (t, J=7.5 Hz, ArH, 1H), 6.83 (d, J=6.6 Hz, ArH, 1H), 6.64 (d, J=6.6 Hz, ArH, 1H), 6.45 (s, NH, 1H), 5.03 (s, CH$_2$, 2H), 1.52 (s, (CH$_3$)$_3$, 9H). HPLC: 93% pure, retention time 12.07 min.

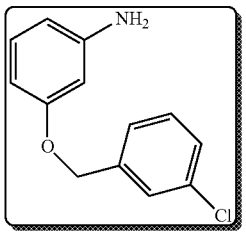

3-(3-chlorobenzyloxy)aniline (4): To a well stirred solution of compound 4b (104.5 mg, 0.31 mmol, 1 eq.) in $CH_2Cl_2$ (1.0 mL) was added TFA (0.26 mL, 3.25 mmol, 10.7 eq.) and the reaction mixture was stirred at room temperature for 0.5 h. After the solvent was evaporated, $NaHCO_3$ (sat) was added till the pH was about 7.5 and then, the product was extracted 3 times from the aqueous phase with DCM. The resulting organic phase was washed once with brine, dried under $Na_2SO_4$ and the solvent removed under vacuum to afford compound 4 (60.7 mg) in an 83% yield. $^1$H NMR (400 MHz, $CDCl_3$) δ 7.44 (s, ArH, 1H), 7.33-7.28 (m, ArH, 3H), 7.08 (td, J=7.7, 0.9 Hz, ArH, 1H), 6.39 (ddd, J=8.0, 2.3, 0.7 Hz, ArH, 1H), 6.35-6.30 (m, ArH, 2H), 5.00 (s, OCH$_2$, 2H), 3.67 (s, NH, 2H). APT NMR (100 MHz, $CDCl_3$, δ): 159.68 (C), 147.86 (C), 139.34 (C), 134.45 (C), 130.18 (CH), 129.82 (CH), 127.95 (CH), 127.35 (CH), 108.40 (CH), 104.69 (CH), 101.97 (CH), 68.94 (OCH$_2$).

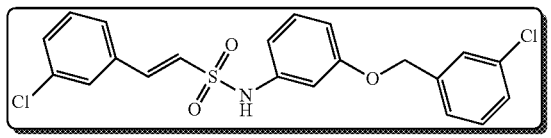

(E)-N-(3-(3-chlorobenzyloxy)phenyl)-2-(3-hlorophenyl)ethenesulfonamide (5): To a well stirred solution of compound 4 (25.71 mg, 0.110 mmol, 1 eq.) in a solution of $H_2O$-THF (0.4 mL, 2:1 ratio) was added compound 3 (35.29 mg, 0.131 mmol, 1.2 eq.) and then a 1M-solution of $Na_2CO_3$ (0.18 mL, 0.18 mmol, 1.6 eq.). After the reaction mixture was stirred for 2.5 h at room temperature, water was added and the product was extracted 3 times from the aqueous phase with EtOAc. The resulting organic phase was washed with brine, dried under $Na_2SO_4$ and the solvent evaporated. After the product was purified from the crude by flash column chromatography (20% EtOAc/hexanes), the desired product (41 mg, 0.092 mmol) was obtained in an 84% yield. $^1$H NMR (400 MHz, $CDCl_3$) δ 7.41 (d, J=15.4 Hz, C=CH, 1H), 7.39 (s, ArH, 1H), 7.37-7.33 (m, ArH, 2H), 7.31-7.23 (m, ArH, 5H), 7.20 (t, J=8.2 Hz, ArH, 1H), 7.04 (s, NH, 1H), 6.89 (t, J=2.2 Hz, ArH, 1H), 6.80 (d, J=15.4 Hz, C=CH, 1H), 6.79 (dd, J=8.0, 1.6 Hz, ArH, 1H), 6.73 (ddd, J=8.1, 2.5, 0.6 Hz, ArH, 1H), 4.99 (s, CH$_2$, 2H). APT NMR (100 MHz, $CDCl_3$, δ): 159.31 (C), 141.50 (CH), 138.62 (C), 137.55 (C), 135.08 (C), 134.50 (C), 133.97 (C), 130.95 (CH), 130.43 (CH), 130.30 (CH), 129.87 (CH), 128.18 (CH), 128.05 (CH), 127.44 (CH), 126.59 (CH), 125.68 (CH), 125.41 (CH), 113.24 (CH), 111.69 (CH), 107.28 (CH), 69.19 (OCH$_2$). GC-MS m/z (% relative intensity, ion): 436.95 (0.01, M+4), 434.95 (0.16, M+2), 432.95 (0.23, M$^+$), 369.05 (4.9, M$^+$-SO$_2$), 243.95 (4.9), 124.95 (100), 102 (9.1), 88.95 (11.3). HPLC: 97.9% pure, retention time 12.16 min.

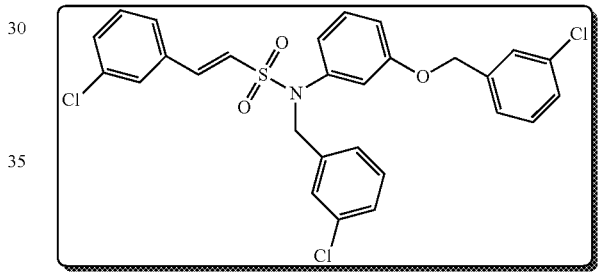

(E)-N-(3-chlorobenzyl)-N-(3-(3-chlorobenzyloxy)phenyl)-2-(3-chlorophenyl)ethenesulfonamide (ef-rs-08-052): To a well stirred suspension of NaH (34.3 mg, 1.36 mmol, 15 eq.) in 1 mL of anhydrous THF, a THF solution (1 mL) of compound 5 (41 mg, 0.091 mmol, 1 eq.) was added and the mixture was stirred for 47 minutes at room temperature. Afterwards, the reaction mixture was cooled at 0° C. and a THF solution (0.6 mL) of 3-chlorobenzylbromide (23 mg, 0.109 mmol, 1.2 eq.) was added. After the reaction mixture was stirred at room temperature for 25 h, water was added and the product was extracted three times from the aqueous phase with EtOAc. The resulting organic phase was washed with brine, dried under $Na_2SO_4$ and the solvent evaporated. After the product was purified from the crude by flash column chromatography (20% EtOAc/hexanes), compound ef-rs-08-052 (5.9 mg, 0.01 mmol) was obtained in an 11% yield. $^1$H NMR (400 MHz, $CDCl_3$) δ 7.47 (t, J=1.6 Hz, ArH, 1H), 7.43 (dt, J=7.6, 1.7 Hz, ArH, 1H), 7.41-7.15 (m, ArH, 13H), 6.92-6.85 (m, ArH, 2H), 6.82 (d, J=15.5 Hz, C=CH, 1H), 4.96 (s, OCH$_2$, 2H), 4.77 (s, NCH$_2$, 2H). DEPT 135 NMR (100 MHz, $CDCl_3$, δ): 141.04 (CH), 130.91 (CH), 130.44 (CH), 130.05 (CH), 129.92 (CH), 129.82 (CH), 128.56 (CH), 128.29 (CH), 128.11 (CH), 127.93 (CH), 127.47 (CH), 126.62 (CH), 126.55 (CH), 125.41 (CH), 124.87 (CH), 121.12 (CH), 115.93 (CH), 114.85 (CH), 69.35 (OCH$_2$), 54.49 (NCH$_2$). HPLC: 95.9% pure, retention time 13.11 min.

Chemical Synthesis of ef-rs-05-049

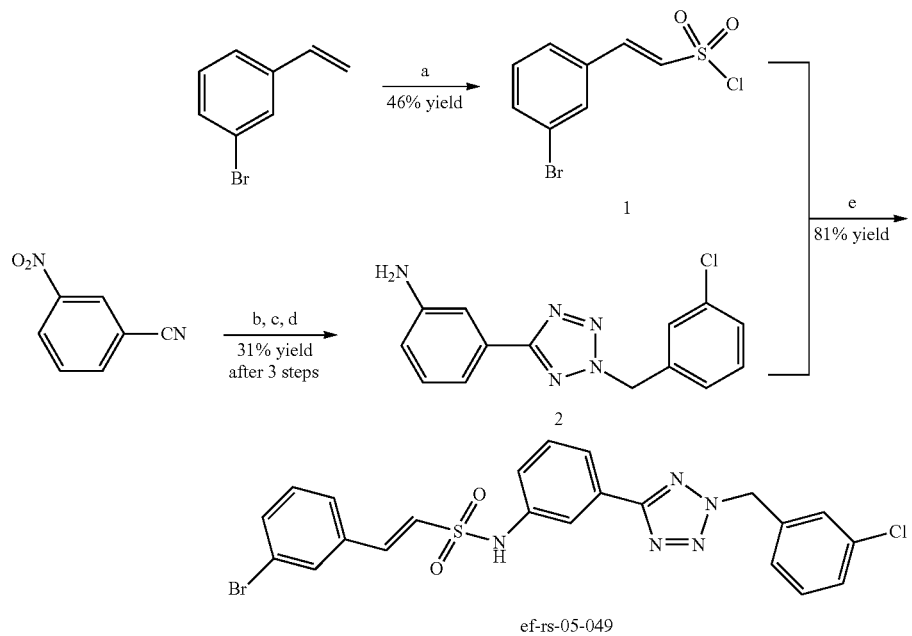

Scheme 2. Synthesis of ef-rs-05-049.

Reagents and conditions (a) SO₂Cl₂, DMF, 75° C.,
3 h; (b) NaN₃, ZnBr₂, H₂O, reflux, 31 h, 94% yield; (c) TEA, 3-
chlorobenzylbromide, AN, rt, 23 h, 34% yield; (d) Zn, AcOH, rt, 2.5 h, 97% yield; e)
1M Na₂CO₃, THF—H2O, rt, 1.5-5 h The synthesis of compound ef-rs-05-049, a representative β-lactamase inhibitor, involved a five-step convergent procedure. The initial step comprised the formation of ethenesulfonyl chloride 1 which was formed after heating a DMF solution of 3-bromostyrene with sulfuryl chloride. Synthesis of aniline 2 involved a 3-step route in which, 3-nitrobenzonitrile initially reacted with sodium azide and ZnBr₂ to form its corresponding nitrotetrazole which was subsequently alkylated by 3-chlorobenzylbromide and afterwards reduced with Zn/AcOH to form the desired 3-(2-(3-chlorobenzyl)-2H-tetrazol-5-yl)aniline 2. The last step in the synthesis was achieved by reacting aniline 2 with sulfonyl chloride 1 using water as the solvent and Na₂CO₃ as the base. When THF was added to this reaction as a co-solvent in a 1:1 ratio, the yields were considerably increased.

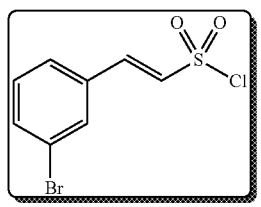

(E)-2-(3-bromophenyl)ethenesulfonyl chloride (1): Sulfuryl chloride (2.5 mL, 30.2 mmol, 2 eq.) was added dropwise into a 2-neck round-bottomed flask containing 2.7 mL of DMF at 0° C. After stirring the mixture at room temperature for 30 min, 1-bromo-3-vinylbenzene (2 mL, 14.9 mmol, 1 eq.) was added and the reaction mixture was heated at 75° C. for 3 h. After the reaction mixture was cooled at room temperature, ice water was poured and the product was extracted three times from the aqueous phase with DCM. The resulting organic phase was washed once with water and brine and then dried under Na₂SO₄. Subsequently, the product was purified from the crude by flash column chromatography (5% EtOAc/hexanes) to afford compound 1 (1.9285 g, 6.89 mmol) in a 46% yield. ¹H NMR (400 MHz, CDCl₃) δ 7.71 (s, Ar$\underline{H}$, 1H), 7.65 (d, J=15.2 Hz, C=C$\underline{H}$, 1H), 7.65 (d, J=7.1 Hz, Ar$\underline{H}$, 1H), 7.49 (d, J=7.7 Hz, Ar$\underline{H}$, 1H), 7.36 (t, J=7.9 Hz, Ar$\underline{H}$, 1H), 7.24 (d, J=15.3 Hz, C=C$\underline{H}$, 1H). DEPT135 (100 MHz, CDCl₃, δ): 143.41 (C=$\underline{C}$H), 135.35 (C=$\underline{C}$H), 131.70 ($\underline{C}$H), 131.16 ($\underline{C}$H), 130.96 ($\underline{C}$H), 127.84 ($\underline{C}$H).

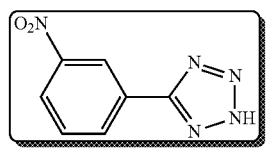

5-(3-nitrophenyl)-2H-tetrazole (2a): To a 2-neck round-bottomed flask containing 3-nitrobenzonitrile (1.0 g, 6.62 mmol, 1 eq.), sodium azide (475.6 mg, 7.28 mmol, 1.1 eq.) and ZnBr₂ (1.49 g, 6.62 mmol, 1 eq.) was added 13 mL of distilled water (0.33 M) and the mixture was refluxed for 51 h. After the mixture was cooled at room temperature, a solution of HCl (3N) was added until the pH was about 1 and then the product was extracted 3 times from the aqueous phase with EtOAc. After the resulting organic phase was evaporated, the remaining solid was treated with a solution of NaOH (0.35 N) till the pH was about 10 and the resultant mixture was stirred for 1 h at room temperature. The solid that was formed and later discarded was filtered and washed twice with NaOH (0.35 N) and the filtrate was treated with a solution of HCl (3N) till the pH was about 2. The solid formed was filtered, washed once with a solution of HCl (3N) and finally dried to afford the desired tetrazole (1.1938 g, 6.24 mmol) in a 94% yield. $^1$H NMR (400 MHz, DMSO) δ 8.84 (d, J=1.6 Hz, ArH, 1H), 8.49 (ddd, J=7.8, 1.7, 0.8 Hz, ArH, 1H), 8.43 (ddd, J=8.3, 2.2, 0.9 Hz, ArH, 1H), 7.92 (t, J=8.0 Hz, ArH, 1H), 3.36 (s, NH, 2H). DEPT135 (100 MHz, DMSO, δ): 133.09 (CH), 131.26 (CH), 125.61 (CH), 121.53 (CH).

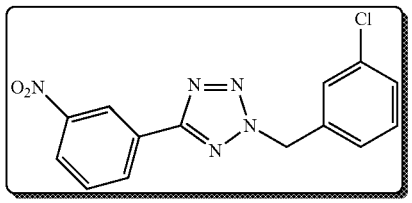

2-(3-chlorobenzyl)-5-(3-nitrophenyl)-2H-tetrazole (2b): To a well stirred solution of compound 25a (500 mg, 2.62 mmol, 1 eq.) in 2 mL of acetonitrile was sequentially added 3.6 mL of acetonitrile solution of 3-chlorobenzylbromide (554.1 mg, 2.62 mmol, 1 eq.) and then TEA (0.92 mL, 6.54 mmol, 2.5 eq.). After the reaction mixture was stirred for 23 h at room temperature, the solid that was formed and later discarded was filtered and rinsed it with cold acetonitrile. After the filtrate was evaporated, EtOAc was added to the resulting residue and the resulting organic phase was washed once with water, brine and dried under Na$_2$SO$_4$. After the product was purified from the reaction crude by flash column chromatography (30% EtOAc/hexanes), compound 25b (280.5 mg) was obtained in a 34% yield. $^1$H NMR (400 MHz, CDCl$_3$) δ 8.97 (s, ArH, 1H), 8.47 (d, J=7.7 Hz, ArH, 1H), 8.30 (d, J=8.2 Hz, ArH, 1H), 7.67 (t, J=7.9 Hz, ArH, 1H), 7.43 (s, ArH, 1H), 7.33 (br. s, ArH, 3H), 5.81 (s, CH$_2$, 2H). $^{13}$C NMR (100 MHz, CDCl$_3$, δ): 163.73 (C), 148.65 (C), 135.01 (C), 134.67 (C), 132.53 (CH), 130.45 (CH), 130.06 (CH), 129.45 (CH), 128.94 (C), 128.65 (CH), 126.66 (CH), 124.94 (CH), 121.90 (CH), 56.37 (CH$_2$). HPLC: 96% pure, retention time 11.34 min.

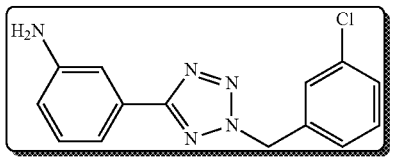

3-(2-(3-chlorobenzyl)-2H-tetrazol-5-yl)aniline (2): To a well stirred solution of compound 25b (50.7 mg, 0.16 mmol, 1 eq.) in 3.1 mL of glacial acetic acid was added Zn (619.6 mg, 9.47 mmol, 59 eq.) in two portions with the second part added after 14 minutes. After the reaction mixture was stirred at room temperature for 2.5 h, it was filtered through a pad of celite, rinsed it with EtOAc and the solvent was evaporated. The residue formed was treated with NaHCO$_3$ (sat) until the pH was about 7.5 and the product was extracted twice from the aqueous phase with EtOAc. The resulting organic phase was subsequently washed with brine, dried under Na$_2$SO$_4$ and the solvent evaporated to afford compound 25 (44.3 mg, 0.155 mmol) in a 97% yield. $^1$H NMR (400 MHz, CDCl$_3$) δ 7.53 (d, J=7.8 Hz, ArH, 1H), 7.48 (d, J=1.8 Hz, ArH, 1H), 7.40 (s, ArH, 1H), 7.36-7.24 (m, ArH, 4H), 6.78 (dd, J=8.0, 2.3 Hz, ArH, 1H), 5.76 (s, CH$_2$, 2H), 3.89 (s, NH, 2H). $^{13}$C NMR (100 MHz, CDCl$_3$, δ): 165.67 (C), 146.75 (C), 135.15 (C), 134.84 (C), 130.29 (CH), 129.88 (CH), 129.15 (CH), 128.47 (CH), 127.99 (C), 126.44 (CH), 117.07 (CH), 117.02 (CH), 113.10 (CH), 55.97 (CH$_2$). HPLC: 90% pure, retention time 8.93 min.

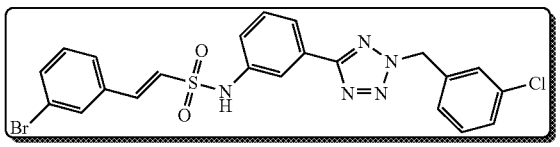

(E)-N-(3-(2-(3-chlorobenzyl)-2H-tetrazol-5-yl)phenyl)-2-m-tolylethenesulfonamide (ef-rs-05-049): To a well stirred solution of compound 2 (15 mg, 0.053 mmol, 1 eq.) in a solution of H$_2$O-THF (0.6 mL, 2:1 ratio) was gradually added compound 1 (19.1 mg, 0.068 mmol, 1.3 eq.) and then a 1M-solution of Na$_2$CO$_3$ (0.01 mL, 0.01 mmol, 0.15 eq.) for a period of 10 minutes. After the reaction mixture was stirred for 2 hours at room temperature, water was added and the product was extracted 3 times with EtOAc from the aqueous phase. The resulting organic phase was washed with brine, dried under Na$_2$SO$_4$ and the solvent evaporated.

Recrystallization of the resulting solid (EtOAc/hexanes) afforded compound ef-rs-05-049 (22.7 mg, 0.042 mmol) in an 81% yield. $^1$H NMR (400 MHz, CD$_2$Cl$_2$) δ 7.93 (d, J=2.5 Hz, ArH1H), 7.91 (d, J=8.7 Hz, ArH1H), 7.75 (t, J=1.5 Hz, ArH1H), 7.68 (d, J=15.4 Hz, C=CH, 1H), 7.67 (d, J=7.7 Hz, ArH1H), 7.60 (t, J=1.5 Hz, ArH1H), 7.53 (d, J=7.2 Hz, ArH, 1H), 7.50-7.30 (m, ArH, 5H), 7.25 (t, J=8.1 Hz, ArH1H), 6.84 (d, J=15.4 Hz, C=CH, 1H), 6.69 (s, NH, 1H), 5.79 (s, CH$_2$, 2H). HPLC: 99.0% pure, retention time 11.98 min.

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Koehler, K. A. and Lienhard, G. E. (1971) Biochemistry 10, 2477-2483.

Ness, S., Kindler, A. M., Mark Paetzel., Gold, M., Jensen, S. E., Jones, J. B., Strynadka, N. C. (2000) Biochemistry 39, 5312-5321.

Morandi, F., Caselli, E., Morandi, S., Focia, P. J., Blazquez, J., Shoichet, B. K., and Prati, F. (2003) J. Am. Chem. Soc. 125, 685-695.

Powers, R. A., and Schoichet, B. K. (2002) J. Med. Chem. 45 3222-3234. Rudgers, G. W., Huang, W., Palzkill, T. (2001) Antimicrobial Agents and Chem. 45 3279-3286.

Bonomo, R. A, Rudin, S. A, Shlaes, D. M. (1997) FEMS Microbiology Letters 148 59-62.

Velazquez-Campoy, A., Kiso, Y. and Freire, E. (2001) Arch. Biochim. Biophys. 390 169-175.

Ohtaka, H., Velazquez-Campoy, A. and Freire, E. (2002) Protein Science 11 1908-1916.

Queenan and Bush, Clin. Microbiol. Rev., 20, 440-458 (2007)

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A compound of Formula (I):

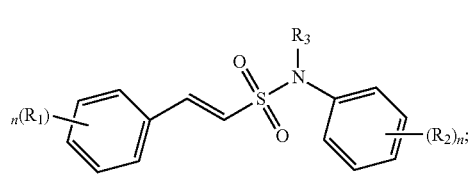

wherein:
each n is independently an integer selected from the group consisting of 1, 2, 3, 4, and 5;
each $R_2$ is independently selected from the group consisting of:

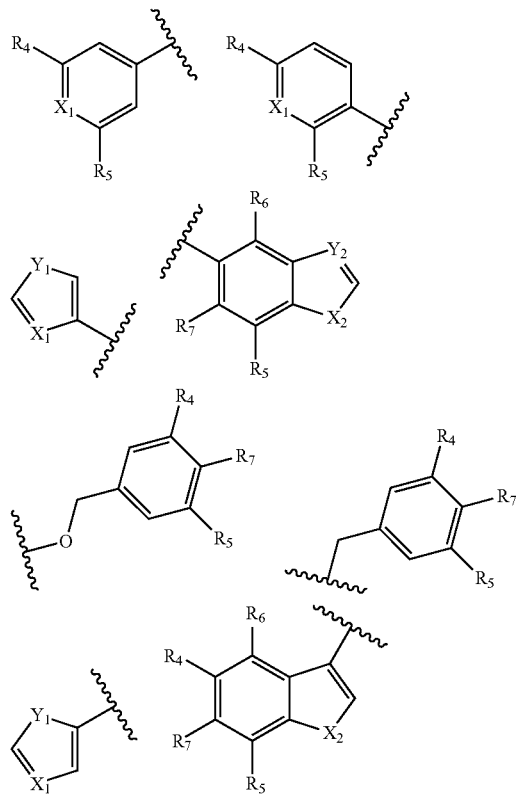

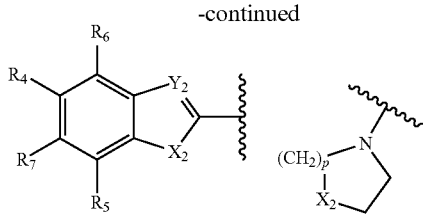

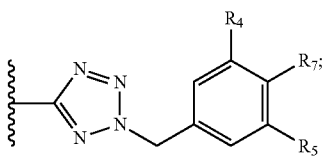

$R_3$ is selected from the group consisting of hydrogen, hydroxyl, alkoxyl, and

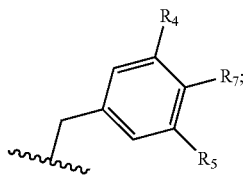

p is an integer selected from the group consisting of 1 and 2;

$X_1$ is selected from the group consisting of N and $CR_8$;

$X_2$ is selected from the group consisting of S, $NR_8$, and $CR_8R_9$;

$Y_1$ is selected from the group consisting of S, O, and $NR_8$;

$Y_2$ is selected from the group consisting of N and $CR_8$;

$R_1$, $R_4$, $R_5$, $R_6$, and $R_7$ are each independently selected from the group consisting of hydrogen, substituted or unsubstituted alkyl, alkoxyl, hydroxyl, hydroxyalkyl, carboxyl, acyl, Cl, Br, $NO_2$, —$NH_2$, F, phenyl, cyclohexyl, benzyloxyl, and —$SO_3H$, including —$COOR_{10}$, wherein $R_{10}$ is lower alkyl, carbonyl, carbamoyl, alkylcarbamoyl, halogen, amino, nitro, nitrile, amide, haloalkyl, aryl, cycloalkyl, aralkyloxyl, and —$SO_3H$;

$R_8$, and $R_9$ are each independently selected from the group consisting of hydrogen, substituted or unsubstituted alkyl, alkoxyl, hydroxyl, hydroxyalkyl, carboxyl, acyl, including —$COOR_{10}$, wherein $R_{10}$ is lower alkyl, carbonyl, carbamoyl, alkylcarbamoyl, halogen, amino, nitro, nitrile, amide, haloalkyl, aryl, cycloalkyl, aralkyloxyl, and —$SO_3H$;

and a pharmaceutically acceptable salt, prodrug, or solvate thereof.

2. The compound of claim 1, wherein $R_1$, $R_4$, $R_5$, $R_6$, and $R_7$ are each independently selected from the group consisting of t-butyl, Cl, Br, methyl, —$OCH_3$, —$NO_2$, —$NH_2$, —OH, —$CH_2OH$, —CHO, —COOH, —$COOCH_3$, —$COOCH_2CH_3$, —$CF_3$, —$CONHCH_3$, —C≡N, —$CONH_2$, H, F, isopropyl, phenyl, cyclohexyl, benzyloxyl, and —$SO_3H$.

3. The compound of claim 1, wherein the compound of Formula (I) is selected from the group consisting of:

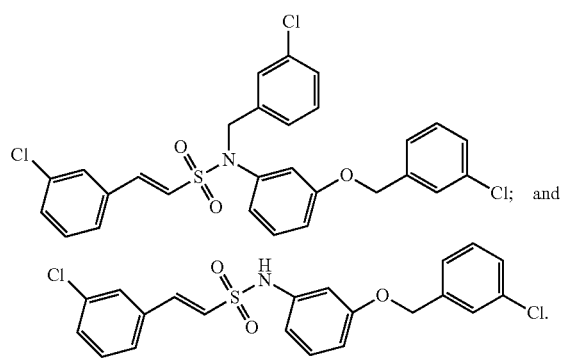
and
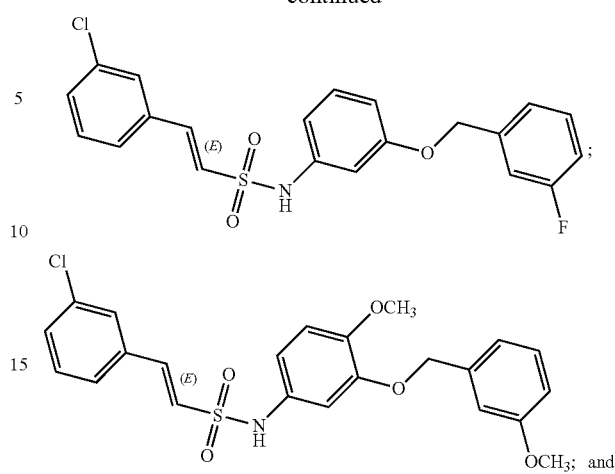
4. The compound of claim 1, wherein the compound of Formula (I) is selected from the group consisting of:
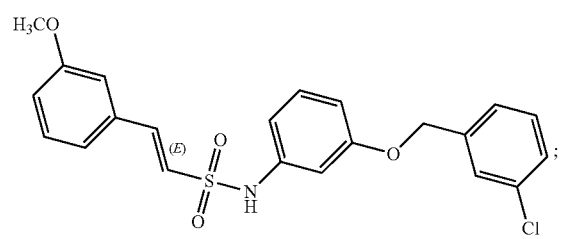
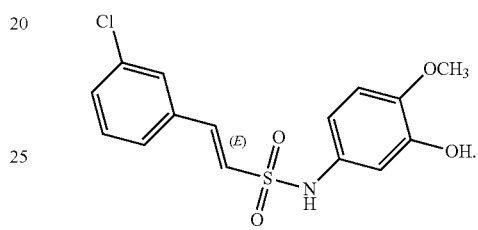
and
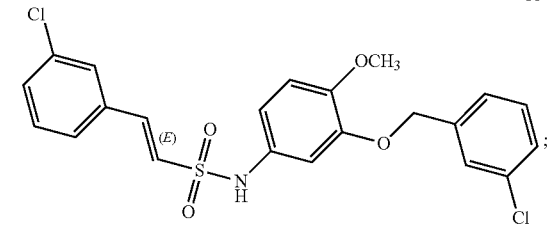
5. The compound of claim 1, wherein $R_2$ is
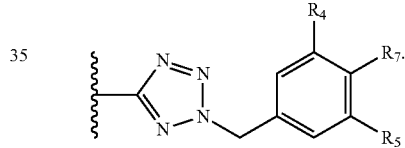
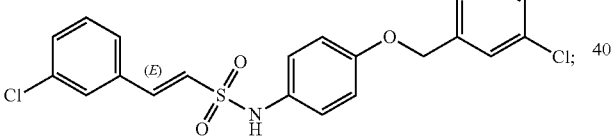
6. The compound of claim 5, wherein the compound of Formula (I) is selected from the group consisting of:
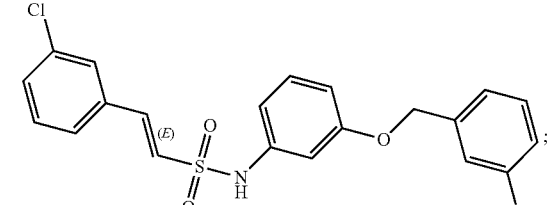
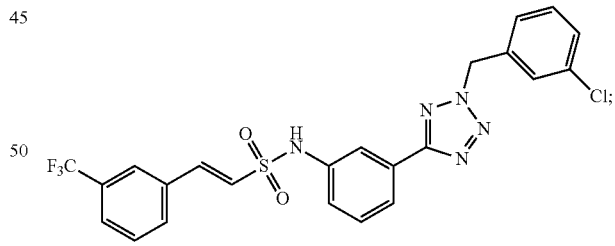
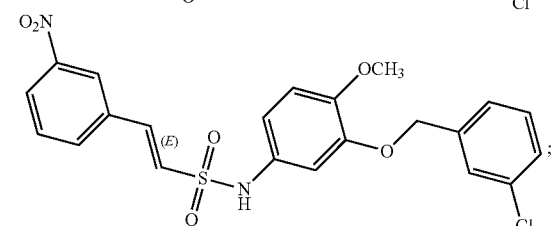
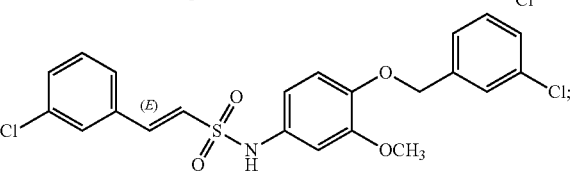
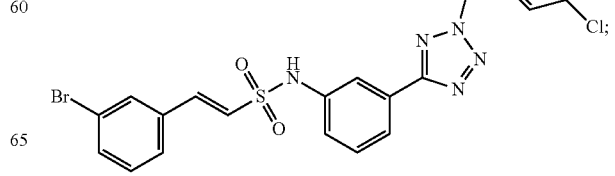

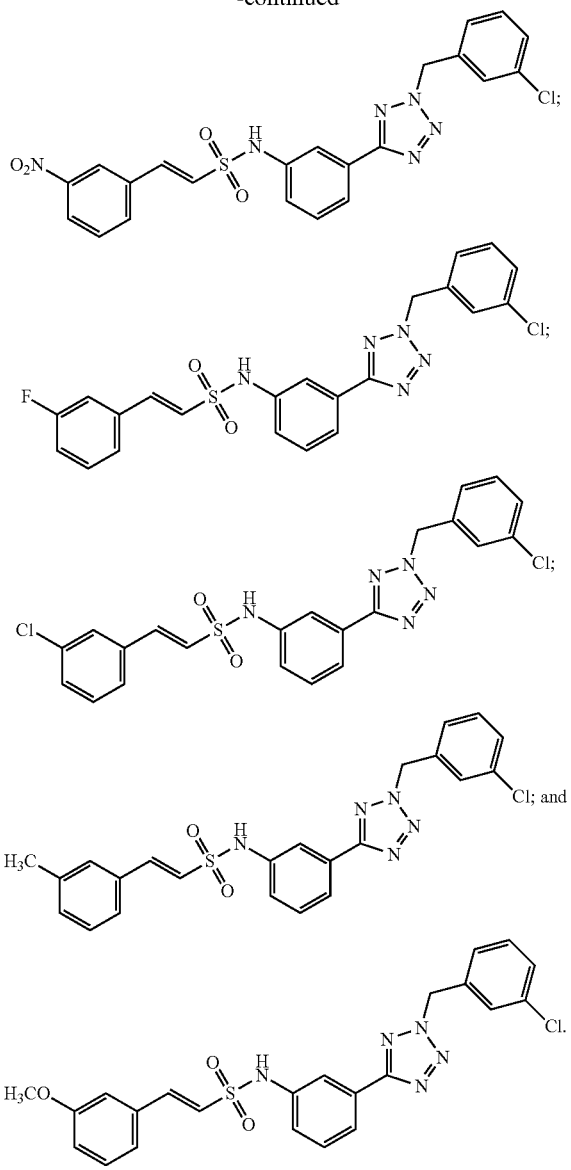

7. A pharmaceutical composition comprising a compound of claim 1 and a pharmaceutically acceptable carrier.

8. A pharmaceutical composition comprising a compound of claim 1, one or more antibacterial agents, and a pharmaceutically acceptable carrier.

9. The pharmaceutical composition of claim 8, wherein the antibacterial agent is selected from the group consisting of a beta-lactam antibiotic, a fluoroquinolone, a quinolone, a macrolide, a tetracycline, and combinations thereof.

10. The pharmaceutical composition of claim 9, wherein the beta-lactam antibiotic is selected from the group consisting of a cephalosporin, a penicillin, a monobactam, a carbapenem, and a carbacephem.

11. The pharmaceutical composition of claim 9, wherein the beta-lactam antibiotic is selected from the group consisting of loracarbef, ertapenem, doripenem, imipenem/cilastatin, meropenem, cefadroxil, cefazolin, cefalotin or cefalothin, cefalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftobiprole, aztreonam, amoxicillin, ampicillin, azlocillin, carbenicillin, dicloxacillin, flucloxacillin, mezlocillin, methicillin, nafcillin, oxacillin, penicillin g, penicillin v, piperacillin, temocillin, ticarcillin, amoxicillin/clavulanate, ampicillin/sulbactam, piperacillin/tazobactam, ticarcillin/clavulanate.

12. The pharmaceutical composition of claim 9, wherein the fluoroquinolone is selected from the group consisting of ciprofloxacin, clinafloxacin, enoxacin, fleroxacin, gatifloxacin, moxifloxacin, gemifloxacin, grepafloxacin, levofloxacin, norfloxacin, sparfloxacin, and trovafloxacin.

13. The pharmaceutical composition of claim 9, wherein the quinolone is selected from the group consisting of cinoxacin, garenoxacin, and nalidixic acid.

14. The pharmaceutical composition of claim 9, wherein the macrolide is selected from the group consisting of azithromycin, clarithromycin, dirithromycin, erythromycin, lincomycin, roxithromycin, troleandomycin, telithromycin, and spectinomycin.

15. The pharmaceutical composition of claim 9, wherein the tetracycline is selected from the group consisting of demeclocycline, doxycycline, minocycline, oxytetracycline, and tetracycline.

16. A method for inhibiting a beta lactamase, the method comprising contacting the beta lactamase with a compound of Formula (I) in an amount to inhibit the beta lactamase:

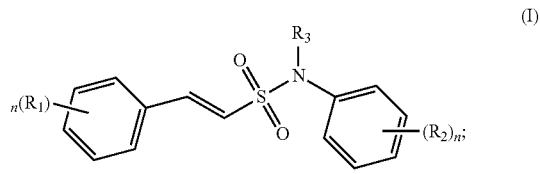

(I)

wherein:
each n is independently an integer selected from the group consisting of 1, 2, 3, 4, and 5;
each $R_2$ is independently selected from the group consisting of:

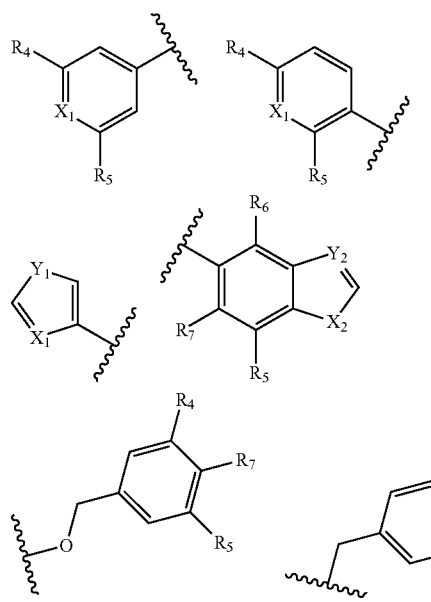

-continued

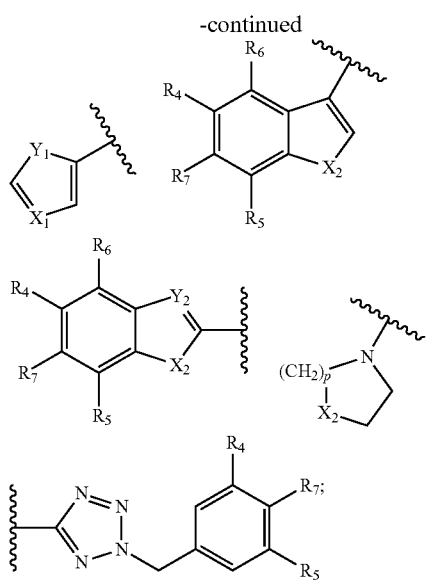

R₃ is selected from the group consisting of: hydrogen, hydroxyl, alkoxyl, and

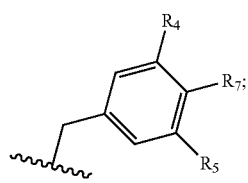

p is an integer selected from the group consisting of 1 and 2;
X₁ is selected from the group consisting of N and CR₈;
X₂ is selected from the group consisting of S, NR₈, and CR₈R₉;
Y₁ is selected from the group consisting of S, O, and NR₈;
Y₂ is selected from the group consisting of N and CR₈;
R₁, R₄, R₅, R₆, and R₇ are each independently selected from the group consisting of hydrogen, substituted or unsubstituted alkyl, alkoxyl, hydroxyl, hydroxyalkyl, carboxyl, acyl, Cl, Br, NO₂, —NH₂, F, phenyl, cyclohexyl, benzyloxyl, and —SO₃H, including —COOR₁₀, wherein R₁₀ is lower alkyl, carbonyl, carbamoyl, alkylcarbamoyl, halogen, amino, nitro, nitrile, amide, haloalkyl, aryl, cycloalkyl, aralkyloxyl, and —SO₃H;
R₈ and R₉ are each independently selected from the group consisting of hydrogen, substituted or unsubstituted alkyl, alkoxyl, hydroxyl, hydroxyalkyl, carboxyl, acyl, including —COOR₁₀, wherein R₁₀ is lower alkyl, carbonyl, carbamoyl, alkylcarbamoyl, halogen, amino, nitro, nitrile, amide, haloalkyl, aryl, cycloalkyl, aralkyloxyl, and —SO₃H;
and a pharmaceutically acceptable salt, prodrug, or solvate thereof.

17. The method of claim 16, wherein R₁, R₄, R₅, R₆, and R₇ are each independently selected from the group consisting of t-butyl, Cl, Br, methyl, —OCH₃, —NO₂, —NH₂, —OH, —CH₂OH, —CHO, —COOH, —COOCH₃, —COOCH₂CH₃, —CF₃, —CONHCH₃, —C≡N, —CONH₂, H, F, isopropyl, phenyl, cyclohexyl, benzyloxyl, and —SO₃H.

18. The method of claim 16, wherein the compound of Formula (I) is selected from the group consisting of:

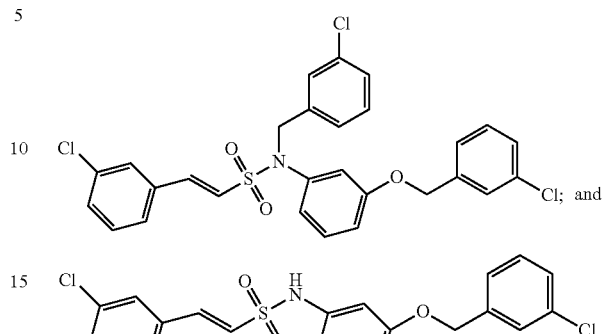

19. The method of claim 16, wherein the compound of Formula (I) is selected from the group consisting of:

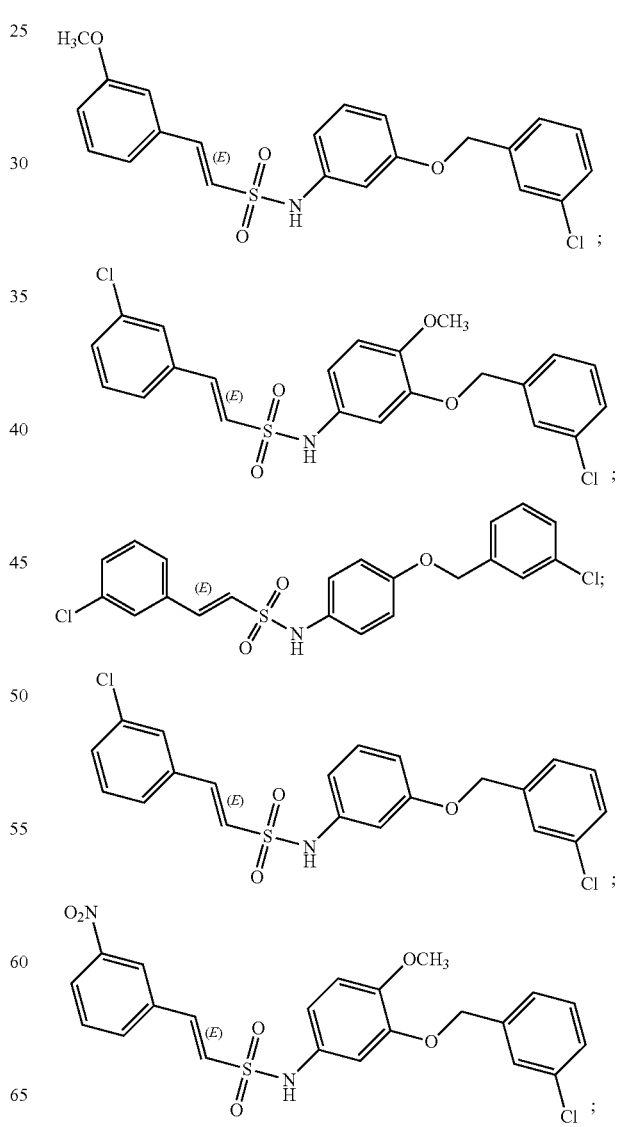

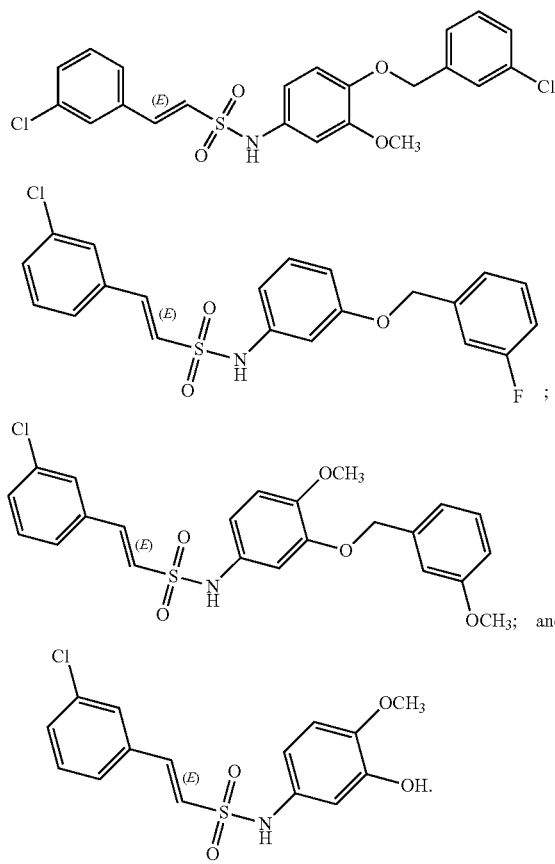

20. The method of claim 16, wherein $R_2$ is

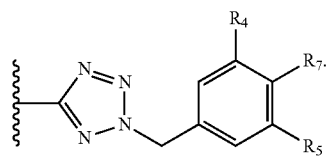

21. The method of claim 19, wherein the compound of Formula (I) is selected from the group consisting of:

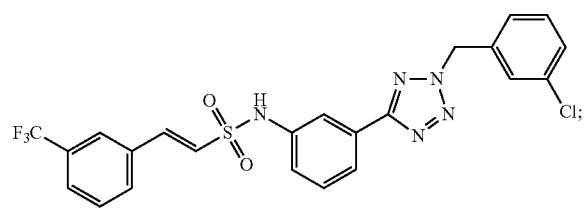

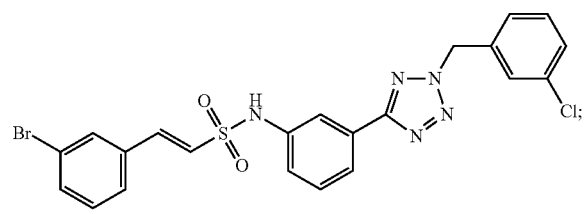

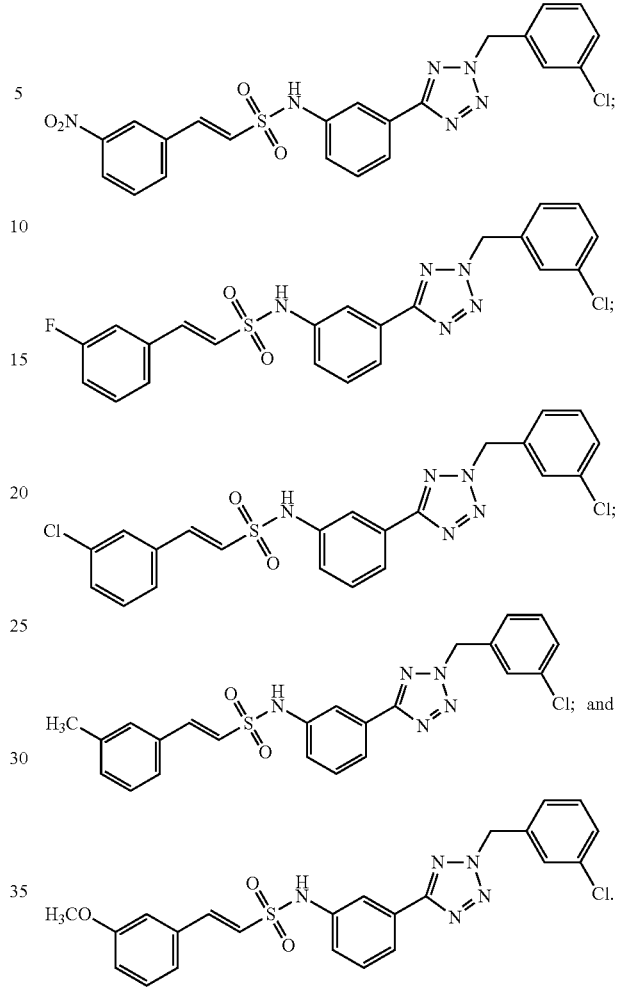

22. The method of claim 21, wherein the beta-lactamase is selected from the group consisting of a Class A beta-lactamase, a Class B beta-lactamase, a Class C beta-lactamase, and a Class D beta-lactamase.

23. The method of claim 22, wherein the beta-lactamase is a Class A (TEM) beta-lactamase.

24. The method of claim 22, wherein the beta-lactamase is a Class B (IMP-1) beta-lactamase.

25. The method of claim 22, wherein the beta-lactamase is a Class C (AmpC) beta-lactamase.

26. A method for treating a bacterial infection in a subject having said infection thereof, the method comprising administering to the subject a therapeutically-effective amount of a beta-lactam antibiotic, optionally in combination with one or more other antibacterial agents, in combination with a therapeutically-effective amount of a compound of Formula (I):

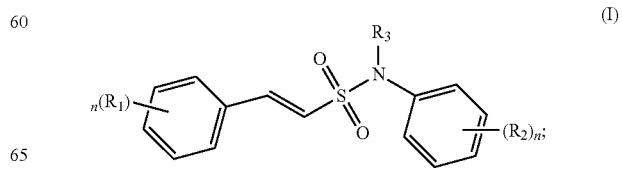

wherein:
each n is independently an integer selected from the group consisting of 1, 2, 3, 4, and 5;
each $R_2$ is independently selected from the group consisting of:

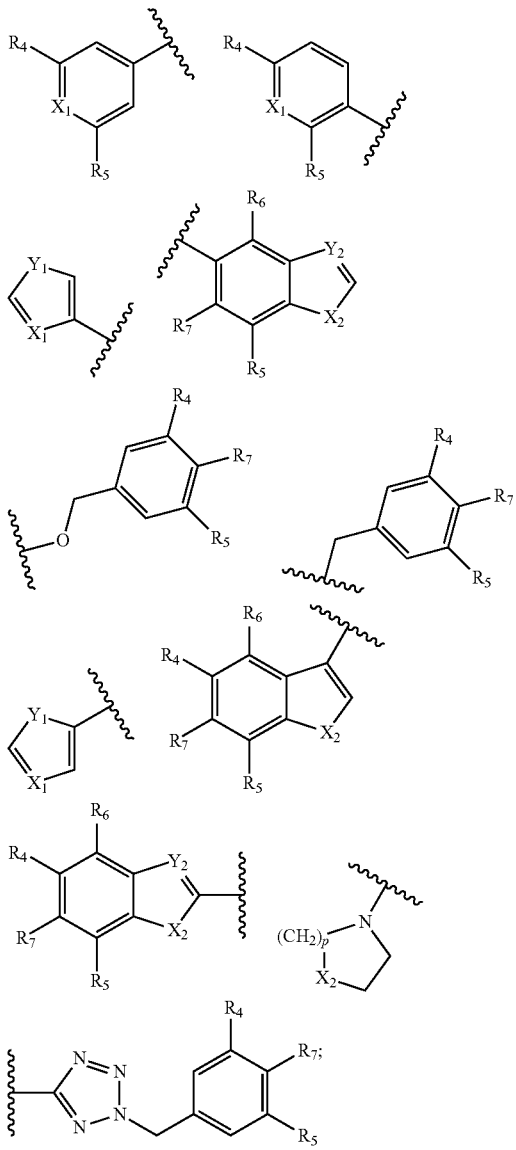

$R_3$ is selected from the group consisting of: hydrogen, hydroxyl, alkoxyl, and

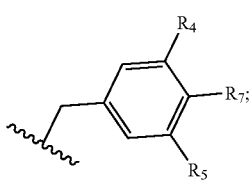

p is an integer selected from the group consisting of 1 and 2;
$X_1$ is selected from the group consisting of N and $CR_8$;
$X_2$ is selected from the group consisting of S, $NR_8$, and $CR_8R_9$;
$Y_1$ is selected from the group consisting of S, O, and $NR_8$;
$Y_2$ is selected from the group consisting of N and $CR_8$;
$R_1, R_4, R_5, R_6,$ and $R_7$ are each independently selected from the group consisting of hydrogen, substituted or unsubstituted alkyl, alkoxyl, hydroxyl, hydroxyalkyl, carboxyl, acyl, Cl, Br, $NO_2$, $-NH_2$, F, phenyl, cyclohexyl, benzyloxyl, and $-SO_3H$, including $-COOR_{10}$, wherein $R_{10}$ is lower alkyl, carbonyl, carbamoyl, alkylcarbamoyl, halogen, amino, nitro, nitrile, amide, haloalkyl, aryl, cycloalkyl, aralkyloxyl, and $-SO_3H$;
$R_8$ and $R_9$ are each independently selected from the group consisting of hydrogen, substituted or unsubstituted alkyl, alkoxyl, hydroxyl, hydroxyalkyl, carboxyl, acyl, including $-COOR_{10}$, wherein $R_{10}$ is lower alkyl, carbonyl, carbamoyl, alkylcarbamoyl, halogen, amino, nitro, nitrile, amide, haloalkyl, aryl, cycloalkyl, aralkyloxyl, and $-SO_3H$;
and a pharmaceutically acceptable salt, prodrug, or solvate thereof.

27. The method of claim 26, wherein $R_1$, $R_4$, $R_5$, $R_6$, and $R_7$ are each independently selected from the group consisting of t-butyl, Cl, Br, methyl, $-OCH_3$, $-NO_2$, $-NH_2$, $-OH$, $-CH_2OH$, $-CHO$, $-COOH$, $-COOCH_3$, $-COOCH_2CH_3$, $-CF_3$, $-CONHCH_3$, $-C\equiv N$, $-CONH_2$, H, F, isopropyl, phenyl, cyclohexyl, benzyloxyl, and $-SO_3H$.

28. The method of claim 26, wherein the compound of Formula (I) is selected from the group consisting of:

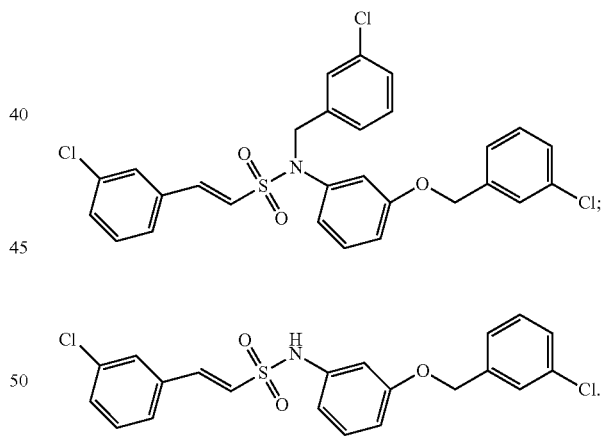

29. The method of claim 26, wherein the compound of Formula (I) is selected from the group consisting of:

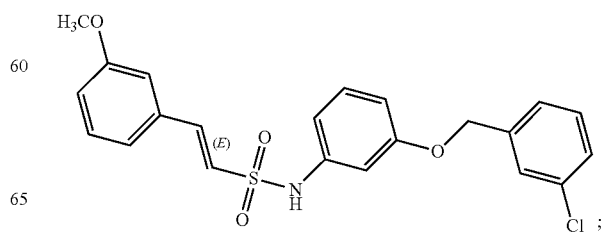

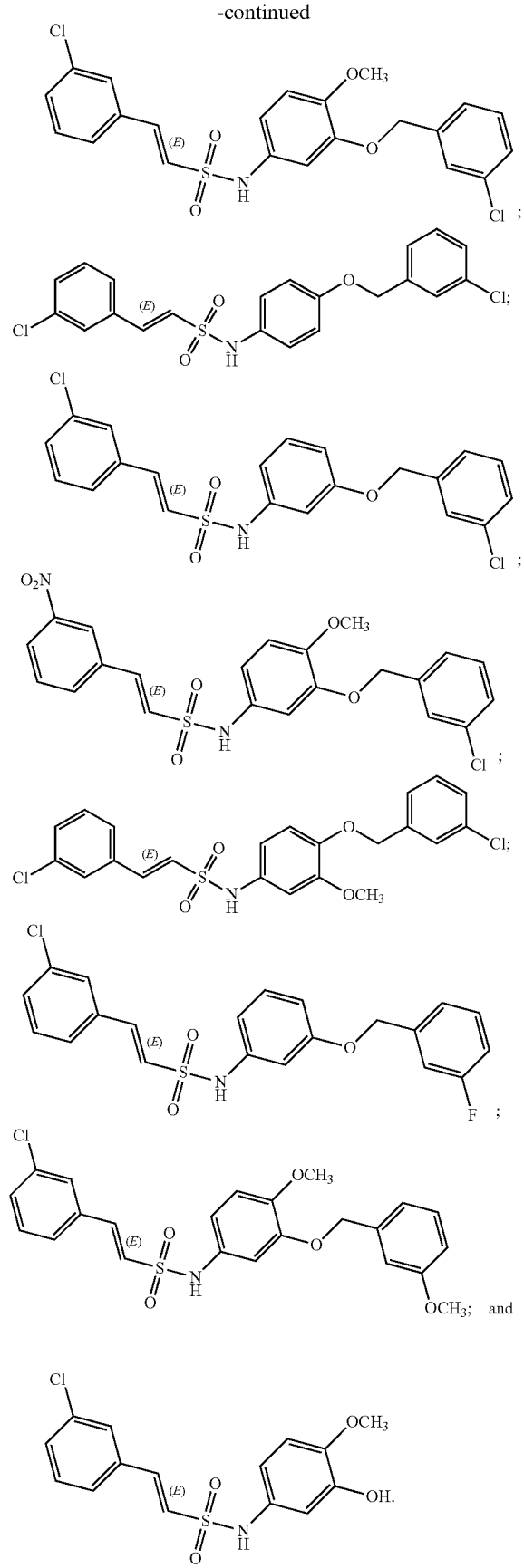
30. The method of claim 26, wherein $R_2$ is
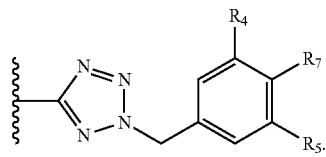
31. The method of claim 30, wherein the compound of Formula (I) is selected from the group consisting of:
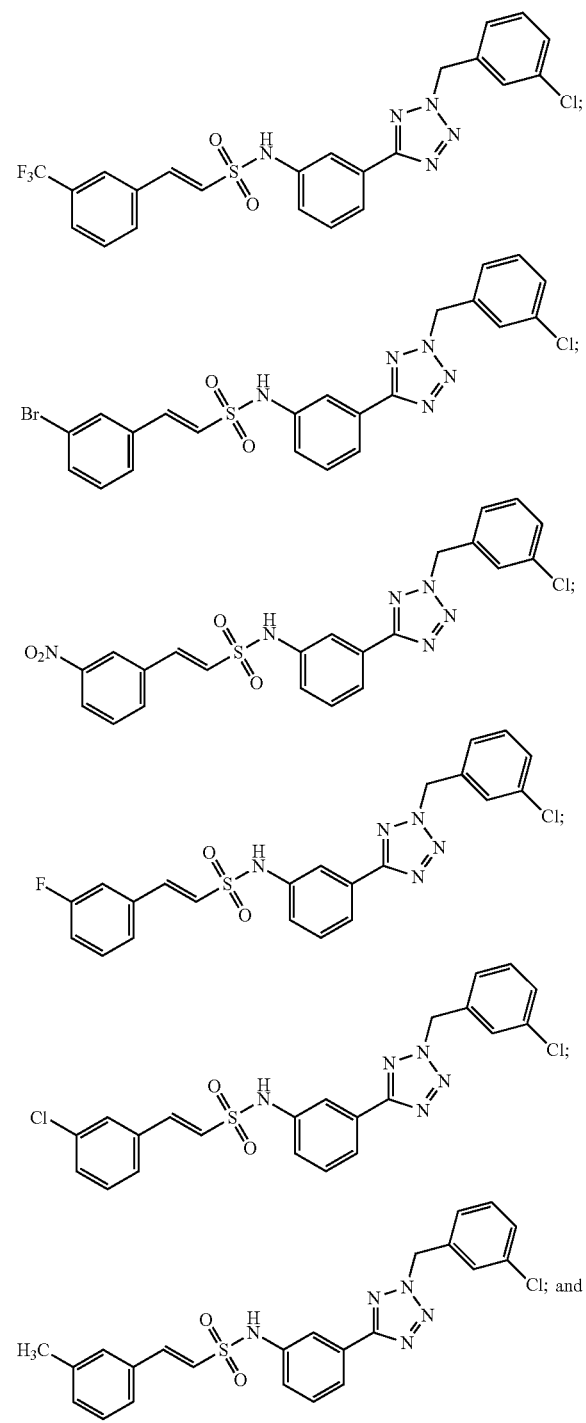

-continued

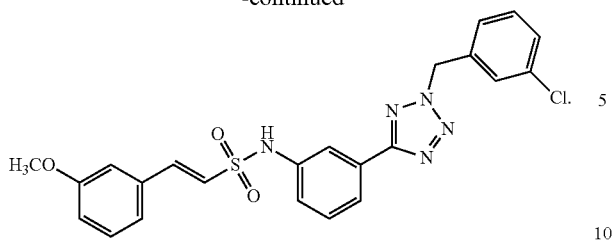

32. The method of claim 26, wherein the antibacterial agent is selected from the group consisting of a beta-lactam antibiotic, a fluoroquinolone, a quinolone, a macrolide, a tetracycline, and combinations thereof.

33. The method of claim 32, wherein the beta-lactam antibiotic is selected from the group consisting of a cephalosporin, a penicillin, a monobactam, a carbapenem, and a carbacephem.

34. The method of claim 32, wherein the beta-lactam antibiotic is selected from the group consisting of loracarbef, ertapenem, doripenem, imipenem/cilastatin, meropenem, cefadroxil, cefazolin, cefalotin or cefalothin, cefalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftobiprole, aztreonam, amoxicillin, ampicillin, azlocillin, carbenicillin, dicloxacillin, flucloxacillin, mezlocillin, methicillin, nafcillin, oxacillin, penicillin g, penicillin v, piperacillin, temocillin, ticarcillin, amoxicillin/clavulanate, ampicillin/sulbactam, piperacillin/tazobactam, and ticarcillin/clavulanate.

35. The method of claim 32, wherein the fluoroquinolone is selected from the group consisting of ciprofloxacin, clinafloxacin, enoxacin, fleroxacin, gatifloxacin, moxifloxacin, gemifloxacin, grepafloxacin, levofloxacin, norfloxacin, sparfloxacin, and trovafloxacin.

36. The method of claim 32, wherein the quinolone is selected from the group consisting of cinoxacin, garenoxacin, and nalidixic acid.

37. The method of claim 32, wherein the macrolide is selected from the group consisting of azithromycin, clarithromycin, dirithromycin, erythromycin, and lincomycin.

38. The method of claim 32, wherein the tetracycline is selected from the group consisting of doxycycline, minocycline, and tetracycline.

39. The method of claim 26, wherein the bacterial infection is an infection caused by a bacterium of a genus selected from the group consisting of *Staphylococcus, Streptococcus, Micrococcus, Bacillus, Listerella, Escherichia, Klebsiella, Proteus, Salmonella, Shigella, Enterobacter, Serratia, Pseudomonas, Acinetobacter, Nocardia*, and *Mycobacterium*.

40. A method for overcoming a bacterial resistance in a subject in need of treatment thereof, the method comprising administering to the subject a therapeutically effective amount of a compound of Formula (I):

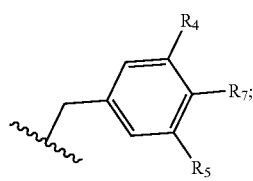

wherein:
each n is independently an integer selected from the group consisting of 1, 2, 3, 4, and 5;
each $R_2$ is independently selected from the group consisting of:

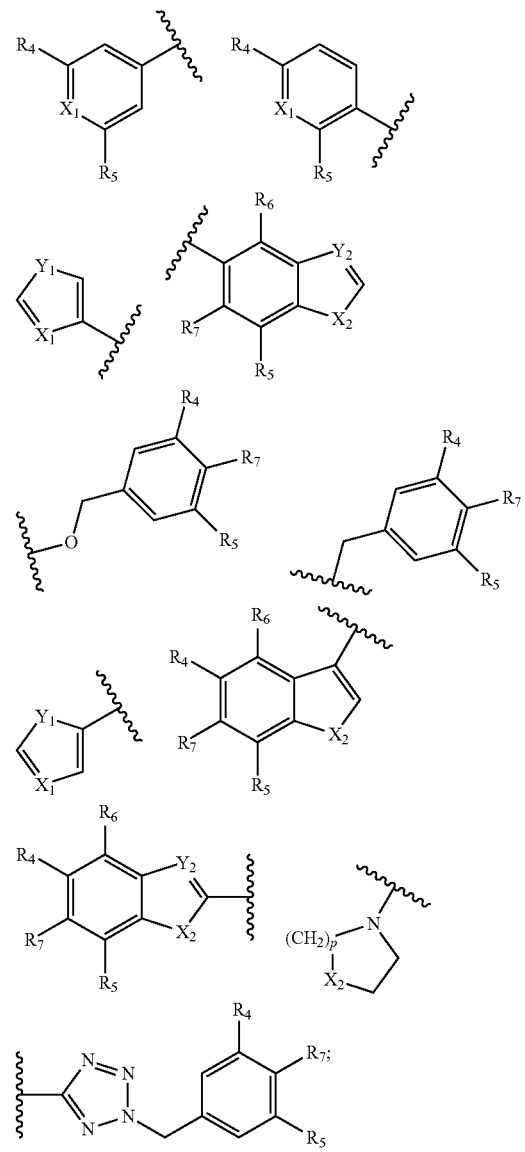

$R_3$ is selected from the group consisting of: hydrogen, hydroxyl, alkoxyl, and p is an integer selected from the group consisting of 1 and 2;
$X_1$ is selected from the group consisting of N and $CR_8$;

$X_2$ is selected from the group consisting of S, $NR_8$, and $CR_8R_9$;

$Y_1$ is selected from the group consisting of S, O, and $NR_8$;

$Y_2$ is selected from the group consisting of N and $CR_8$;

$R_1, R_4, R_5, R_6,$ and $R_7$ are each independently selected from the group consisting of hydrogen, substituted or unsubstituted alkyl, alkoxyl, hydroxyl, hydroxyalkyl, carboxyl, acyl, Cl, Br, $NO_2$, $-NH_2$, F, phenyl, cyclohexyl, benzyloxyl, and $-SO_3H$, including $-COOR_{10}$, wherein $R_{10}$ is lower alkyl, carbonyl, carbamoyl, alkylcarbamoyl, halogen, amino, nitro, nitrile, amide, haloalkyl, aryl, cycloalkyl, aralkyloxyl, and $-SO_3H$;

$R_8$ and $R_9$ are each independently selected from the group consisting of hydrogen, substituted or unsubstituted alkyl, alkoxyl, hydroxyl, hydroxyalkyl, carboxyl, acyl, including $-COOR_{10}$, wherein $R_{10}$ is lower alkyl, carbonyl, carbamoyl, alkylcarbamoyl, halogen, amino, nitro, nitrile, amide, haloalkyl, aryl, cycloalkyl, aralkyloxyl, and $-SO_3H$;

and a pharmaceutically acceptable salt, prodrug, or solvate thereof.

41. The method of claim 40, wherein $R_1$, $R_4$, $R_5$, $R_6$, and $R_7$ are each independently selected from the group consisting of t-butyl, Cl, Br, methyl, $-OCH_3$, $-NO_2$, $-NH_2$, $-OH$, $-CH_2OH$, $-CHO$, $-COOH$, $-COOCH_3$, $-COOCH_2CH_3$, $-CF_3$, $-CONHCH_3$, $-C\equiv N$, $-CONH_2$, H, F, isopropyl, phenyl, cyclohexyl, benzyloxyl, and $-SO_3H$.

42. The method of claim 40, wherein the compound of Formula (I) is selected from the group consisting of:

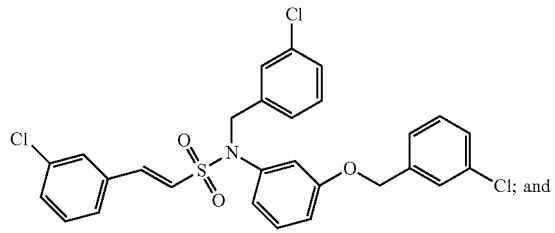

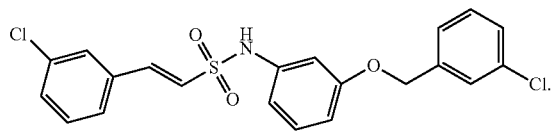

43. The method of claim 40, wherein the compound of Formula (I) is selected from the group consisting of:

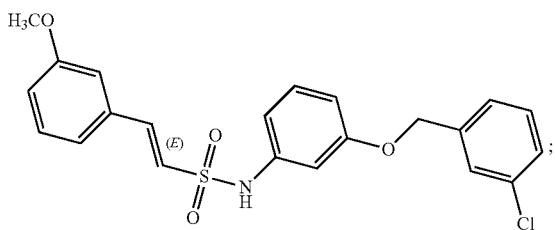

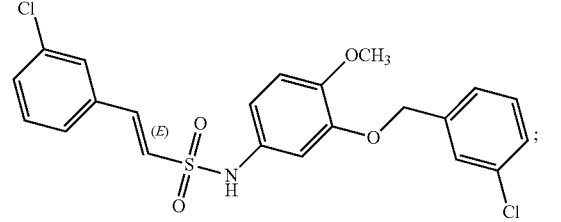

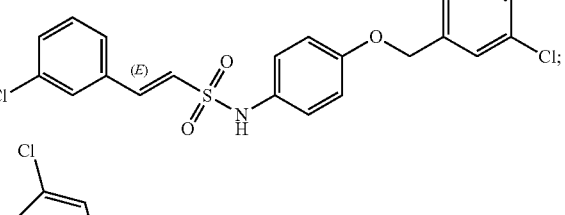

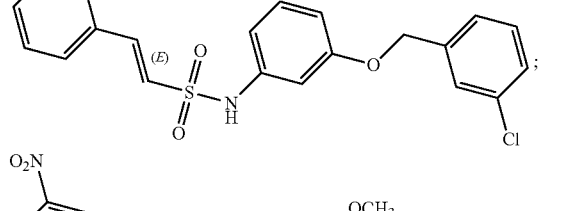

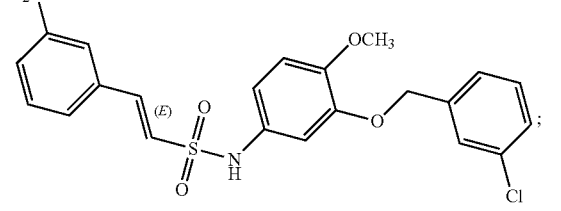

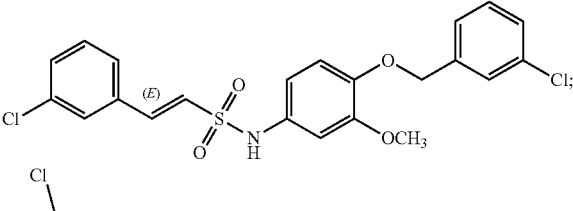

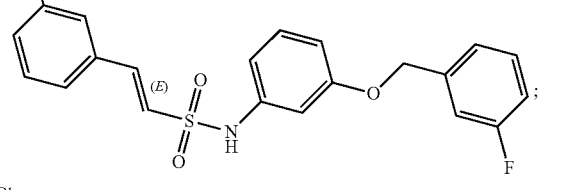

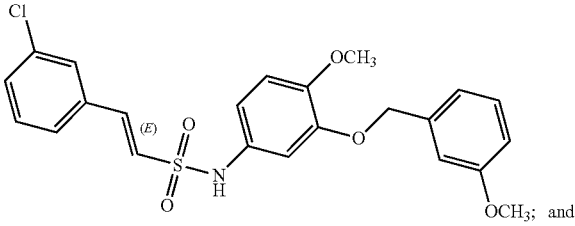

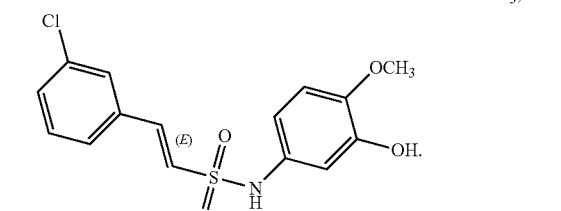

44. The method of claim 40, wherein the $R_2$ is
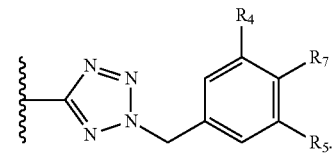
45. The method of claim 44, wherein the compound of Formula (I) is selected from the group consisting of:
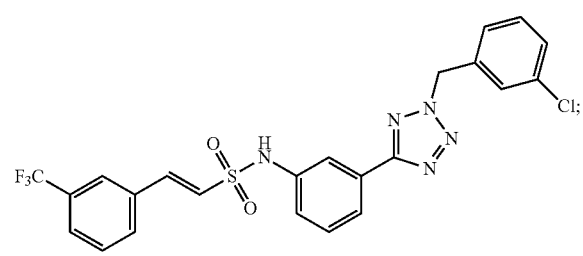
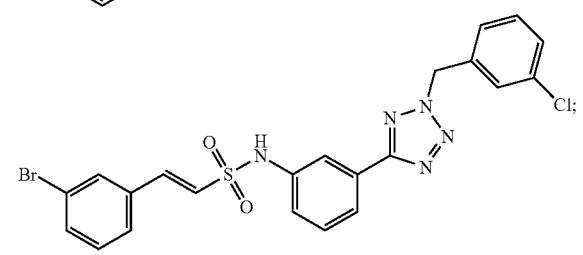
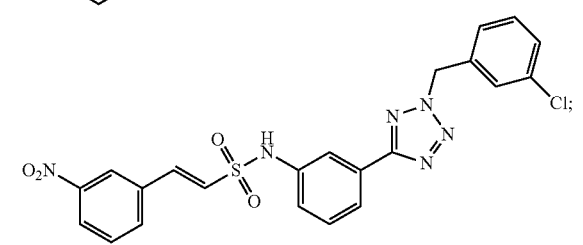
-continued
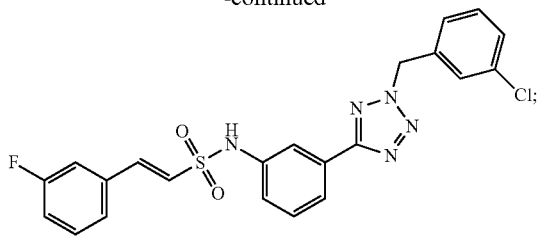
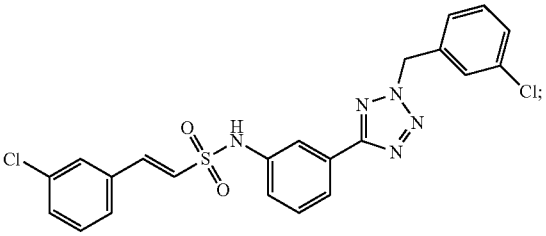
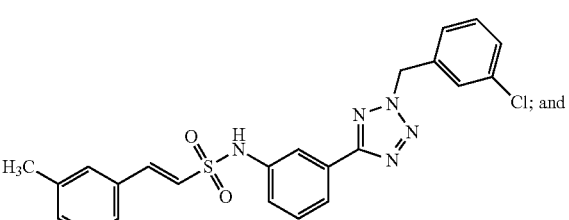
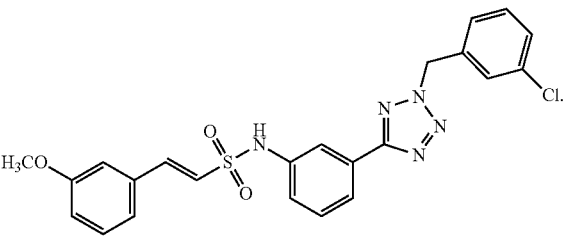
* * * * *

UNITED STATES PATENT AND TRADEMARK OFFICE
CERTIFICATE OF CORRECTION

| | | |
|---|---|---|
| PATENT NO. | : 9,730,913 B2 | Page 1 of 1 |
| APPLICATION NO. | : 14/351280 | |
| DATED | : August 15, 2017 | |
| INVENTOR(S) | : Ernesto Freire, Rogelio Siles and Patrick C. Ross | |

It is certified that error appears in the above-identified patent and that said Letters Patent is hereby corrected as shown below:

In the Specification

On Column 1, please replace the first paragraph as follows:
STATEMENT OF GOVERNMENTAL INTEREST
This invention was made with government support under GM057144, awarded by the National Institutes of Health. The government has certain rights in the invention.

Signed and Sealed this
Twenty-fourth Day of August, 2021

Drew Hirshfeld
*Performing the Functions and Duties of the*
*Under Secretary of Commerce for Intellectual Property and*
*Director of the United States Patent and Trademark Office*